(12) United States Patent
Marasco et al.

(10) Patent No.: US 10,774,134 B2
(45) Date of Patent: Sep. 15, 2020

(54) CONSERVED HEMAGGLUTININ EPITOPE, ANTIBODIES TO THE EPITOPE, AND METHODS OF USE

(71) Applicants: Dana-Farber Cancer Institute, Inc., Boston, MA (US); Burnham Institute for Medical Research, La Jolla, CA (US)

(72) Inventors: Wayne A. Marasco, Wellesley, MA (US); Jianhua Sui, Boston, MA (US); Robert C. Liddington, La Jolla, CA (US)

(73) Assignees: Dana-Farber Cancer Institute, Inc., Boston, MA (US); Burnham Institute for Medical Research, La Jolla, CA (US)

( * ) Notice: Subject to any disclaimer, the term of this patent is extended or adjusted under 35 U.S.C. 154(b) by 0 days.

(21) Appl. No.: 16/013,085

(22) Filed: Jun. 20, 2018

(65) Prior Publication Data

US 2019/0062408 A1 Feb. 28, 2019

Related U.S. Application Data

(63) Continuation of application No. 13/061,026, filed as application No. PCT/US2009/054950 on Aug. 25, 2009, now abandoned.

(60) Provisional application No. 61/154,400, filed on Feb. 22, 2009, provisional application No. 61/150,231, filed on Feb. 5, 2009, provisional application No. 61/091,599, filed on Aug. 25, 2008.

(51) Int. Cl.
*A61K 39/145* (2006.01)
*A61K 39/00* (2006.01)
*C07K 14/005* (2006.01)
*C07K 16/10* (2006.01)
*A61K 39/12* (2006.01)

(52) U.S. Cl.
CPC ........ *C07K 16/1018* (2013.01); *C07K 14/005* (2013.01); *A61K 39/00* (2013.01); *A61K 2039/505* (2013.01); *C07K 2299/00* (2013.01); *C07K 2317/76* (2013.01); *C07K 2317/92* (2013.01); *C07K 2319/40* (2013.01); *C12N 2760/16022* (2013.01); *C12N 2760/16034* (2013.01)

(58) Field of Classification Search
CPC ........... C12N 2760/16134; C12N 2760/16122; A61K 39/145; A61K 39/12; C07K 16/1018
See application file for complete search history.

*Primary Examiner* — Barry A Chestnut

(57) ABSTRACT

Disclosed are antibodies that bind to the stem region of influenza hemagglutinin in the neutral pH conformation, hemagglutinin epitopes to the stem region, and methods of making and using both.

13 Claims, 18 Drawing Sheets

Specification includes a Sequence Listing.

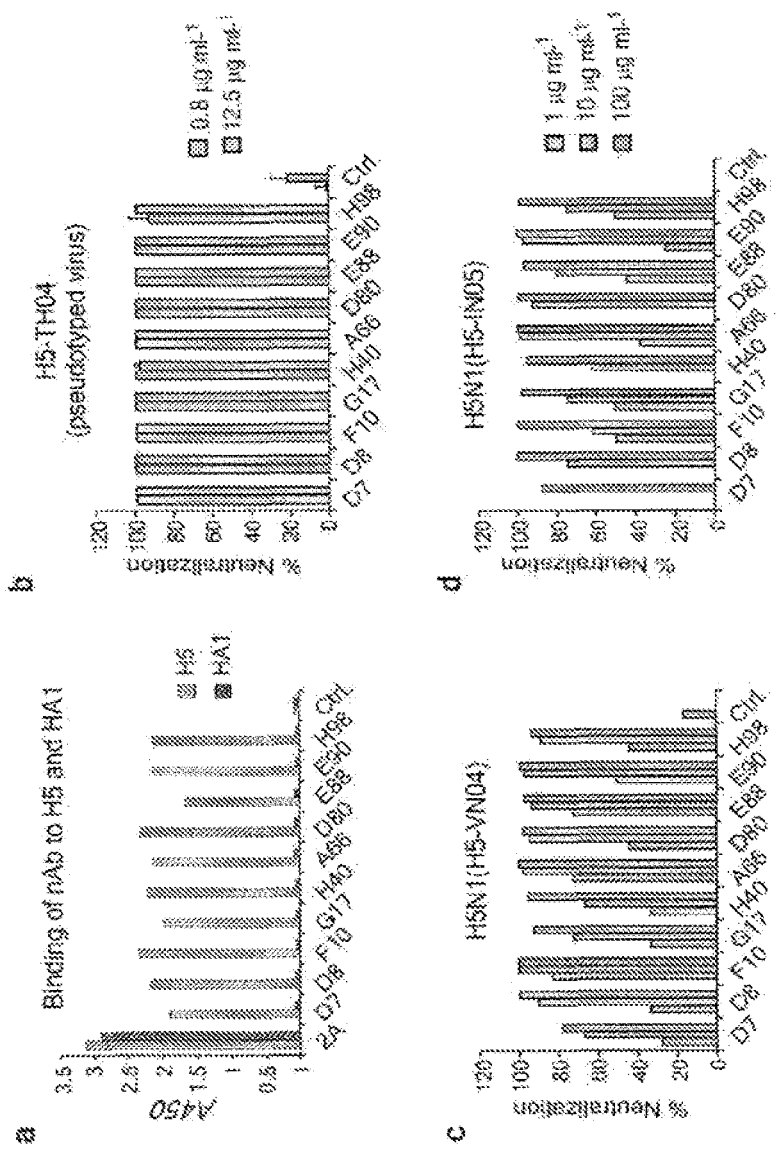
Figure-1(Marasco)

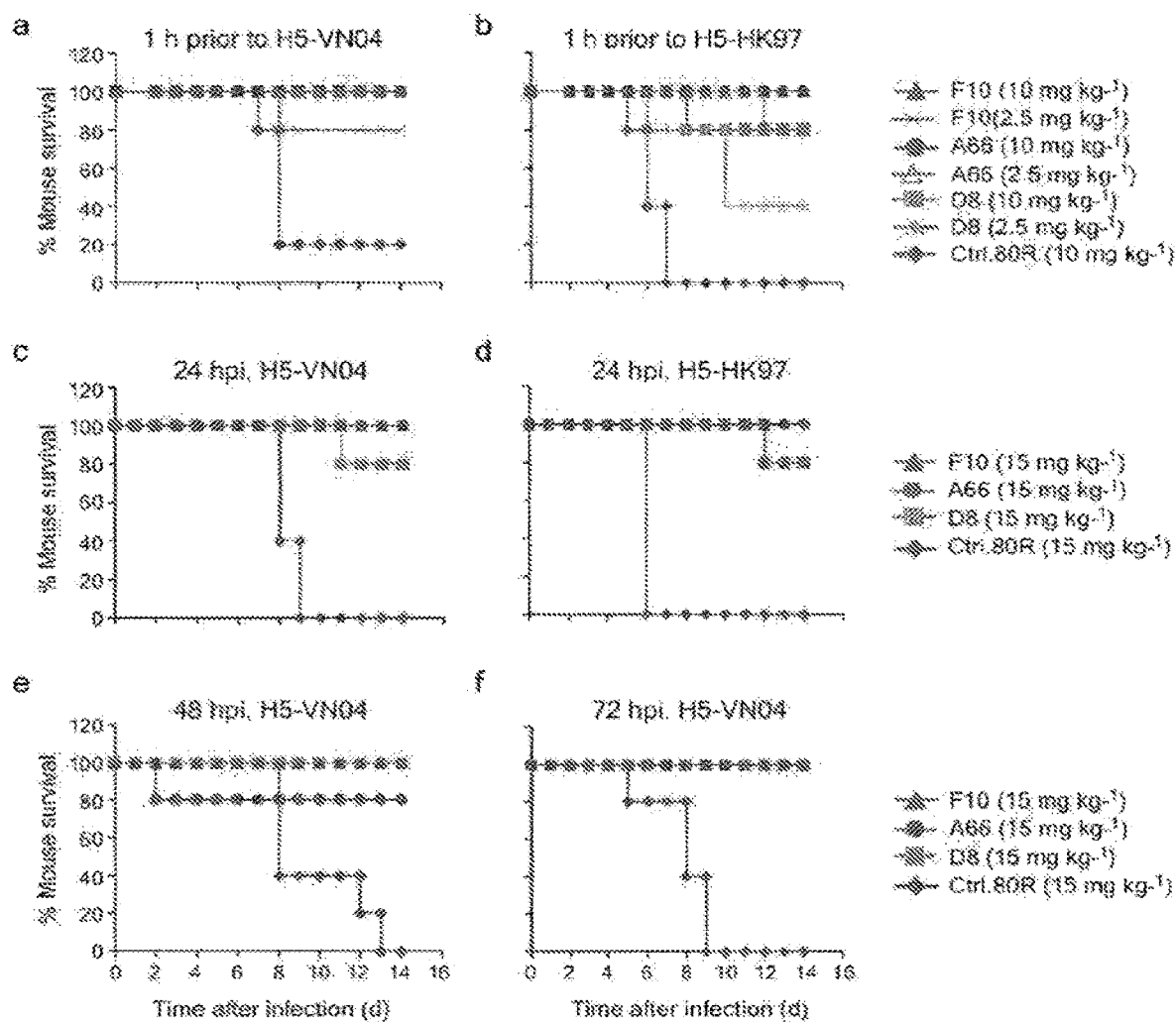
Figure-2(Marasco)

Figure-3(Marasco)

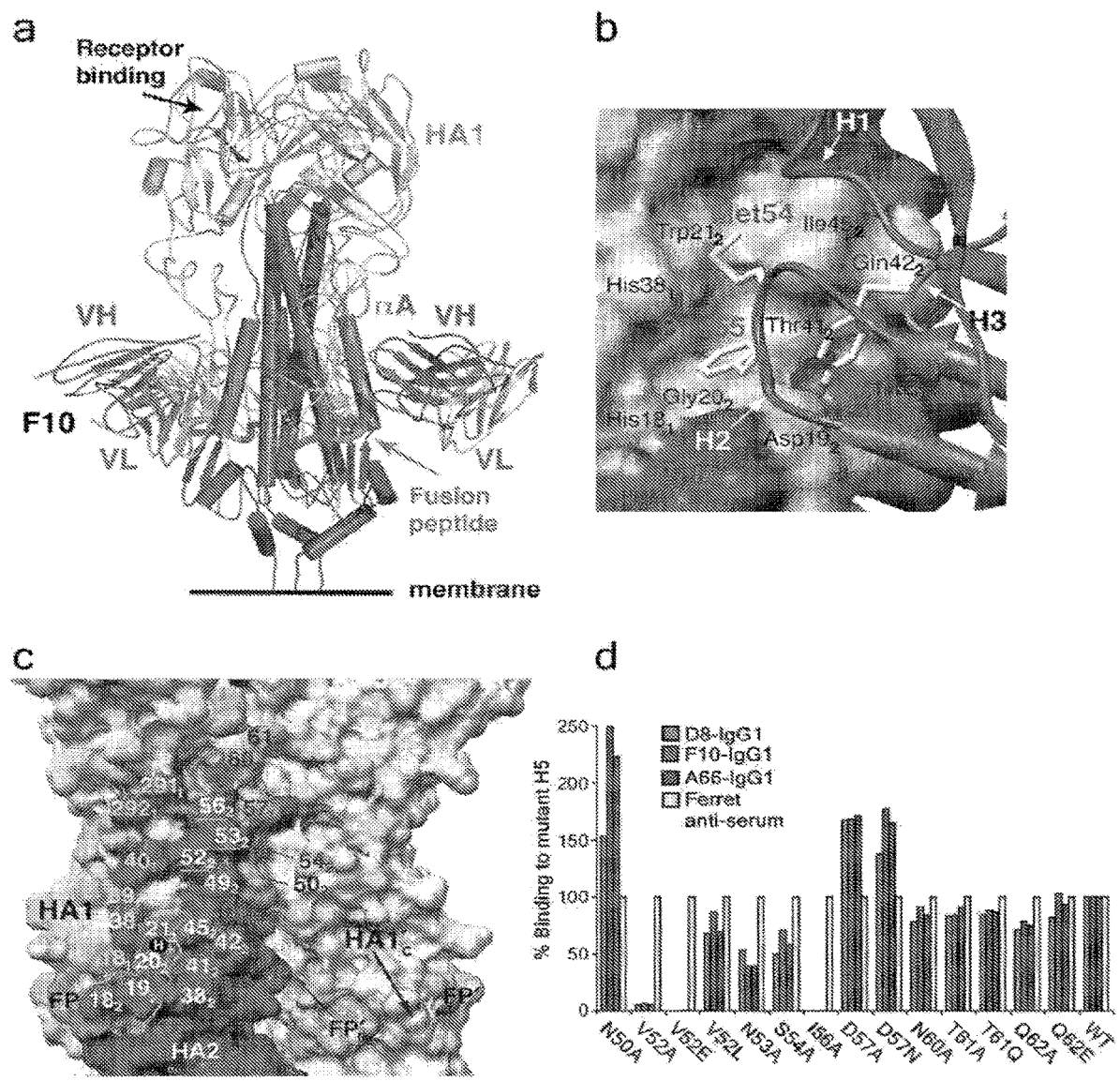
Figure-4 (Marasco)

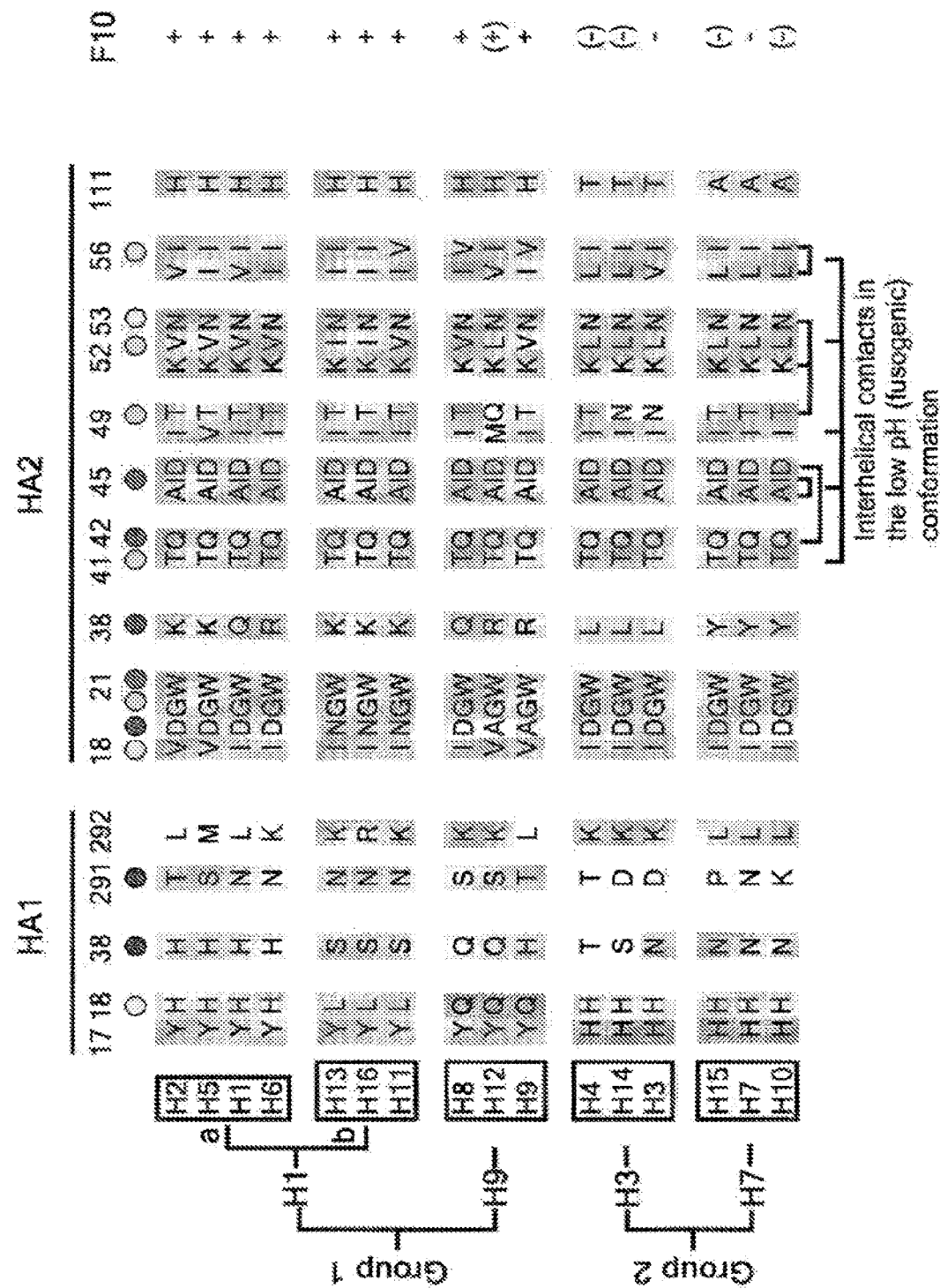

Figure-6 (Marasco)

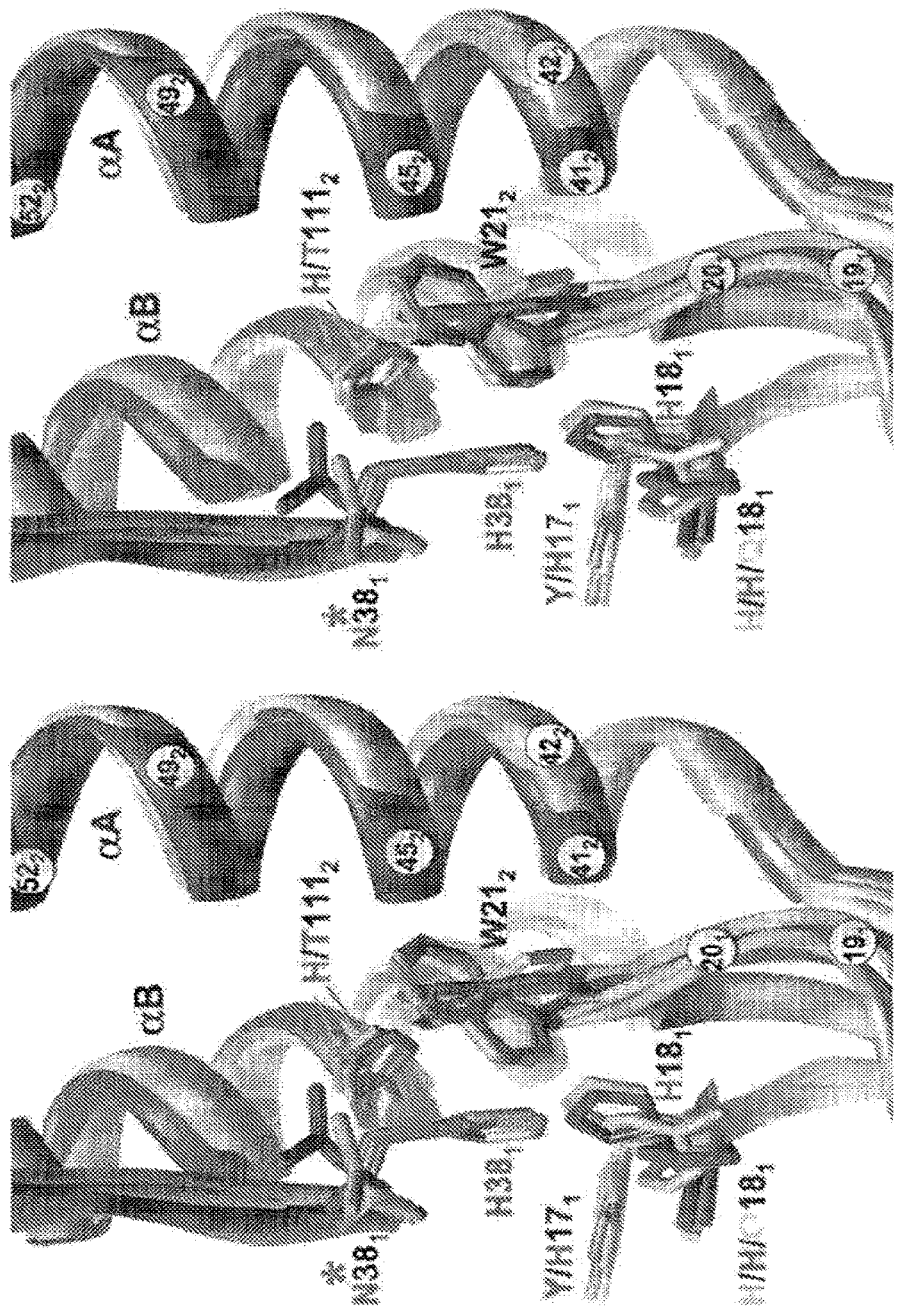
Figure-7 (Marasco)

A, Structural overview of the A/Vietnam 1203/04 trimer, receptor binding site and antigenic variation sites are highlighted on the monomer (cited from Stevens, 2006). B, Location of amino acid residues in the HA of H5N1 influenza viruses that are under positive selection (cited from Smith, 2006).

CONSERVED HEMAGGLUTININ EPITOPE, ANTIBODIES TO THE EPITOPE, AND METHODS OF USE

RELATED APPLICATIONS

This application is a continuation of U.S. application Ser. No. 13/061,026, filed Feb. 25, 2011, which is a national stage application, filed under 35 U.S.C. § 371, of International Application No. PCT/US2009/054950, filed Aug. 25, 2009, which claims the benefit of provisional applications, U.S. 60/091,599, filed Aug. 25, 2008; U.S. 61/150,231, filed Feb. 5, 2009; and, U.S. 61/154,400 filed Feb. 22, 2009, the contents which are each herein incorporated by reference in their entirety.

SEQUENCE LISTING

The instant application contains a Sequence Listing which has been filed electronically in ASCII format and is hereby incorporated by reference in its entirety. Said ASCII copy, created on Sep. 5, 2018, is named 5031461-024-US4_SL.txt and is 88,630 bytes in size.

STATEMENT REGARDING FEDERALLY SPONSORED RESEARCH

This invention was made with government support under grant numbers U01 AI074518, AI055789, and P41 RR001081 awarded by The National Institutes of Health. The government has certain rights in the invention.

FIELD OF THE INVENTION

The disclosed invention is generally in the field of influenza and specifically in the area of antibodies and immunogens for the treatments for influenza.

BACKGROUND OF THE INVENTION

Seasonal influenza A is a scourge of the young and old, killing more than 250,000 worldwide each year, while creating an economic burden for millions (W.H.O. web site who.int/mediacentre/factsheets/2003/fs211/en/. World Health Organization factsheet 211: influenza (2003)). Pandemic influenza, which occurs when a new virus emerges and infects people globally that have little or no immunity, represents a grave threat to human health: for example, the 1918 "Spanish Flu" pandemic caused an estimated 50 million deaths (Webster, 1918 Spanish influenza: the secrets remain elusive. *Proc Natl Acad Sci USA* 96, 1164-6 (1999); de Wit & Fouchier, Emerging influenza. *J Clin Virol* 41, 1-6 (2008)). Vaccines have historically been the mainstay of infection control. However, due to rapid antigenic drift, the vaccine antigen needs to be updated annually based on global influenza surveillance (W.H.O. web site who.int/csr/disease/influenza/influenzanetwork/en/index.html. (2008); Carrat & Flahault, Influenza vaccine: the challenge of antigenic drift, *Vaccine* 25, 6852-62 (2007)), and it is not always fully successful. In addition, some recent H5N1 vaccines have shown promising results (Cinatl et al., The threat of avian influenza A (H5N1). Part IV: Development of vaccines. *Med Microbiol Immunol* 196, 213-25 (2007); Subbarao & Luke H5N1 viruses and vaccines. *PLoS Pathog* 3, e40 (2007); Leroux-Roels et al., Broad Clade 2 Cross-Reactive Immunity Induced by an Adjuvanted Clade 1 rH5N1 Pandemic Influenza Vaccine, *PLoS ONE* 3, e1665 (2008); Baras et al., Cross-Protection against Lethal H5N1 Challenge in Ferrets with an Adjuvanted Pandemic Influenza Vaccine. *PLoS ONE* 3 e1401 (2008)), but none has been reported to elicit a broad neutralizing response in humans. Neuraminidase inhibitors, especially oseltamavir (Tamiflu), remain the primary antiviral treatment, but they have limited efficacy if administered late in the infection, and widespread use is likely to result in the emergence of resistant viral strains (de Jong et al., Oseltamivir resistance during treatment of influenza A (H5N1) infection, *N Engl J Med* 353, 2667-72 (2005); W.H.O. Clinical management of human infection with avian influenza A (H5N1) virus. web site who.int/csr/disease/avian_influenza/guidelines/ClinicalManagement07.pdf).

Influenza A is sub-classified by its two major surface proteins: hemagglutinin (HA or H), which mediates cell entry, first by recognizing host proteins bearing sialic acid on their surface, and second by triggering the fusion of viral and host membranes following endocytosis, allowing viral RNA to enter the cytoplasm; and neuraminidase (HA or N), which cleaves sialic acid from host and viral proteins, facilitating cell exit (Wright et al., Orthomyxoviruses, in *Fields Virology* Vol. 2 (eds. Knipe, D., Howley, P., Griffin, D., Lamb, R. & Martin, M.) 1692-1740 (Lippincott Williams & Wilkins 2006)). There are 16 HA subtypes and 9 NA subtypes which make up all known strains of influenza A viruses by various combinations of HA and NA (Wright et al. (2006)) (See FIG. 8).

The recent spread of highly pathogenic avian influenza (HPA1), H5N1, across Asia, Europe and Africa raises the specter of a new pandemic, should the virus mutate to become readily transmissible from person-to-person. The evolution of H5N1 into a pandemic threat could occur through a single reassortment of its segmented genome or through the slower process of genetic drift (Wright et al. (2006); Fauci, Pandemic influenza threat and preparedness. *Emerg Infect Dis* 12, 73-7 (2006). Nearly 400 human H5N1 infections have bees reported since 1997 from 14 countries, with a case mortality rate in the immunocompetent population above 60% (W.H.O. web site who.int/csr/disease/influenza/influenzanetwork/en/index.html. (2008)).

New therapeutic strategies that provide potent and broadly cross-protective host immunity are therefore a global public health priority. Human monoclonal antibody (mAb)-based "passive" immunotherapy is now being used to treat a number of human diseases, including Respiratory Syncytial Virus infection, and it has been proposed how immunotherapy could be used strategically in a viral outbreak setting (Marasco & Sui, The growth and potential of human antiviral monoclonal antibody therapeutics. *Nat Biotechnol* 25, 1421-34 (2007)).

BRIEF SUMMARY OF THE INVENTION

The present invention relates to an immunogen capable of inducing antibodies against a target peptide of the stem region of hemagglutinin protein of an influenza virus. The immunogen is a peptide or a synthetic peptide. In particular, the immunogen of this invention comprises one or more epitopes or epitope units. Optionally, the immunogen further comprises a general immune stimulator. These immunogens of the preset invention are capable of inducing antibodies against influenza A virus to prevent infection by the virus.

In one aspect the invention provides an immunogen having an epitope or epitope unit recognized by a protective monoclonal antibody having the specificity for the stem region of hemagglutinin protein of an influenza virus.

The antibody binds both the HA1 and HA2 peptide. In some embodiments the epitope is recognized by monoclonal antibody D7, D8, F10, G17, H40, A66, D80, E88, E90, or H98 or a monoclonal antibody that competes with the binding of monoclonal antibody D7, D8, F10, G17, H40, A66, D80, E88, E90, or H98 to the HA protein. Preferably, the epitope is the F10 epitope.

In some embodiments the hemagglutinin protein is in the neutral pH conformation.

The immunogen in a peptide or a synthetic peptide.

In some aspects the immunogen is a conjugate leaving one or more peptides or peptide fragments that are spatially positioned relative to each other so that they together form a non-linear sequence which mimics the tertiary structure of an F10 epitope. Optionally, the one or more peptides or peptide fragments are linked to a backbone. The conjugate competes with the binding of monoclonal antibody F10 to the HA protein.

The c conformation of the epitope is defined by amino acid residues 18, 38, 39, 40 and 291 of HA1 and 18, 19, 20, 21, 38, 41, 42, 45, 49, 52, 53, and 56 of HA2 when the hemagglutinin in the neutral pH conformation.

In some embodiments the immunogen is a peptide having one or more of the following amino acid sequences:

$[Xaa_0]_m$-$Xaa_1$-$Xaa_2$-$[Xaa_0]_p$ (SEQ ID NO: 125)

$[Xaa_0]_m$-$Xaa_1$-$Xaa_2$-$[Xaa_0]_p$ (SEQ ID NO: 126)

$[Xaa_0]_m$-$Xaa_1$-$Xaa_2$-$Xaa_3$-$Xaa_4$-$[Xaa_0]_p$ (SEQ ID NO: 127)

$[Xaa_0]_m$-$Xaa_1$-$[Xaa_0]_q$ $Xaa_2$-$Xaa_3$-$[Xaa_0]_q$ $Xaa_4$- (SEQ ID NO: 128)

$[Xaa_0]_r$ $Xaa_5$-$[Xaa_0]_q$-$Xaa_6$ $Xaa_7$-$[Xaa_0]_q$-$Xaa_8$-

$[Xaa_0]_p$ $[Xaa_0]_m$-$Xaa_1$-$[Xaa_0]_q$ $Xaa_2$-$Xaa_3$-$[Xaa_0]_q$ $Xaa_4$- (SEQ ID NO: 129)

$[Xaa_0]_r$ $Xaa_5$-$[Xaa_0]_q$-$Xaa_6$ $Xaa_7$-$[Xaa_0]_s$-$[Xaa_8]_t$-

$[Xaa_0]_p$

Wherein, m, and p are independently 0 or 1-100, preferably about 1-90, 1-80, 1-70, 1-60, 1-50, 1-40, 1-30, 1-20 or 1-10; q is 2, r is 3, s is 0 or 2, and t is 0 or 1, and $Xaa_0$, is independently any amino acid. Preferably s is 2 and t is 1.

Preferably $Xaa_1$ of SEQ ID NO: 125 is S, T, F H or Y and $Xaa_2$ of SEQ ID NO: 125 is H, Y, M, L or Q. Most preferably, $Xaa_1$ of SEQ ID NO: 125 is Y. Most preferably, $Xaa_2$ of SEQ ID NO: 125 is H.

Preferably, $Xaa_1$ of SEQ ID NO: 126 is H, Q, Y, S, D, N or T and $Xaa_2$ of is SEQ ID NO: 126 is Q, E, K, I, V, M, E, R or T. Most preferably. $Xaa_1$ of SEQ ID NO: 126 is H. Most preferably, $Xaa_2$ of SEQ ID NO: 126 is Q.

Preferably, in SEQ ID NO: 127 $Xaa_1$ is I, V, M, or L; $Xaa_2$ is D, N, H, Y, D, A, S or E, $Xaa_3$ is G or A, md $Xaa_4$ is W, R, or G. Most preferably, in SEQ ID NO: 127 $Xaa_1$ is V; $Xaa_2$ is D, $Xaa_3$ is G, and $Xaa_4$ is W.

Preferably is SEQ ID NO:128 or SEQ ID NO:129, $Xaa_1$ is K, Q, R, N, L, G, F, H or Y; $Xaa_2$ is S or T, $Xaa_3$ is Q or P; $Xaa_4$ is F, V, I, M, L or T; $Xaa_5$ is I, T, S, N, Q, D, or A; $Xaa_6$ is I, V, M, or L; $Xaa_7$ is N, S, T, or D and $Xaa_8$ is I, F, V, A, or T. Most preferably, SEQ ID NO:128 or SEQ ID NO:129, $Xaa_1$ is K; $Xaa_2$ is T, $Xaa_3$ is Q; $Xaa_4$ is I; $Xaa_5$ is T; $Xaa_6$ is V; $Xaa_7$ is N, and $Xaa_8$ is I.

In some aspects of the inventions, one or more amino adds are D-amino acids.

Optionally, the immunogen further comprises an adjuvant or is conjugated to a carrier.

In various aspects the invention includes a composition containing the immunogen together with one or more pharmaceutically acceptable excipients, diluents, and/or adjuvants. In some embodiments the composition further comprises an ant-influenza antibody of antigen binding fragment thereof. Preferably, the antibody is monoclonal antibody D7, D8, F10, G17, H40, A66, D80, E88, E90, or H98 or a monoclonal antibody that competes with the binding of monoclonal antibody D7, D8, F10, G17, H40, A66, D80, E88, E90, or H98 to the HA protein.

Also provided by the invention is nucleic acids encoding the immunogens of the invention and composition comprising the nucleic acids.

The invention further comprises a method preventing a disease or disorder caused by an influenza virus by administering to person at risk of suffering from said disease or disorder an immunogen composition described herein. Optionally, the method includes further administering an anti-viral drug, a viral entry inhibitor or a viral attachment inhibitor. The anti-viral drug is a neuraminidase inhibitor, a HA inhibitor, a sialic acid inhibitor or an M2 ion channel. The M2 ion channel inhibitor is amantadine or, rimantadine. The neuraminidase inhibitor zanamivir, or oseltamivir phosphate.

In another aspect the method includes further administering one or more antibodies specific to a Group I influenza virus and or a Group II influenza virus The antibody is administered at a dose sufficient to neutralize the influenza virus.

Administration is prior to or after exposure to influenza virus.

Also disclosed are methods of treating subjects and methods of screening and producing antibodies. For example, disclosed is a method of treating a subject suffering or at risk of influenza infection, the method comprising administering to the subject one or more of the disclosed antibodies, such as the disclosed HA stem antibodies. For example, disclosed is a method of treating a subject, the method comprising administering to the subject the stem region of influenza hemagglutinin in the neutral pH conformation in isolation from other components of influenza virus, wherein the subject produces an immune response to the stem region. For example, disclosed is a method of treating a subject, the method comprising administering to the subject the stem region of influenza hemagglutinin in the neutral pH conformation in isolation from the head region of hemagglutinin, wherein the subject produces an immune response to the stem region. For example, disclosed is a method of treating a subject, the method comprising administering to the subject influenza hemagglutinin in the neutral pH conformation in isolation from other components of influenza virus, wherein the head region of the hemagglutinin is modified to reduce the antigenicity of the head region, wherein the subject produces an immune response to the stem region. For example, disclosed is a method, the method comprising screening antibodies reactive to hemagglutinin for binding to hemagglutinin immobilized on a surface, thereby identifying antibodies of interest. For example, disclosed is a method comprising screening antibodies reactive to hemagglutinin for binding to the stem region of influenza hemagglutinin in the neutral pH conformation in isolation from the head region of hemagglutinin, thereby identifying antibodies of interest. For example, disclosed is a method comprising screening antibodies reactive to hemagglutinin for binding to influenza hemagglutinin in the neutral pH conformation in isolation from other components of influenza virus, wherein the head region of the hemagglutinin is modified to reduce the antigenicity of the head region, thereby identifying antibodies of interest.

In some forms, the head region of the hemagglutinin can be modified by removing or replacing glycosylation sites. In some forms, the head region of the hemagglutinin can be modified by adding glycosylation sites. In some forms, the head region of the hemagglutinin can be modified by removing all or a portion of the head region.

In some forms, the disclosed antibodies, disclosed hemagglutinins, and disclosed methods can produce an immune reaction in a subject. For example, in some forms, the subject can produce an immune response that prevents or reduces the severity of an influenza infection. In some forms, the immune response can be reactive to influenza viruses within a subtype. In some forms, the immune response can be reactive to influenza viruses in each subtype within a cluster. In some forms, the immune response can be reactive to influenza viruses in each cluster within a group. In some forms, the immune response can be reactive to all influenza viruses in each subtype within a group. In some forms, the immune response can be reactive to influenza viruses within group 1.

In some forms, the disclosed methods can further comprise screening the antibodies of interest for competing with antibody F10 for binding to hemagglutinin, thereby identifying F10-competing antibodies. In some forms, the hemagglutinin can be hemagglutinin from a group 2 influenza virus. In some forms, the hemagglutinin can be hemagglutinin from a group 1 influenza virus. In some forms, the disclosed methods can further comprising producing the identified antibodies. Also disclosed are antibodies produced by the disclosed methods. Also disclosed are antibodies identified by the disclosed methods.

The disclosed compositions and methods are based upon the discovery of monoclonal antibodies which neutralize the influenza virus, e.g. influenza A virus. The influenza A virus is a Group I influenza A virus such as a H1 cluster influenza virus. The H1 cluster influenza virus is an H1a cluster or an H1b cluster. The monoclonal antibody is fully human. In some forms, the monoclonal antibody can be a bivalent antibody, a monovalent antibody, a single chain antibody or fragment thereof. Specifically, such monoclonal can bind to an epitope on the stem region of the hemagglutinin protein (HA), such as HA1 or HA2 polypeptide. The epitope can be non-linear.

The epitope can comprise both the HA1 and HA2. The epitope can be non-linear. In some forms the epitope can comprise the amino acid position 18, 38, 40, 291 of the HA1 polypeptide and the amino acid at position 18, 19, 20, 21, 38, 41, 42, 45, 49, 52, 53 and 56 of the HA2 polypeptide.

The disclosed compositions and methods are further based upon the discovery of a protocol for generating broadly neutralizing human antibodies that target a highly conserved epitope in the stem region of HA. Using the trimeric H5 ectodomain expressed in baculovirus which produces shorter N-glycans and uncharged mannoses absorbed on a plastic surface, allowed for the dominant presentation of the stem epitope while masking the normally immunodominant globular head. Accordingly, also disclosed is a method of producing an isolated antibody that specifically binds a pathogenic enveloped virus by exposing a single chain or Fab expression library to a membrane fusion protein of the virus, identifying an antibody in the library that specifically binds said protein; and isolating the antibody from the library. The fusion protein can be immobilized on a solid surface, e.g. plastic. In some forms the fusion protein can have modified glycosylations compared to a wild type fusion protein. For example, the fusion can be produced in a non-mammalian cell such as an insect cell. The fusion protein can be, for example, a trimeric hemagglutinin (HA) protein.

Also disclosed is a method of vaccinating a subject against pathogenic enveloped virus such as an influenza virus by administering to the subject, for example, a membrane fusion protein (e.g., a trimeric hemagglutinin (HA) protein coated) or embedded in a biologically compatible matrix. In some forms the fusion protein can have modified glycosylations compared to a wild type fusion protein.

Also disclosed is a composition comprising a monoclonal antibody as described herein and kits containing the composition in one or more containers and instructions for use.

The invention further provides a method of screening a compound for binding to an F10 antibody by contacting said F10 antibody with a compound of interest and detecting a compound-antibody complex. Also included in the invention are the compound identified by the method and their use as immunogens.

Unless otherwise defined, all technical and scientific terms used herein have the same meaning as commonly understood by one of ordinary skill in the art to which this disclosed subject matter belongs. Although methods and materials similar or equivalent to those described herein can be used in the practice or testing of the disclosed subject matter, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 1A to 1D show in vitro binding and neutralization of anti-H5 antibodies. (A) The 10 Abs were converted to soluble scFv-Fcs (scFv linked to Hinge, CH2 and CH3 domains of human IgG1) and evaluated for binding to trimeric H5-TH04 or monomeric HA1 of H5-TH04 coated on an ELISA plate. The H5 scFv-Fcs recognizes trimeric H5 but not HA1. An antibody raised against HA1 ("2A") recognized both. (B) Neutralization of H5-TH04-pseudotyped viruses (virus-like particles with HIV-1 only cores that display H5 on their surface). % neutralization at 2 concentrations is shown with standard deviation (s.d.) bars. The mAb 80R (Sui et al. (2004)) was used as a negative control ("Ctrl."). (C-D) Neutralization of wild type H5-VN04 and H5-IN05 by the 10 scFv-Fcs at three concentrations using a plaque reduction assay. Results are consistent with those obtained from a microneutralization assay.

FIGS. 2A to 2F show prophylactic and therapeutic efficacy of anti-H5 neutralizing mAbs ("nAbs") in mice. (A and B) Prophylactic efficacy. % survival of mice treated with anti-H5 nAbs or control mAb 1 h before lethal challenge by i.n. inoculation with (A) H5-VN04 or (B) H5-HK97 viruses. (C-F). Therapeutic efficacy. Mice were inoculated with H5-VN04 and injected with nAbs at 24, 48, 72 h post-inoculation (hpi) (C, E and F) or with H5-HK97 at 24 hpi (D).

FIGS. 3A and 3B show neutralization mechanism. (A) nAbs do not inhibit cell-binding of full-length HA from H5-TH04-pseudotyped HIV-1 viruses. None of the 3 nAb-treated viruses inhibited cell binding; mouse anti-H5 mAb, 17A2.1.2, and ferret anti-H5N1 serum, which inhibit haemagglutination, were used as positive controls; anti-SARS spike protein ("80R") and anti-HA1 ("2A") were used as negative controls. Vertical bars represent s.d. (B) All 3 nAbs inhibit cell fusion. HeLa cells were transfected with H5-TH04-expressing plasmid and expose a pH 5.0 buffer for 4 mins in the presence or absence of nAbs. Syncytia formation induced by brief exposure to pH 5.0 was completely inhibited by D8, F10 and A66, at 20 µml$^{-1}$ (~0.13 µM), whereas controls ("80R" and anti-HA1 mAb ("2A")) at the same concentration had no effect.

FIGS. 4A to 4D show structure of the H5-F10 complex. (A) Structure of the H5 trimer bound to F10 (scFv). H5 is very similar to the uncomplexed structure (Yamada et al. (2006)) (pairwise RMSD (Cαa)=1.0 and 0.63 Å for 2 independent trimers). HA1 is depicted by the light colored ribbon diagram at the top of the figure, HA2 is depicted by the 5 α helices and 4 β strands at the bottom of the figure closest to the membrane as well as the 3 long α helices in the middle of the figure approximately 5.5 cm high, the αA-helix of HA2 is represented by 3 vertical α helices approximately 2 cm high (one is hidden toward the back of the complex), the "fusion peptide" (FP) is a thin tubular structure that wraps horizontally around the bottom of the 3 long α helices of HA2 (identified by an arrow labeled Fusion Protein), and F10 (VH and VL) represented by the ribbon diagrams on either side of HA2 plus a third F10 molecule hidden behind the stem. (B) Close-up of the epitope showing H5 as a molecular surface, with selected epitope residues labeled. The fusion peptide is represented by at approximately 1 cm in diameter light-shaded area beginning underneath the Trp21 label and continuing down to the end of the figure (seen underneath the Gly20 and Asp19 labels). The light-shaded area seen underneath the Met35 and Thr41 labels and everything to the right of those residues are not a part of the fusion peptide. The tip of F10 (the ribbon structure) and selected CDR side-chains are shown. Of 1500 Å$^2$ buried surface at the interface, 43% involves hydrophobic interactions. (C) Surface of the central stem region, showing two H5 monomers. One monomer has HA1 depicted by the light-shaded region on the far left of the figure and HA2 depicted by the dark colored region without any residues labeled; the path of FP through the epitope is outlined, while mutations not affecting binding are the lightly shaded region labeled with $50_2$, $54_2$, $57_2$, and $61_2$ (see FIG. 4D). The fusion peptides (FP and FP') are labeled in both monomers. HA2 epitope residues are labeled $18_2$, $19_2$, $20_2$, $21_2$, $38_2$, $41_2$, $42_2$, $45_2$, $49_2$, $52_2$, $53_2$, and $56_2$ and HA1 epitope residues are labeled $18_1$, $38_1$, $39_1$, $40_1$, $292_1$ and $291_1$. The position of buried residue $H111_2$ is shown as a black ball labeled "H". (D) Binding of the 3 nAbs to H5 mutants in the αA helix. Note the very similar response to all mutants tested. Mutations were made either to alanine or to the corresponding H7 residue. 293T cells were transiently transfected with mutants; 24 hours after transfection, nAbs or ferret anti-H5N1 serum were used to stain the transfected cells. Mean Fluorescent Intensity (MFI) was normalized against ferret anti-serum (100%) to account for different expression levels.

FIG. 5 shows sequence conservation in HA Groups, Clusters and Subtypes at the F10 epitope. Circles below residue numbers indicate estimated contribution to the binding energy at each position. Positions 19, 21 and 45 of HA2 show a strong contribution. Position 18 of HA1 and positions 18, 20, 41, 49, 52, 53 and 56 of HA2 show intermediate contribution. Positions 38 and 291 of HA1 and positions 38 and 42 of HA2 show neutral contribution. Residues without a circle are not directly involved in the epitope but are discussed in the text. Many residues are conserved among groups, clusters and/or subtypes. Residues 18, 20, 21, 41, 42, 44-46, 48, 49, 51-53, 55 and 56 are all highly conversed for all clusters/groups except H12 at residues 48 and 49 and H14 and H3 at residue 49. Group 1 has cluster/subtype specific residues at 17 of HA1 and 38 and 111 of HA2. Subtype H3 and cluster H7 are identical at HA1 residue 38 and cluster H1b and subtypes H8 and H12 and cluster H3 are similar at HA1 residue 292. Group 2 is identical at residue 17 of HA1 and Group 1 cluster H9 is identical at residue 18 of HA1. Group 1 cluster H1a and Group 2 are similar at residue 18 of HA1 as well as clusters H1a and H9 at residue 38 of HA1. Subtypes H1 and H6 and cluster H1b are identical at residue 291 of HA1. Cluster H1a, subtype H8 and cluster H7 are identical at residue 19 of HA2. Cluster H3 is identical at residue 38 of HA2 and while residue 111 of HA2 is also identical within the cluster. Cluster H1b and cluster H7 are identical at residues 18 and 292 of HA1, respectively. Cluster H1b at residue 38 of HA1 and subtypes H2 and H5 and cluster H9 at residue 291 of HA1 are similar. Cluster H7 is identical at residues 38 of HA2 and 111 of HA2, respectively. The network of inter-helical contacts that stabilize the fusogenic structure (Bullough et al., Structure of influenza haemagglutinin at the pH of membrane fusion. Nature 371, 37-43 (1994)) are indicated below the HA2 sequences. Subtypes that can be recognized/neutralized by F10 are indicated with "+" on the far right. "(+) or (−)" indicates a predicted positive/negative binding. Amino acid at positions 18-21 of HA2 are VDGW (SEQ ID NO:20), IDGW (SEQ ID NO:21), INGW (SEQ ID NO:22), and VAGW (SEQ ID NO:23).

FIGS. 6A to 6D show cross subtype neutralization by nAbs. (A) nAbs D8, F10 and A66 all neutralized H5-TH04, H1-SC1918, H1-PR34, H1-WSN33, H2-JP57, H6-NY98 and H11-MP74 (strains described below) pseudotyped viruses. (B) Microneutralization assay. Neutralization titers (0.1 mg ml$^{-1}$ Ab stock solution) of nAb F10 against two wild-type H5N1, three H1N1, one H2N2, one H6N1, one H6N2, one H8N4, two H9N2 and one H3N2 virus. 80R is the negative control. Vertical bars and whiskers represent the lowest and highest neutralization titer ($2^x$, values of χ are shown on the y-axis) of 2-3 independent experiments. (C-D) Prophylactic efficacy against two H1N1 strains in mice. % survival of mice treated with anti-H5 nAbs or control mAb are shown before lethal challenge by i.n. inoculation with (C) H1-WSN33 or (D) H1-PR34 viruses. Complete viral strain designations are: H1-OH83 (A/Ohio/83 (H1N1), H1-PR34 (A/Puerto Rico/8/34 (H1N1)), H1-SC1918 ((A/South Carolina/1/1918 (H1N1)), H1-WSN33 (A/WSN/1933 (H1N1)), H2-AA60 (A/Ann Arbor/6/60 (H2N2)), H2-JP57 (A/Japan/305/57(H2N2)), H3-SY97 (A/Sydney/5/97 (H3N2)), H6-HK99 (A/quail/Hong Kong/1721-30/99 (H6N1)), H6-NY98 (A/chicken/New York/14677-13/1998 (H6N2)), H7-FP34 (A/FPV/Rostock/34 (H7N1)), H8-ON68 (A/turkey/Ontario/6118/68), H9-HK(G9)97 (A/chicken/Hong Kong/G9/97 (H9N2)), H9-HK99 (A/HongKong/1073/99 (H9N2)), H11-MP74 (A/duck/memphis/546/74 (H11N9)).

FIG. 7 shows 3-dimensional comparison of the F10 epitope in Group 1 and Group 2 HAs. Stereo overlay of crystal structures of the 5 known HA subtypes in the region of the F10 epitope, showing conservation and differences between the 2 phylogenetic groups. Shown are H1, H5 and H9 (Group 1) (PDB codes 1RU7, 21BX and 1JSD); and H3 and H7 (Group 2) (PDB codes 1MQL and 1TI8). For $17_1$, Y is in Group 1 and H is in Group 2. For $18_1$, the H/H/Q in the lower left are in Group 1 and the two H in the upper right are in Group 2. For $21_2$, the two vertical W are in Group 2 while the three tilted W are in Group 1. For $38_1$, the N are in Group 2 and the H are in Group 1. For $111_2$, the H are in Group 1 and the T are in Group 2. RMS differences for pair-wise overlays are 0.56±0.11 Å (observed range, Group 1); 0.75 Å (Group 2); and 1.21±0.12 Å between groups. Consistent differences between phylogenetic groups include the orientation of $W21_2$ and alternative side-chain directions at $18_1$ and $38_1$, which are linked to the packing of buried $His111_2$ (the putative pH trigger in Group 1; absent in Group 2); and the burial of the larger tyrosine (Group 1) versus histidine (the putative pH trigger in Group 2) at $17_1$. Of particular note, $N38_1$ is glycosylated in 4 members of the Group 2 clusters. Other epitope residues are indicated by numbered circles.

FIG. 13A is an illustration of the structure of the A/Vietnam 1203/04 trimer. The receptor binding site and antigenic variation sites are highlighted on the monomer.

FIG. 13B is an illustration showing the location of amino acid residues in the HA of H5N1 influenza viruses that are under positive selection.

Figure 14:
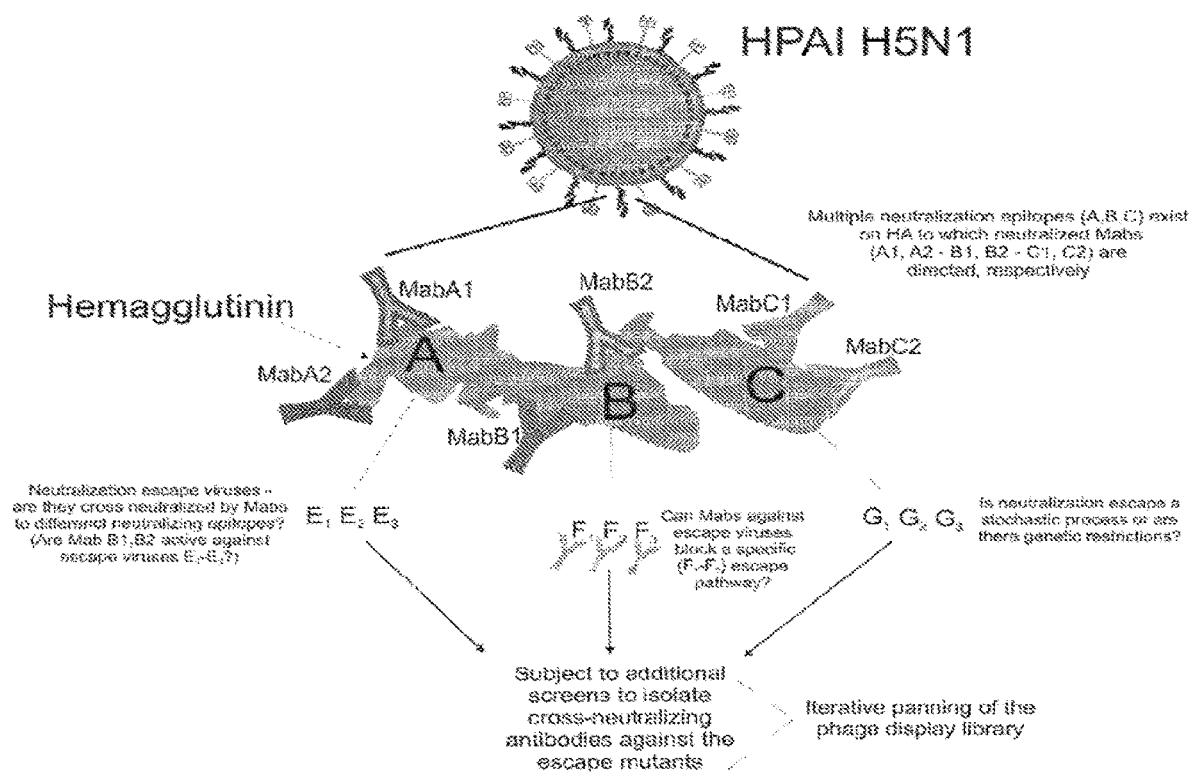

FIG. 14 is a schematic illustration of convergent combination Immunotherapy for H5N1.

Figure 15:
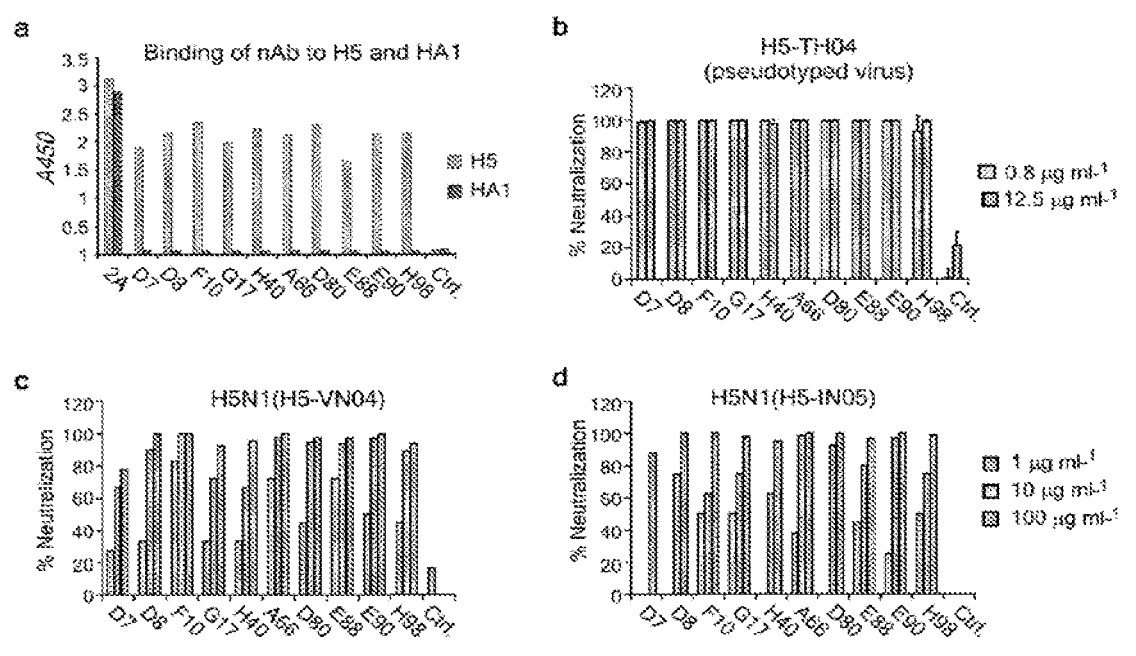

FIG. 15 shows in vitro binding and neutralizing of anti-H5 antibodies. (a) The 10 Abs were converted to soluble scFv-Fcs (scFv linked to Hinge, CH2 and CH3 domains of human IgG1) and evaluated for binding to trimeric H5-TH04 or monomeric HA1 of H5-TH04 coated on an ELISA plate. The H5 scFv-Fcs recognize trimeric H5 but not HA1. An antibody raised against HA1 ("2A") recognized both. (b) Neutralization of H5-TH04-pseudotyped viruses (virus-like particles with HIV-1 only cores that display H5 on their surface). % neutralization at 2 concentrations is shown with standard deviation (s.d.) bars. The mAb 80R[18] was used as a negative control ("Ctrl."), (c-d) Neutralization of wild type H5-VN04 and H5-IN05 by the 10 scFv-Fcs at three concentrations using a plaque reduction assay. Results are consistent with those obtained from a microneutralization assay (data not shown).

DETAILED DESCRIPTION OF THE INVENTION

Figure 8:
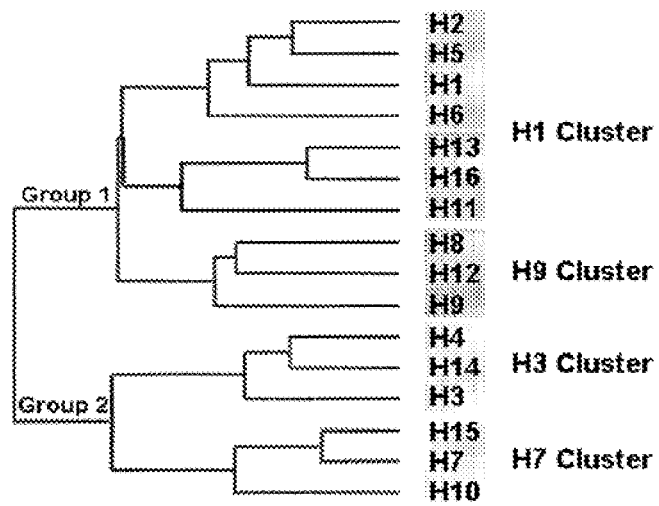
FIG. 8 shows phylogenetic relationships and sequence comparison among HA subtypes. Phylogenetic tree of the 16 HA subtypes of influenza A viruses based on amino-acid sequences. Four clusters of HA subtypes are (1) Cluster H1: H2, H5, H1, H6, H13, H16, and H11; (2) Cluster H9: H8, H12, and H9; (3) Cluster H3: H4, H14, and H3; and (4) Cluster H7: H15, H7, and H10. Within Cluster H1 are two subclusters: subcluster H1a: H2, H5, H1, and H6; and subcluster H1b: H13, H13, H16, and H11. The sequences used for analysis were: H1 (A/South Carolina/1/1918), H2 (A/Japan/305/1957), H3 (A/Aichi/2/1968), H4 (A/duck/Czechoslovakia/56), H5 (A/VietNam1203/2004), H6 (A/chicken/California/431/00), H7 (A/Netherland/219/03), H8 (A/Turkey/Ontario/6118/68), H9 (A/swine/HK/9/98), H10 (A/chicken/Germany/N49), H11 (A/duck/England/56), H12 (A/duck/Alberta/60/76), H13 (A/gull/Maryland/704/77), H14 (A/mallard/Astrakhan/263/1982), H15 (A/shearwater/West Australia/2576/79) and H16 (A/black-headed gull/Sweden/2/99).

The present invention relates to an immunogenic composition comprising peptide immunogens (natural or synthetic) capable of inducing antibodies against the hemagglutinin (HA) protein of influenza A virus. The present invention provides peptides that bind human monoclonal antibodies specific against the hemagglutinin (HA) protein of influenza A virus as well as antibodies specific against the hemagglutinin (HA) protein of influenza A virus.

Influenza virus remains a constant public health threat, owing to its ability to evade immune surveillance through rapid genetic drift and reassortment.

Influenza A is a negative-sense, single-stranded RNA virus, with an eight-segment genome encoding 10 proteins. It belongs to the family Orthomyxoviridae which includes the genera of influenza virus A, B and C as defined by the antigenicity of the nucleocapsid and matrix proteins. Generally, influenza A virus is associated with more severe disease in humans. Influenza A virus is further subtyped by two surface proteins, hemagglutinin (HA) which attaches the virion to the host cell for cell entry, and neuraminidase (NA) which facilitates the spread of the progeny virus by cleaving the host sialic acid attached to the progeny virus or cell surface.

There are 16 HA subtypes and 9 NA subtypes which make up all subtypes of influenza A viruses by various combinations of HA and NA. All combinations of the 16 HA and 9 NA virus subtypes are found in water fowl. Of the hundreds of strains of avian influenza A viruses, only four are known to have caused human infections: H5N1, H7N3, H7N7 and H9N2. In general, human infection with these viruses has resulted in mild symptoms and very little severe illness: there has been only one fatal case of pneumonia caused by H7N7. However, the exception is the highly pathogenic H5N1 virus, for which there is no natural immunity in humans. The infidelity of the RNA polymerase and the selective pressure of host immunity can lead to the accumulation of mutations and change in surface antigenicity of these proteins. This antigenic change is called antigenic drift. In addition, as a result of its segmented genome, shuffling of gene segments can occur if two different subtypes of influenza A virus infect the same cell. For example, if a human H3N2 virus and an avian H5N1 virus co-infect a human or other member of a mammalian species, such an event can produce a novel H5N2. This novel virus can then be efficiently transmitted from human to human because all of most of the gene segments come from the human virus. Such genetic reassortment would lead to a major antigen change, a so-called antigenic shift, which would mean that most of the global population would not have any neutralizing antibodies against the reassortment virus. Such a situation, coupled with the high mortality of influenza H5N1 pneumonia, is one of the most feared scenarios in the field of public health.

Influenza virus hemagglutinin (HA) is the most variable antigen of influenza virus, and is responsible for virus entry into cells. It is synthesized as a trimeric precursor polypeptide HA0 which is post-translationally cleaved to two polypeptides HA1 and HA2 linked by a single disulphide bond. The HA1 chain of HA is responsible for the attachment of virus to the cell surface. HA2 mediates the fusion of viral and cell membranes in endosomes, allowing the release of the ribonucleoprotein complex into the cytoplasm. In contrast to HA1, the HA2 molecule represents a relatively conserved part of HA.

Both the HA1 and HA2 chains of HA are immunogenic and antibodies reactive with both chains have been demonstrated after natural infection in humans. While antibodies specific to HA1 are mostly neutralizing, different mechanism of virus neutralization by HA1 specific Mabs in vitro have been described including blocking the receptor site on HA1, intracellular inhibition of virus-cell fusion, or simultaneous attachment inhibition and virus-cell fusion inhibition, depending on antibody concentration. Although less well studied, inhibition of cell fusion by anti-HA2 antibodies has been reported.

More than two decades ago, the HA molecule of the H3 subtype was characterized by sequencing the HA of antigenic drift variants and escape mutants, and the antigenic epitopes were mapped on the molecule's three-dimensional structure. Since then, the antigenic sites on H1, H2 and H5 of an avian pathogenic virus were mapped on the three-dimensional structures of H3. After the outbreak of H5N1 infection in humans in Hong Kong in 1997 and the isolation of H9N2 virus from human cases in 1999, the X-ray structures of both proteins were solved. However, antigenic drift of the 1997 swine isolate (A/Duck/Singapore/3/97) that was used to solve the structure, and more recently isolated highly pathogenic strains, is significant. Indeed, there are 28 minor changes and two potentially major changes between, the swine isolate (A/Duck/Singapore/3/97) and the HPA1 H5N1 strain (A/Vietnam1203/04).

Phylogenetic analyses of the H5 HA genes to the 2004-2005 outbreak have shown two different lineages of HA genes, termed clades 1 and 2. HPA1 H5N1 strain (A/Vietnam1203/04) is a member of clade 1. Viruses in each of these clades are distributed in non-overlapping geographic regions of Asia. The H5N1 viruses from Indochina are tightly clustered within clade 1, whereas H5N1 isolated from several surrounding countries are distinct from clade 1 isolates, and belong in a more divergent clade 2. Clade 1 viruses were isolated from humans and birds in Vietnam, Thailand and Cambodia but only from birds in Laos and Malaysia. The clade 2 viruses were found in viruses isolated exclusively from birds in China, Indonesia, Japan, and South Korea. The most recent epidemiologic studies analyzed 82 H5N1 viruses isolated from poultry throughout Indonesia and Vietnam, as well as 11 human isolates from southern Vietnam together with sequence data available in public databases, to address questions relevant to virus introduction, endemicity and evolution (Stevens, J. et al. Structure of the uncleaved human H1 hemagglutinin from the extinct 1918 influenza virus. Science 303. 1866-70 (2004)). Phylogenetic analysis showed that all viruses from Indonesia form a distinct sublineage of H5N1 genotype Z viruses, suggesting that this outbreak likely originated from a single introduction via spread throughout the country during the past two years. Continued virus activities in Indonesia were attributed to transmission via poultry movement within the country, rather than through repeated introductions by bird migration. Within Indonesia and Vietnam, H5N1 viruses have evolved over time into geographically distinct groups within each country.

Recently, the structure of HA from A/Vietnam1203/4 was solved. Comparison of its amino acid sequences with the HA genes from HPA1 2004 and 2005 isolates from clade 1 and 2 viruses identified 13 positions of antigenic variation that are mainly clustered around the receptor binding domain, while the rest are within the vestigual esterase domain. Regions of antigenic variation have been identified in H1 and H3 serotypes (FIG. 13A). For H1, these sites are designated Sa, Sb, Ca and Cb while for H3, sites are designated A, B, C and D. Escape mutants of H5 HAs can be clustered into three epitopes; site 1: an exposed loop (HA1 140-145) that overlaps antigenic sites A of H3 and Ca2 of H$^2$; site 2: HA1 residues 156 and 157 that corresponds to antigenic site B in H3 serotypes; and 3) HA1 129-133, which is restricted to the Sa site in H1 HAs and H9 serotypes. In the recent studies by Smith, detection of positive selection at the amino acid level indicated that eight residues in the HA proteins were under positive selection (FIG. 13B). These residues include five in antigenic sites A and E (positions 83, 86, 138, 140 and 141); two involved in receptor binding (positions 129 and 175); and positions 156 is a site for potential N-linked glycosylation that is near the receptor-binding site. The results further revealed that three residues in HA (Val 86, Ser 129 and Thr 156) were more frequently observed in human isolates than in chicken or duck isolates and likely represented early adaptation of H5N1 genotype Z to humans. Another important finding from these studies is that the phylogenetic differences between the Indonesian and Vietnamese sub-lineages was also reflected in significant differences in antigenic cross-reactivity between these two group of viruses. Specifically, viruses from Indonesia did not react to ferret antisera against A/Vietnam1203/04, and representative viruses from Vietnam did not react with ferret antisera against Indonesian viruses IDN/5/06 and Dk/IDN/MS/04. These findings are in agreement with earlier studies with immune human serum and human 1997 and 2003 H5N1 viruses that these strains were not only phylogenetically but also antigenically distinct. Thus, natural variation as well as escape mutants suggests that continued evolution of the virus should impact the decision on which strain(s) should be used for passive and active immunization.

High affinity, cross-subtype, broadly-neutralizing human anti-HA mAbs have been identified. Specifically, a human Ab phage display library and H5 hemagglutinin (HA) ectodomain was used to select ten neutralizing mAbs (nAbs) with a remarkably broad range among Group 1 influenza viruses, including the H5N1 "bird flu" and the H1N1 "Spanish flu" and "Swine flu" strains. These nAbs inhibit the post-attachment fusion process by recognizing a novel and highly conserved neutralizing epitope within the stem region at a point where key elements of the conformational change—the fusion peptide and the exposed surface of helix αA—are brought into close apposition. The crystal structure of one mAb (mAbF10) bound to H5N1 HA reveals that only the heavy chain inserts into a highly conserved pocket in the HA stem region, inhibiting the conformational changes required for membrane fusion. It has been discovered that nAbs targeting this pocket can provide broad protection against both seasonal and pandemic influenza A infections. The crystal structure further revealed that the epitope to which the F10 mAb is defined by amino acid residues 18, 38, 39, 40 and 291 of HA1 and 18, 19, 20, 21, 38, 41, 42, 45, 49, 52, 53, and 56 of HA2. This epitope is referred to herein as the F10 epitope. Structural and sequence analysis of all 16 HA subtypes points to the existence of only two variants of this epitope, corresponding to the two phylogenetic groupings of HA (Groups 1 and 2). This discovery indicates that a small cocktail of nAbs derived from a subset of each group can provide broad protection against both seasonal and pandemic influenza.

Remarkably, we repeatedly isolated nAbs that utilizes the same VH germline gene, IGHV1-69*01, and encodes a CDR3 loop containing a tyrosine at an equivalent position to Y102, from a non-immune library. This indicates that broad anti-HA cross-immunity pre-exists in the H5-naive population, possibly due to previous exposure to H1, and, for library donors born before 1968, H2 subtypes. The recurrent use of this germline VH segment, the commonality of the CDR3 tyrosine introduced through N insertion and/or germline D gene assembly, and the promiscuous use of VL genes by the discovered nAbs discovered indicate that the precursor frequency of rearranged VH segments that could recognize this epitope is significant. This indicates that with suitable exposure to the F10 epitope identified here, these broad-spectrum nAbs can be readily induced in vivo. These discoveries led to the disclosed simple solution to provide universal protection against virus subtypes in both groups.

Three unique anti-HA-1 scFvs were identified by sequencing analysis of the 58 HA-1 positive clones. These scFvs were designated as 38B and 1C. The VH and VL amino acid sequence of 2A is shown in Table 2.

Ten unique anti-HA0 scFvs were identified by sequencing analysis of the 97 HA0 positive clones. These scFvs were designated as 7, 8, 10, 17, 40, 66, 80, 88, 90, and 98. Six different VH and 10 different VL genes were revealed. Some scFvs shared the same VH gene. Five out of the six different VH genes belonged to the IGHV1-69 gene family. Three out of ten VL genes were kappa chain.

2A scFv is a moderate neutralizing antibody, 38B and 1C are non-neutralizing antibodies. Ten scFvs, 7, 8, 10, 17, 40, 66, 80, 88, 90, and 98 are potent neutralizing antibodies (Table 2). The nucleic acid and amino acid sequence of the neutralizing influenza antibodies are provided below:

TABLE 5A

| Antibody 2A Variable Region nucleic acid sequences |
|---|
| $V_H$ chain of 2A (SEQ ID NO: 41)<br>CAGGTGCAGCTGGTGCAGTCTGGGGCTGAGGTGAAGAAGCCTGGGTCCTC<br>GGTGAAGGTCTCCTGCAAGGCTTCTGGAGGCACCTTCAGTGACAATGCTA<br>TCAGCTGGGTGCGACAGGCCCCAGGACAAGGGCTTGAGTGGATGGGGGGC<br>ATCATTCCTATCTTTGGAAAACCAAACTACGCACAGAAGTTCCAGGGCAG<br>AGTCACGATTACTGCGGACGAATCCACGAGCACAGCCTACATGGACCTGA<br>GGAGCCTGAGATCTGAGGACACGGCCGTTTATTACTGTGCGAGAGATTCA<br>GACGCGTATTACTATGGTTCGGGGGGTATGGACGTCTGGGGCCAAGGCAC<br>CCTGGTCACCGTCTCCTCA |
| $V_L$ chain of 2A (SEQ ID NO: 44)<br>CTCCCTGTCCTCACTCAATCATCCTCTCCCTCTCCTTCCCTGGGATCCTC<br>GGTCAACCTCACCTGCACTGTGAGCAGTGGGCATAGTAACTACATCATCG<br>CATGGCATCAACAGCAGCCAGGGAAGGCCCCTCGGTACTTGATGAAGGTT<br>AATAGTGATGGCAGCCACACCAAGGGGGACGGGATCCCTGATCGCTTCTC<br>AGGCTCCAGCTCTGGGGCTGACCGCTACCTCACCATCTCCAACCTCCAGT<br>CTGAGGATGAGGCTAGTTATTTCTGTGAGACCTGGGACACTAAGATTCAT<br>GTCTTCGGAACTGGGACCAAGGTCTCCGTCCTCAG |

TABLE 5B

| Antibody 2A Variable Region amino acid sequences |
|---|
| $V_H$ chain of 2A (SEQ ID NO: 43)<br>QVQLVQSGAEVKKPGSSVKVSCKASGGTFSDNAISHVRQAPGQGLENMGG<br>IIPIFGKPNYAQKFQGRVTITADESTSTAYMDLRSLRSEDTAVYYCARDS<br>DAYYYGSGGMDVWGQGTLVTVSS |
| $V_L$ chain of 2A (SEQ ID NO: 45)<br>LPVLTQSSSASASLGSSVKLTGTLSSGHSNYIIAWHQQQPGKAPRYLMKV<br>NSDGSHTKGDGIPDRFSGSSSGADRYLTISNLQSEDEASYFCETWDTKIH<br>VFGTGTKVSVL |

TABLE 5C

| Antibody D7 Variable Region nucleic acid sequences |
|---|
| $V_H$ chain of D7 (SEQ ID NO: 46)<br>CAGGTGCAGCTGGTGCAGTCTGGGGCTGAGGTGAAGAAGCCTGGGTCCTC<br>GGTGAAGGTCTCCTGCAAGGCTCCTGGAGGTATCTTCAACACCAATGCTT<br>TCAGCTGGGTCCGACAGGCCCCTGGACAAGGTCTTGAGTGGGTGGGAGGG<br>GTCATCCCTTTGTTTCGAACAGCAAGCTACGCACAGAACGTCCAGGGCAG<br>AGTCACCATTACCGCGGACGAATCCACGAACACAGCCTACATGGAGCTTA<br>CCAGCCTGAGATCTGCGGACACGGCCGTGTATTACTGTGCGAGAAGTAGT<br>GGTTACCATTTTAGGAGTCACTTTGACTCCTGGGGCCTGGGAACCCTGGT<br>CACCGTCTCCTCA |
| $V_L$ chain of D7 (SEQ ID NO: 50)<br>AATTTTATGCTGACTCAGCCCCACTCTGTGTCGGCGTCTCCGGGGAAGAC<br>GGTGACCATCTCCTGCACCGGCAGCAGTGGCAACATTGCCGCCAACTATG<br>TGCAGTGGTACCAACAACGTCCGGGCAGTGCCCCCACTACTGTATCTATG<br>AGGATGACCGAAGACCCTCTGGGGTCCCTGATCGGTTCTCTGGCTCCATC<br>GACAGGTCCTCCAACTCTGCCTCCCTCACCATCTCAGGACTGAAGACTGA<br>GGACGAGGCTGACTACTACTGTCAGACTTATGATACCAACAATCATGCTG<br>TGTTCGGAGGAGGCACCCACCTGACCGTCCTC |

TABLE 5D

| Antibody H98 Variable Region nucleic acid sequences |
|---|
| $V_H$ chain of H98 (SEQ ID NO: 48)<br>CACCTGGAGCTCGTGCAATCTGGCCCTGACCTGAAGAAGGGTGGGTCCTC<br>GGTCAAGGTCTCCTGCAACGCTCCTCGAGGTATCTTCAACACCAATGCTT<br>TCAGCTGGGTCCGACAGGCCCCTGGACAAGGTCTTGAGTGGGTGGGAGGG<br>GTCATCCCTTTGTTTCGAACAGCAAGCTACGCACAGAACGTCCAGGGCAG<br>ACTCACCATTACCGCGCACGAATCCACGAACACAGCCTACATGGAGCTTA<br>CCAGCCTGAGATCTGCGGACACGGCCGTGTATTACTGTGCGAGAAGTAGT<br>GGTTACCATTTTAGGAGTCACTTTGACTCCTGGGGCCTGGGAACCCTGGT<br>CACCGTCTCCTCA |
| $V_L$ chain of H98 (SEQ ID NO: 52)<br>TCCTATGAGCTGACTCAGCCACCCTCAGCGTCTGGGAAACACGGGCAGAG<br>GGTCACCATCTCTTGTTCTGGAGGCACCTCCAACATCGGACGTAATCATG<br>TTAACTGGTACCAGCAACTCCCAGGAACGGCCCCCAAACTCCTCATCTAT<br>AGTAATGAACAGCGGCCCTCACGGGTCCCTGACCGATTCTCTGGCTCCAA<br>ATCTGGCACCTCCGCCTCCCTCGCCGTGACTGGCTCCAGTCTGAGGATGA<br>GGCTGATTATTACTGTGCATCATGGGATGACAACTTGAGTGGTTGGGTGT<br>TCGGCGGAGGGACCAAGCTGACCGTCCTA |

TABLE 5E

| Antibody D7 and H98 Variable Region chain amino acid sequences |
|---|
| $V_H$ chain of D7 and H98 (SEQ ID NO: 47)<br>QVQLVQSGAEVKKPGSSVKVSCKASGGIFNTNAFSWVRQAPGQGLEWVGG<br>VIPLFRTASYAQNVQGRVTITADESTNTAYMELTSLRSADTAVYYCARSS<br>GYHFRSHFDSWGLGTLVTVSS |
| $V_L$ chain of D7 (SEQ ID NO: 49)<br>NPMLTQPHSVSASPGKTVTISCTGSSGNIAANYVQWYQQRPGSAPTTVIY<br>HDDRRPSGVPDRFSGSIDRSSNSASLTISGLKTEDEADYYCQTYDTNNHA<br>VFGGGTHLTVL |
| $V_L$ chain of H98 (SEQ ID NO: 51)<br>SYELTQPPSASGKHGQRVTISCSGGTSNIGRNHVNWYQQLPGTAPKLLIY<br>SNEQRPSGVPDRFSGSKSGTSASLAVSGLQSEDEADYYCASWDDNLSGWV<br>FGGGTKLTVL |

TABLE 5F

| Antibody D8 Variable Region nucleic acid sequences |
|---|
| $V_H$ chain of D8 (SEQ ID NO: 54)<br>CAGGTGCAGCTGGTGCAGTCTGGGGCTGAGGTGAAGAAGCCTGGGTCCTC<br>GGTGAAGGTCTCCTGCAAGGCTTCTGGAGGCACCTTCAGCGCTTATGCTT<br>TCACCTGGGTGCGGCAGGCCCCTGGACAAGGGCTTGAGTGGATGGGAGGC<br>ATCACCGGAATGTTTGGCACAGCAAACTACGCACAGAAGTTCCAGGGCAG |

TABLE 5F-continued

Antibody D8 Variable Region nucleic acid sequences

AGTCACGATTACCGCGGACGAACTCACGAGCAGCCTACATGGAGTTGAGC
TCCCTGACATCTGAAGACACGGCCCTTTATTATTGTGCGAGAGGATTGTA
TTACTATGAGAGTAGTCTTGACTATTGGGGCCAGGGAACCCTGGTCACCG
TCTCCTCAG $V_L$ chain of D8 (SEQ ID NO: 58)
CAGTCTGTGCTGACTCAGCCACCCTCCGCGTCCGGGTCTCCTGGACAGTC
AGTCACCATCTCCTGCACTGGAACCAGCAGTGACGTTGGTGGTTATAACT
CTGTCTCCTGGTACCAACAGCACCCAGGCAAAGCCCCCAAACTCATGATT
TATGAGGTCACTAAGCGGCCCTCAGGGGTCCCTGATCGCTTCTCTGCCTC
CAAGTCTGGCAACACGGCCTCCCTGACCGTCTCTGGGCTCCAGGCTGAGG
ATGAGGCTGATTATTTCTGCTGCTCATATGCAGGCCACAGTGCTTATGTC
TTCGGAACTGGGACCAAGGTCACCGTCCTG

TABLE 1G

Antibody D80 Variable Region nucleic acid sequences $V_H$ chain of D80 (SEQ ID NO: 56)
CAGGTGCAGCTGGTGCAGTCTGGGGCTGAGGTGAAGAAGCCTGGGTCCTC
GGTGAAGGTCTCCTGCAGGGCTTCTGGAGGCACCTTCAGCGCTTATGCTT
TCACCTGGGTGCGGCAGGCCCCTGGACAAGGGCTTGAGTGGCTGGGAGGC
ATCACCGGAATGTTTGGCACACCAAACTACGCACACAAGTTCCAGGGCAG
ACTCACGATTACCCCCACGAACTCACCACCACACCCTACATGGAGTTGA
GCTCCCTGACATCTGAAGACACGGCCCTTTATTATTGTGCGAGAGGATTG
TATTACTATGAGAGTAGTCTTGACTATTGGGGCCAGGGAACCCTGGTCAC
CGTCTCCTCAG $V_K$ chain of D80 (SEQ ID NO: 60)
GAAATTGTGCTGACTCAGTCTCCAGGCACCCTGTCTTTGTCTCCAGGGGA
AAGAGCCACCCTCTCCTGCAGGGCCAGTCAGAGTCTTAGCAGCAAGTACT
TAGCCTGGTATCAGCAGAAACCTGGCCAGGCTCCCAGGCTCCTCATCTAT
GGTGCATCCAGCAGGGCCACTGGCATCCCAGACAGGTTCAGTGGCAGTGG
GTCTGGGACAGACTTCACCCTCACCATCAGTAGACTGGAGCCTGAAGATT
TTGCAGTGTATTCCTGTCAGCAGTATGATGGCGTACCTCGGACGTTCGGC
CAAGGGACCACGGTGGAAATCAAA

TABLE 5H

Antibody D8 and D80 Variable Region
chain amino acid sequences $V_H$ chain of D8 and D80 (SEQ ID NO: 53)
QVQLVQSGAEVKKPGSSVKVSCKASGGTFSAYAFTWVRQAPGQGLEWMGG
ITGMFGTANYAQKFQGRVTITADELTSTAYMELSSLTSEDTALYYCARGL
YYYESSLDYWGQGTLVTVSS $V_L$ chain of D8 (SEQ ID NO: 55)
QSVLTQPPSASGSPGQSVTISCTGTSSDVGGYNSVSWYQQHPGKAPKLMI
YRVTKRPSGVPDRFSASKSGNTASLTVSGLQAEDEADYFCCSYAGHSAYV
FGTGTKVTVL $V_K$ chain of D80 (SEQ ID NO: 57)
EIVLTQSPGTLSLSPGERATLSCRASQSLSSKYLAWYQQKPGQAPRLLIY
GASSRATGIPDRFSGSGSGTDFTLTISRLEPEDFAVYSCQQYDGVPRTFG
QGTTVEIK

TABLE 1I

Antibody F10 Variable Region nucleic acid sequences $V_H$ chain of F10 (SEQ ID NO: 62)
CAGGTGCAGCTGGTGCAGTCAGGGGCTGAGGTGAAGAAGCCTGGGTCCTC
GGTGAAGGTCTCCTGCACGTCCTCTGAAGTCACCTTCAGTAGTTTTGCTA
TCAGCTGGGTGCGACAGGCCCCTGGACAAGGGCTTGAGTGGCTGGGAGGG
ATCAGCCCTATGTTTGGAACACCTAATTACGCGCAGAAGTTCCAAGGCAG
AGTCACCATTACCGCGGACCAGTCCACGAGGACAGCCTACATGGACCTGA
GGAGCCTGAGATCTGAGGACACGGCCGTGTATTATTGTGCGAGATCTCCT
TCTTACATTTGTTCTGGTGGAACCTGCGTCTTTGACCATTGGGGCCAGGG
AACCCTGGTCACCGTCTCCTCA

TABLE 1I-continued

Antibody F10 Variable Region nucleic acid sequences $V_L$ chain of F10 (SEQ ID NO: 25)
CAGCCTGGGCTGACTCAGCCACCCTCGGTGTCCAAGGGCTTGAGACAGAC
CGCCACACTCACCTGCACTGGGAACAGCAACAATGTTGGCAACCAAGGAG
CAGCTTGGCTGCAGCAGCACCAGGGCCACCCTCCCAAACTCCTATCCTAC
AGGAATAATGACCGGCCCTCAGGGATCTCAGAGAGATTCTCTGCATCCAG
GTCAGGAAACACAGCCTCCCTGACCATTACTGGACTCCAGCCTGAGGACG
AGGCTGACTATTACTGCTCAACATGGGACAGCAGCCTCAGTGCTGTGGTA
TTCGGCGGAGGGACCAAGCTGACCGTCCTA

TABLE 5J

Antibody E90 Variable Region nucleic acid sequences $V_H$ chain of E90 (SEQ ID NO: 64)
CAGGTACAGCTGCAGCAGTCAGGGGCTGAGGTGAAGAAGCCTGGGTCCTC
GGTGAAGGTCTCCTGCACGTCCTCTGAAGTCACCTTCAGTAGTTTTGCTA
TCAGCTGGGTGCGACAGGCCCCTGGACAAGGGCTTGAGTGGCTGGGAGGG
ATCAGCCCTATGTTTGGAACACCTAATTACGCGCAGAAGTTCCAAGGCAG
AGTCACCATTACCGCGGACCAGTCCACGAGGACAGCCTACATGGACCTGA
GGAGCCTGAGATCTGAGGACACGGCCGTGTATTATTGTGCGAGATCTCCT
TCTTACATTTGTTCTGGTGGAACCTGCGTCTTTGACCATTGGGGCCAGGG
AACCCTGGTCACCGTCTCCTCA $V_L$ chain of E90 (SEQ ID NO: 27)
GACATCCAGATGACCCAGTCTCCATCCTCCCTGTCTGCATCTGTAGGAGA
CAGAGTCACCATCACTTGCCGGGCAAGTCAGAGCATTAGCAGCTATTTAA
ATTGGTATCAGCAGAAACCAGGGAAAGCCCCTAAGCTCCTGATCTATGCT
GCATCCAGTTTGCAAAGAGGGGTCCCATCAAGGTTCAGTGGCAGTGGATC
TGGGACAGACTTCACTCTCACCATTAGCAGCCTGCAGCCTGAAGATTTTG
CAGTGTATTACTGTCAGCAGTATGATAGTTCACCGTACACTTTTGGCCAG
GGGACCAAGGTAGAGATCAAA

TABLE 1K

Antibody F10 and E90 Variable Region
amino acid sequences $V_H$ chain of F10 and E90 (SEQ ID NO: 59)
QQLVQSGAEVKKPGSSVKVSCTSSEVTFSSFAISWVRQAPGQGLEWLGGI
SPMFGTPNYAQKFQGRVTITADQSTRTAYMDLRSLRSEDTAVYYCARSPS
YICSGGTCVFDHWGQGTLVTVSS $V_L$ chain of F10 (SEQ ID NO: 61)
QPGLTQPPSVSKGLRQTATLTCTGNSNNVGNQGAAWLQQHCGHPPKLLSY
RNNDRPSGISERFSASRSGNTASLTITGLQPEDEADYYCSTWDSSLSAVV
FGGGTKLTVL $V_L$ chain of E90 (SEQ ID NO: 63)
DIQMTQSPSSLSASVGDRVTITCRASQSISSYLNWYQQKPGKAPKLLIYA
ASSLQRGVPSRFSGSGSGTDPTLTISSLQPEDFAVYYCQQYDSSPYTFGQ
GTKVEIK

TABLE 5L

Antibody G17 Variable Region nucleic acid sequences $V_H$ chain of G17 (SEQ ID NO: 29)
CAGGTGCAGCTGGTGCAATCTGGGGCTGAAGTGAAGAAGCCTGGGGCCTC
AGTGAAGGTCTCCTGCAAGACTTCTGGAGTCACCTTCAGCAGCTATGCTA
TCAGTTGGGTGCGACAGGCCCCTGGACAAGGGCTTGAGTGGATGGGAGGG
ATCATCGGTGTCTTTGGTGTACCAAAGTACGCGCAGAACTTCCAGGGCAG
AGTCACAATTACCGCGGACAAACCGACGAGTACAGTCTACATGGAGCTGA
ACAGCCTGAGAGCTGAGGACACGGCCGTGTATTACTGTGCGAGAGAGCCC
GGGTACACGTAGGAAAGAATGGTTTTGATGTCTGGGGCCAAGGGACAAT
GGTCACCGTCTCTTCA $V_L$ chain of G17 (SEQ ID NO: 31)
TCCTATGAGCTGACTCAGCCACCCTCGGTGTCCAAGGGCTTGAGACAGAC
CGCCATACTCACCTGCACTGGAGACAGCAACAATGTTGGCACCAAGGTA
CAGCTTGGCTGCAACAACACCAGGGCCACCCTCCCAAACTCCTATCCTAC
AGGAATGGCAACCGGCCCTCAGGGATCTCAGAGAGATTCTCTGCATCCAG

TABLE 5L-continued

Antibody G17 Variable Region nucleic acid sequences

GTCAGGAAATACAGCCTCCCTGACCATTATTGACTCCAGCCTGAGGACGA
GGCTGACTACTACTGCTCAGTATGGGACAGCAGCCTCAGTGCCTGGGTGT
TCGGCGGACCAAGCTGACCGTCCTA

TABLE 5M

Antibody G17 Variable Region amino acid sequences

V$_H$ chain of G17 (SEQ ID NO: 24)
QVQLVQSGAEVKKPGASVKVSCKTSGVTFSSYAISWVRQAPGQGLEWMGG
IIGVFGVPKYAQNFQGRVTITADKPTSTVYMELNSLRAEDTAVYYCAREP
GYYVGKNGFDVWGQGTMVTVSS V$_L$ chain of G17 (SEQ ID NO: 26)
SYELTQPPSVSKGLRQTAILTCTGDSNNVGHQGTAWLQQHQGHPPKLLSY
RNGNRPSGISERFSSRSGNTASLTIIGLQPEDEADYYCSVWDSSLSAWVF
GGGTKLTVL

TABLE 5N

Antibody H40 Variable Region nucleic acid sequences

V$_H$ chain of H40 (SEQ ID NO: 33)
CAGGTGCAGCTGGTGCAGTCTGGGGCTGAGGTGAGGAAGCCTGCGGCCTC
AGTGAAGGTCTCATGTAAGGCTTCTGGATACACCTTCACCGGTTATTATA
TTCACTGGGTGCGACAGGCCCCTGGACAAGGACTTGAGTGGATGGGTTGG
ATCAACCCTATGACTGGTGGCACAAACTATGCACAGAAGTTTCAGGTCTG
GGTCACCATGACCCGGGACACGTCCATCAACACAGCCTACATGGAGGTGA
GCAGGCTGACATCTGACGACACGGCCGTGTATTACTGTGCGAGGGGGCT
TCCGTATTACGATATTTTGACTGGCAGCCCGAGGCTCTTGATATCTGGGG
CCTCGGGACCACGGTCACCGTCTCCTCA V$_L$ chain of H40 (SEQ ID NO: 35)
CAGCCTGTGCTGACTCAGCCACCCTCGGTGTCAGTGGCCCCAGGACAGAC
GGCCAGCATTCCTGTGGGGGGAACAACATTGGACGCTACCAGTGTACAC
TGGTACCAACAAAAGCCGGGCCAGGCCCCCCTCTTGGTCATTTATGACGA
TAAAGACCGGCCCTCAGGGATCCCTGAGCGATTCTCTGGCGCCAACTCTG
GGAGCACGGCCACCCTGACAATCAGCAGGGTCGAAGCCGGGATGAGGGC
GACTACTACTGTCAGGTGTGGGATAGTGGTAATGATCGTCCGCTGTTCGG
CGGAGGGACCAAGCTGACCGTCCTA

TABLE 5O

Antibody H40 Variable Region amino acid sequences

V$_H$ chain of H40 (SEQ ID NO: 28)
QVQLVQSGAEVRKPGASVKVSCKASGYTFTGYYIHWVRQAPGQGLEWMGW
INPMTGGTNYAQKFQVWVTMTRDTSINTAYMEVSRLTSDDTAVYYCARGA
SVLRYFDWQPEALDIWGLGTTVTVSS V$_L$ chain of H40 (SEQ ID NO: 30)
QPVLTQPPSVSVAPGQTASIPCGGNNIGGYSVHWYQQKPGQAPLLVIYDD
KDRPSGIPERFSGANSGSTATLTISRVEAGDEGDYYCQVWDSGNDRPLFG
GGTKLTVL

TABLE 5P

Antibody A66 Variable Region nucleic acid sequences

V$_H$ chain of A66 (SEQ ID NO: 37)
CAGGTGCAGCTGGTGCAGTCTGGGGCTGAAGTGAAGAAGCCTGGCTCCTC
GGTGAAGGTTTCCTGCAAGGCTTCTGGAGGCCCCTTCAGCATGACTGCTT
TCACCTGGCTGCGACAGGCCCCTGGACAAGGGCTTGAGTGGATGGGTGG
ATCAGCCCTATCTTTCGTACACCGAAGTACGCACAGAAGTTCCAGGGCAG
AGTCACGATTACCGCGGACGAATCCACGAACACAGCCAACATGGAGCTGA
CCAGCCTGAAATCTGAGGACACGGCCGTGTATTACTGTGCGAGAACCCTT
TCCTCCTACCAACCGAATAATGATGCTTTTGCTATCTGGGGCCAAGGGAC
AATGGTCACCGTCTCTTCA

TABLE 5P-continued

Antibody A66 Variable Region nucleic acid sequences

V$_K$ chain of A66 (SEQ ID NO: 39)
GAAATTGTGTTGACGCAGTCTCCAGCCACCCTGTCTTTGTCTCCAGGGGA
AAGAGCCACCCTCTCCTGCAGGGCCAGTCACACTCTTACCACCTACTTAC
CCTGGTACCAACAGAAACCTCCCCACCCTCCCACCCTCCTCATCTATGAT
GCATCCAACAGGGCCACTGGCATCCCAGCCAGGTTCAGTGGCAGTGGGTC
TGGGACAGACTTCACTCTCACCATCAGCAGACTGGAGCCTGAAGATTTTG
CAGTCTATTTCTGTCAGCAGTATGGTAGCTCACCTCAATTCGGCCAAGGG
ACACGACTGGAGATTAAA

TABLE 5Q

Antibody A66 Variable Region amino acid sequences

V$_H$ chain of A66 (SEQ ID NO: 32)
QVQLVQSGAEVKKPGSSVKVSCKASGGPFSMTAFTWLRQAPGQGLEWMGG
ISPIFRTPKYAQKFQGRVTITADESTNTANMELTSLKSEDTAVYYCARTL
SSYQPNNDAFAIWGQGTMVTVSS V$_K$ chain of A66 (SEQ ID NO: 34)
EIVLTQSPATLSLSPGERATLSCRASQSVSSYLAWYQQKPGQAPRLLIYD
ASNRATGIPARFSGSGSGTDFTLTISRLEPEDFAVYFCQQYGSSPQFGQG
TRLEIK

TABLE 5R

Antibody E88 Variable Region nucleic acid sequences

V$_H$ chain of E88 (SEQ ID NO: 40)
CAGGTGCAGCTGGTGCAGTCTGGGGCTGAAGTGAAGAAGCCTGGCTCCTC
GGTGAAGGTTTCCTGCAAGGCTTCTGGAGGCCCCTTCAGCATGACTGCTT
TCACCTGGCTGCGACAGGCCCCTGGACAAGGGCTTGAGTGGATGGGTGGG
ATCAGCCCTATCTTTCGTACACCGAAGTACGCACAGAAGTTCCAGGGCAG
AGTCACGATTACCGCGGACGAATCCACGAACACAGCCAACATGGAGCTGA
CCAGCCTGAAATCTGAGGACACGGCCGTGTATTACTGTGCGAGAACCCTT
TCCTCCTACCAACCGAATAATGATGCTTTTGCTATCTGGGGCCAAGGGAC
AATGGTCACCGTCTCTTCA V$_L$ chain of E88 (SEQ ID NO: 42)
CTGCCTGTGCTGACTCAGCCACCCTCAGCGTCTGGGACCCCCGGGCAGAG
GGTCACCATCTCTTGTTCTGGAAGCAGCTCCAACATCGGAAGTAATACTG
TAAACTGGTACCAGCAGCTCCCAGGAACGCCCCCAAACTCCTCATCTAT
AGTAATAATCAGCGGCCCTCAGGGGTCCCTGACCGATTCTCTGGCTCCAG
GTCAGGCACCTCAGCCTCCCTGGCCATCATTGGACTCCGGCCTGAGGATG
AAGCTGATTATTACTGTCAGTCGTATGACAGCAGGCTCAGTGCTTCTCTC
TTCGGAACTGGGACCACGGTCACCGTCCTC

TABLE 5S

Antibody E88 Variable Region amino acid sequences

V$_H$ chain of E88 (SEQ ID NO: 36)
QVQLVQSGAEVKKPGSSVKVSCKASGGPFSMTAFTWLRQAPGQGLEWMGG
ISPIFRTPKYAQKFQGRVTITADESTNTANMELTSLKSEDTAVYYCARTL
SSYQPNNDAFAIWGQGTMVTVSS V$_L$ chain of E88 (SEQ ID NO: 38)
LPVLTQPPSASGTPGQRVTISCSGSSSNIGSNTVNWYQQLPGTAPKLLIY
SNNQRPSGVPDKFSGSRSGTSASLAIIGLRPEDEADYYCQSYDSRLSASL
FGTGTTVTVL The amino acid sequences of the heavy and light chain complementary determining regions of the neutralizing influenza antibodies are shown in Tables 2 and 6. Sequences in Table 6 are, from left to right then top to bottom, SEQ ID NO:65-124.

TABLE 6

| Antibody | CDR1 | CDR2 | CDR3 |
|---|---|---|---|
| CONSENSUS | SYAFS | GHPMFGTPNYAQKFQG | SSGYYYG GGFDV |
| D7/H98VH | TNAFS | GVIPLFRTASYAQNVQG | SSGYHFGRSHFDS |
| D8/D80VH | AYAFT | GIIGMFGTANYAQKFQG | GLYYYESSLDY |
| F10/90VH | SFAIS | GISPMFGTPNYAQKFQG | SPSYICSGGTCVFDH |
| G17VH | SYAIS | GIIGVFGVPKYAQKFQG | EPGYYVGKNGFDV |
| H40VH | GYYIH | WINPMTGGTNYAQKFQV | GASVLRYFDWQPEALDI |
| A66VH | MTAFT | GISPIFRTPKYAQKFQG | TLSSYQPNNDAFAI |
| 2AVH | DNAIS | GIIPIFGKPNYAQKFQG | DSDAYYYGSGGMDV |
| CONSENSUS | TGSSSNIGNYVA | SNSDRPS | QSYDSLSAYV |
| D7VL | TGSSSNIAANYVQ | EDDRRPS | QSYDTNNHAV |
| DD8VL | TGTSSDVGGYNSVS | EVTKRPS | CSYAGHSAYV |
| F10VL | TGNSNNVGNQGAA | RNNDRPS | STWDSSLSAVV |
| G17VH | TGDSNNVGHQGTA | RNGNRPS | SVWDSSLSAWV |
| H40VH | GGNNIGGYSVH | DDKDRPS | QVWDSGNDRPL |
| A66VH | RASQSVSSYLA | DASNRAT | QQYGSSPQV |
| D80VL | RASQSLSSKYLA | GASSRAT | QQYDGVPRT |
| E88VL | TGSSSNIGNYVA | SNNQRPS | QSYDSRLSASL |
| E90VK | SGSSSNIGSNTVN | AASSLQR | QQYDSSPYT |
| H98VL | RASQSISSYLN | SNEQRPS | ASWDDNLSGWV |
| 2AVL | TLSSGHSNYIIA | VNSDGSHTKGD | ETWDTKIHV |

Those skilled in the art will recognize that additional scFvs and monoclonal antibodies having different binding affinities can also be therapeutically effective. For example, antibodies and scFvs having binding affinities ranging from about 1 pM to about 200 mM can also be therapeutically effective.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an antibody is disclosed and discussed and a number of modifications that can be made to a number of molecules including the antibody are discussed, each and every combination and permutation of antibody and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, md C-E are specifically contemplated and should be considered disclosed from disclosure of A, B and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Disclosed are antibodies that bind to the stem region of influenza hemagglutinin in the neutral pH conformation. Such antibodies can be referred to herein as HA stem antibodies. For example, disclosed are antibodies that bind the epitope of influenza hemagglutinin bound by antibody F10. For example, disclosed are antibodies that bind the epitope of influenza hemagglutinin in the neutral pH conformation defined by amino acid residues 18, 38, 39, 40 and 291 of HA1 and 18, 19, 20, 21, 38, 41, 42, 45, 49, 52, 53, and 56 of HA2. For example, disclosed are antibodies that bind the epitope of influenza hemagglutinin in the neutral pH conformation defined by amino acid residues 17, 18, 38, 39, 40 and 291 of HA1 and 18, 19, 20, 21, 38, 41, 42, 45, 49, 52, 53, 56, and 111 of HA2. For example, disclosed are antibodies that bind to every subtype within an influenza virus group.

In some forms, the antibody can compete with antibody F10 for binding to hemagglutinin. In some forms, the antibody can have a VH CDR2 sequence that is the same as the VH CDR2 sequence of antibody D7, D8, F10, G17, H40 or A66 or of the consensus VH sequence SEQ ID NO:1. In some forms, the antibody can have a VH CDR3 sequence that is the same as the VH CDR3 sequence of antibody D7, D8, F10, G17, H40 or A66 or of the consensus VH sequence SEQ ID NO:1. In some forms, the antibody can have a VH CDR1 sequence that is the same as the VH CDR1 sequence of antibody D7, D8, F10, G17, H40 or A66 or of the consensus VH sequence SEQ ID NO:1. In some forms, the antibody can have a VH sequence that is the same as the VH sequence of antibody D7, D8, F10, G17, H40 or A66 or of the consensus VH sequence SEQ ID NO:1. In some forms, the antibody can have a VL sequence that is the same as the VL sequence of antibody D7, D8, F10, G17, H40, A66, D80, E88, E90, or H98 or of the consensus VL sequence SEQ ID NO:2. In some forms, the antibody can have any combination of the VH FR1, VH CDR1, VH FR2, VH CDR2, VH FR3, VH CDR3, and VH FR4 sequences of antibodies D7, D8, F10, G17, H40 and A66 and the consensus VH sequence SEQ ID NO:1, and any combination of the VL FR1, VL CDR1, VL FR2, VL CDR2, VL FR3, VL CDR3, and VL FR4 sequences of antibodies D7, D8, F10, G17, H40, A66, D80, E88, E90, and H98 and the consensus VL sequence SEQ ID NO:2. In some forms, the antibody can prevent or inhibit virus-host membrane fusion. In some forms, the antibody can prevent or inhibit cell fusion mediated by cell surface-expressed influenza hemagglutinin.

Also disclosed are antibodies identified or produced in disclosed methods. For example, disclosed is a method, the method comprising screening antibodies reactive to hemagglutinin for binding to hemagglutinin immobilized on a surface, thereby identifying antibodies of interest. For example, disclosed is a method comprising screening antibodies reactive to hemagglutinin for binding to the stem region of influenza hemagglutinin in the neutral pH conformation in isolation from the head region of hemagglutinin, thereby identifying antibodies of interest. For example, disclosed is a method comprising screening antibodies reactive to hemagglutinin for binding to influenza hemagglutinin in the neutral pH conformation in isolation from other components of influenza virus, wherein the head region of the hemagglutinin is modified to reduce the antigenicity of the head region, thereby identifying antibodies of interest.

Also disclosed are different forms of hemagglutinins. These forms of hemagglutinins are useful in the preparation of vaccines for influenza. For example, disclosed is the stem region of influenza hemagglutinin in the neutral pH conformation in isolation from other components of influenza virus. For example, disclosed is the stem region of influenza hemagglutinin in the neutral pH conformation in isolation from the head region of hemagglutinin. For example, disclosed is influenza hemagglutinin in the neutral pH conformation in isolation from other components of influenza virus, wherein the head region of the hemagglutinin is modified to reduce the antigenicity of the head region. In some forms, the head region of the hemagglutinin can be modified by removing or replacing glycosylation sites. In some forms, the head region of the hemagglutinin can be modified by adding glycosylation sites. In some forms, the head region of the hemagglutinin can be modified by removing all or a portion of the head region. Also disclosed is influenza hemagglutinin bound to s surface, solid support or substrate.

In some forms, the disclosed antibodies and disclosed hemagglutinins can produce an immune reaction in a subject, i.e. immunogenic. The disclosed antibodies and disclosed hemagglutinins are formulated in compositions suitable for the use as a vaccine. For example, the disclosed hemagglutinins are used for active immunization of a subject to induce an immune reaction in a subject. Alternatively, the disclosed antibodies are used for the passive immunization of a subject to provide immediate protection from an influenza infection.

For example, in some forms, the subject can produce an immune response that prevents or reduces the severity of an influenza infection. In some forms, the immune response can be reactive to influenza viruses within a subtype. In some forms, the immune response can be reactive to influenza viruses in each subtype within a cluster. In some forms, the immune response can be reactive to influenza viruses in each cluster within a group. In some forms, the immune response can be reactive to all influenza viruses in each subtype within a group. In some forms, the immune response can be reactive to influenza viruses within group 1.

In some forms, the antibodies can be identified as competing with antibody F10 for binding to hemagglutinin, thereby identifying F10-competing antibodies. In some forms, the hemagglutinin can be hemagglutinin from a group 2 influenza virus. In some forms, the hemagglutinin can be hemagglutinin from a group 1 influenza virus. Also disclosed are antibodies produced by the disclosed methods. Also disclosed are antibodies identified by the disclosed methods.

A. Antibodies

Disclosed are antibodies that bind to the stem region of influenza hemagglutinin in the neutral pH conformation. Such antibodies can be referred to herein as HA stem antibodies. For example, disclosed are antibodies that bind the epitope of influenza hemagglutinin bound by antibody F10. For example, disclosed are antibodies that bind the epitope of influenza hemagglutinin in the neutral pH conformation defined by amino acid residues 18, 38, 39, 40 and 291 of HA1 and 18, 19, 20, 21, 38, 41, 42, 45, 49, 52, 53, and 56 of HA2. For example, disclosed are antibodies that bind the epitope of influenza hemagglutinin in the neutral pH conformation defined by amino acid residues 17, 18, 38, 39, 40 and 291 of HA1 and 18, 19, 20, 21, 38, 41, 42, 45, 49, 52, 53, 56, and 111 of HA2. For example, disclosed are antibodies that bind to every subtype within an influenza virus group. Examples of HA stem antibodies include antibodies D7, D8, F10, G17, H40, A66, H98, D80, E90, and E8.

The terms "antibody" and "antibodies" are used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, and can be chosen for their ability to interact with hemagglutinin. Thus, antibody refers to immunoglobulin molecules and immunologically active portions of immunoglobulin (Ig) molecules, i.e., molecules that contain an antigen binding site that specifically binds (immunoreacts with) an antigen. Antibodies include, but are not limited to, polyclonal, monoclonal, chimeric, dAb (domain antibody), single chain, Fab, Fab' and F(ab')2 fragments, scFvs, and Fab expression libraries.

The antibodies can be tested for their desired activity using the in vitro assays described herein, or by analogous methods, after which their in vivo therapeutic and/or prophylactic activities are tested according to known clinical testing methods.

The disclosed antibodies or antigen-binding fragments, variants, or derivatives thereof include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to HA stem antibodies disclosed herein). ScFv molecules are known in the art and are described, e.g., in U.S. Pat. No. 5,892,019. Unless the context clearly indicates otherwise, the terms "antibody" and "antibodies" include intact immunoglobulin molecules and any epitope- or antigen-binding fragments, variants, or derivatives thereof described herein or known in the art. The disclosed immunoglobulin or antibody molecules can be of any type (e.g., IgG, IgE, IgM, IgD, IgA, and IgY), class (e.g., IgG1 IgG2, IgG3, IgG4, IgA1 and IgA2) or subclass of immunoglobulin.

A single chain Fv ("scFv") polypeptide molecule is a covalently linked VH::VL heterodimer, which can be expressed from a gene fusion including VH- and VL-encoding genes linked by a peptide-encoding linker. (See Huston, et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies, (See Barbas et al., Proc. Natl. Acad. Sci. USA 89:9339-43 (1992); Zebedee et al., Proc. Natl. Acad. Sci. USA 89:3175-79 (1992)).

The term "antigen binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Various procedures known within the art can be used for the production of polyclonal or monoclonal antibodies directed against a protein (such as the disclosed hemagglutinin compositions), or against derivatives, fragments, analogs homology or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, can be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The terms "monoclonal antibody," "mAb" and "monoclonal antibody composition" as used herein refers to an antibody obtained from a substantially homogeneous population of antibodies, i.e., the individual antibodies within the population are identical except for possible naturally occurring mutations that may be present in a small subset of the antibody molecules. Thus, for example, "monoclonal antibody" can refer to a population of antibody molecules that contain only one molecular species of antibody molecule consisting of a unique light chain gene product and a unique heavy chain gene product. In particular, the complementarity determining regions (CDRs) of the monoclonal antibody can be identical in all the molecules of the population. mAbs contain an antigen binding site capable of immunoreacting with a particular epitope of the antigen characterized by a unique binding affinity for it.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired activity (See, U.S. Pat. No. 4,816, 567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes can be immunized in vitro. For example, monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent.

Cells expressing cell surface localized versions of these proteins can be used to immunize mice, rats or other species. Traditionally, the generation of monoclonal antibodies has depended on the availability of purified protein or peptides for use as the immunogen. More recently DNA based immunizations have been used to elicit strong immune responses and generate monoclonal antibodies. In this approach, DNA-based immunization can be used, wherein DNA encoding the epitope or antigen of interest (hemagglutinin, for example) expressed either alone or as a fusion protein with human IgG1 or an epitope tag is injected into the host animal according to methods known in the art (e.g., Kilpatrick K E, et al. Hybridoma, 1998 December; 17(6): 569-76; Kilpatrick K E et al. Hybridoma. 2000 August; 19(4):297-302, which, are incorporated herein by referenced in full for the methods of antibody production) and as described in the examples. In particular, a hemagglutinin composition comprising the stem region in properly folded form can be used.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing the epitope or antigen of interest (hemagglutinin, for example) as fusion proteins with a signal sequence fragment. The antigen can be produced by inserting a gene fragment in-frame between the signal sequence and the mature protein domain of hemagglutinin (or an engineered portion of hemagglutinin) nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes can then be fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells can be cultured in a suitable culture medium that can, for example, contain one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Useful immortalized cell lines are those that fuse efficiently, support stable high level expression of antibody by the selected antibody-producing cells, and are sensitive to a medium such as HAT medium. An example of useful immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against hemagglutinin stem region. In some forms, the binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988). Useful techniques for identifying and characterizing the binding of HA stem antibodies are described in the examples. For example, antibodies can be screened for binding to hemagglutinin bound to or immobilized on a surface.

After the desired hybridoma cells are identified, the clones can be subcloned by limiting dilation or FACS sorting procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies can also be made by recombinant DNA methods, such as those described in U.S. Pat. No 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al. The antibodies produced can be screened for antibodies having the desired binding ability in the ways described for identifying monoclonal antibodies discussed above, described elsewhere herein, and in ways known to those of skill in the art. The examples describe a useful way of producing and identifying HA stem antibodies.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment should possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment (Zoller, M. J. *Curr. Opin. Biotechnol.* 3:348-354, 1992).

The immunizing agent can include the protein antigen, a fragment thereof or a fusion protein thereof. Generally, either peripheral blood lymphocytes can be used if cells of human origin are desired, or spleen cells or lymph node cells can be used if non-human mammalian sources are desired. The lymphocytes can then be fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that can contain one or more substances that inhibit the growth or survival of the infused, immortalized cells. For example, if the parental cells lack the enzyme hypoxanthine guanine phosphoribosyl transferase (HGPRT or HPRT), the culture medium for the hybridomas can include hypoxanthine, aminopterin, and thymidine ("HAT medium"), which substances prevent the growth of HGPRT-deficient cells.

Useful immortalized cell lines include those that fuse efficiently, support stable high level expression of antibody by the selected antibody-producing cells, and are sensitive to a medium such as HAT medium. Useful immortalized cell lines include murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by, for example, the Scatchard analysis of Munson and Pollard, Anal. Biochem., 107:220 (1980). Moreover, in therapeutic applications of the disclosed antibodies, it is useful to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods such as those described in U.S. Pat. No. 4,816,567. DNA encoding the disclosed monoclonal antibodies can be readily isolated and sequenced using conventional procedures (e.g., by using oligonucleotide probes that are capable of binding specifically to genes encoding the heavy and light chains of murine antibodies). The disclosed hybridoma cells can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody, or can be substituted for the variable domains of one antigen-combining site of an antibody to create a chimeric bivalent antibody.

Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies can be prepared by, for example, using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies can be utilized and can be produced by using human hybridomas (see Cote, et al., 1983, Proc Natl Acad Sci USA 80: 2026-2030) or by transforming human B-cells with Epstein Bart Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al. Nature Biotechnology 14, 845-51 (1996); Neuberger, Nature Biotechnology 14, 826 (1996); and Lonberg and Huszar, Intern. Rev. Immunol. 13 65-93 (1995).

Human antibodies can additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes can be incorporated, for example, using yeast artificial chromosomes containing the requisite human DNA segments. An animal which provides all the desired modifications can then be obtained as progeny by crossbreeding intermediate transgenic animals containing fewer than the full complement of the modifications. A useful form of such a nonhuman animal include, for example, a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

As another example, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above. These can include vectors, liposomes, naked DNA, adjuvant-assisted DNA, gene gun, catheters, etc. Vectors can include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Useful vectors include viral vectors, fusion proteins and chemical conjugates. Retroviral vectors include moloney murine leukemia viruses. DNA viral vectors are an example. These vectors include pox vectors such as orthopox or avipox vectors, herpesvirus vectors such as a herpes simplex I virus (HSV) vector (see (Geller, A. I. et al., J. Neurochem, (64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G., et al., Nat. Genet. 8:148 (1994).

Pox viral vectors introduce the gene into the cells cytoplasm. A vipox virus vectors result in only a short term expression of the nucleic acid. Adenovirus vectors, adeno-associated virus vectors and herpes simplex virus (HSV) vectors can be used for introducing the nucleic acid into neural cells. The adenovirus vector results in a shorter term expression (about 2 months) than adeno-associated virus (about 4 months), which in turn is shorter than HSV vectors. The particular vector chosen can depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and can be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of an influenza virus in a sample. The antibody can also be used to try to bind to and disrupt influenza virus cell membrane fusion.

Techniques can be adapted for the production of single-chain antibodies specific to the disclosed antigenic protein (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen can be produced by techniques known in the art including, but not limited to: (i) an $F_{(ab')}2$ fragment produced by pepsin digestion of an antibody molecule; (ii) an $F_{ab}$ fragment generated by reducing the disulfide bridges of an $F_{(ab')}2$ fragment; (iii) an $F_{ab}$ fragment generated by the treatment of the antibody molecule with papain and a reducing agent and (iv) $F_v$ fragments.

Also disclosed are heteroconjugate antibodies. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the disclosed antibody with respect to effector function, so as to enhance, e.g., the effectiveness of the antibody in treating influenza. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC) (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities (See Stevenson et. al., Anti-Cancer Drug Design, 3: 219-230 (1989)).

Also disclosed are immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain, (from *Pseudomonoas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent can be made using a variety of bifunctional protein-coupling agents such as N-succinimidyl-3-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody (See WO94/11026).

Those of ordinary skill in the art will recognize that a large variety of possible moieties can be coupled to the disclosed antibodies or to other molecules (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling can be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. Covalent binding is also useful. Covalent binding can be achieved either by direct condensation of existing side chains or by the incorporation of external bridging molecules. Many bivalent or polyvalent linking agents are useful in coupling protein molecules, such as the disclosed antibodies, to other molecules. For example, representative coupling agents can include organic compounds such as thioesters, carbodiimides, succinimide esters, diisocyanates, glutaraldehyde diazobenzenes and hexamethylene diamines. This listing is not intended to be exhaustive of the various classes of coupling agents known in the art but, rather, is exemplary of the more common coupling agents (See Killen and Lindstrom, Jour. Immun. 133:1335-2549 (1984); Jansen et al., Immunological Reviews 62:185-216 (1982); and Vitetta et al., Science 238:1098 (1987)). Examples of useful linkers are described in the literature (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Useful linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionmamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co., Cat. #2165-G); and (v) sulfo-NHS (H-hydroxysulfo-succinimide: Pierce Chem. Co., Cat. #24510) conjugated to EDC.

The linkers described above can contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody can be prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes can be extruded through filters of defined pore size to yield liposomes with the desired diameter. Fab' fragments of the disclosed antibodies can be conjugated to the liposomes as described in Martin et al., J. Biol. Chem., 257: 286-288 (1982) via a disulfide-interchange reaction.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

In general, antibody molecules obtained from humans can relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain can be a kappa chain or a lambda chain.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these can be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

In the context of antibodies, the term, "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of the β-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

The term "antibody" as used herein is also meant to include intact molecules as well as fragments thereof, such as, for example, Fab and $F(ab')_2$, which are capable of binding the epitope determinant.

As used herein, the term "antibody" encompasses chimeric antibodies and hybrid antibodies, with dual or multiple antigen or epitope specificities, and fragments, such as $F(ab')_2$, Fab', Fab and the like, including hybrid fragments. Thus, fragments of the antibodies that retain the ability to bind their specific antigens are provided. For example, fragments of antibodies which maintain hemagglutinin binding activity, such as to the hemagglutinin stem region, are included within the meaning of the term "antibody." Such antibodies and fragments can be made by techniques known in the art and can be screened for specificity and activity according to the methods set forth in the Examples and in general methods for producing antibodies and screening antibodies for specificity and activity (See Harlow and Lane, Antibodies, A Laboratory Manual. Cold Spring Harbor Publications, New York, (1988)).

Also included within the meaning of "antibody" are conjugates of antibody fragments and antigen binding proteins (single chain antibodies) as described, for example, in U.S. Pat. No. 4,704,692, the contents of which are hereby incorporated by reference.

Antibody fragments and segments can be chemically linked where the bond formed between the fragments and segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Also disclosed are fragments of antibodies which have bioactivity. The fragments can be recombinant proteins obtained by cloning nucleic acids encoding the fragments in an expression system capable of producing the fragments, such as an adenovirus or baculovirus expression system. For example, one can determine the active domain of an antibody from a specific hybridoma that can cause a biological effect associated with the interaction of the antibody with, for example, hemagglutinin. For example, amino acids found to not contribute to either the activity or the binding specificity or affinity of the antibody can be deleted without a loss in the respective activity. For example, amino or carboxy-terminal amino acids can be sequentially removed from either the native or the modified non-immunoglobulin molecule or the immunoglobulin molecule and the respective activity assayed in one of many available assays. In another example, a fragment of an antibody can comprise a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa (see, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody can be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

Techniques can also be adapted for the production of single-chain antibodies specific to an epitope or antigen of interest (hemagglutinin, for example) (see e.g., U.S. Pat. No. 4,946,778). In addition, methods can be adapted for the construction of F(ab) expression libraries (see e.g., Huse, et al., 1989 Science 246: 1275-1281) to allow rapid and effective identification of monoclonal F(ab) fragments with the desired specificity for a protein or derivatives, fragments, analogs or homologs thereof. Antibody fragments that contain the idiotypes to a protein antigen can be produced by techniques known in the art including, but not limited to: (i) an $F(ab')_2$ fragment produced by pepsin digestion of an antibody molecule; (ii) an Fab fragment generated by reducing the disulfide bridges of an $F(ab')_2$ fragment; (iii) an Fab fragment generated by the treatment of the antibody molecule with papain and a reducing agent and (iv) Fv fragments.

Methods for the production of single-chain antibodies are well known to those of skill in the art. The skilled artisan is referred to U.S. Pat. No. 5,359,046, (incorporated herein by reference) for such methods. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding (Bedzyk et al., 1990; Chaudhary et al., 1990). The linker can be chosen to permit the heavy chain and light chain to bind together in their proper conformational orientation. See, for example, Huston, J. S., et al., Methods in Enzym. 203:46-121 (1991), which is incorporated herein by reference. These Fvs lack the constant regions (Fc) present in the heavy and light chains of the native antibody.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the $F(ab')_2$ fragment, that has two antigen combining sites and is still capable of cross-linking antigen.

Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. A $F(ab')_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

In hybrid antibodies, one heavy and light chain pair is homologous to that found in an antibody raised against one antigen recognition feature, e.g., epitope, while the other heavy and light chain pair is homologous to a pair found in an antibody raised against another epitope. This results in the property of multi-functional valency, i.e., ability to bind at least two different epitopes simultaneously. As used herein, the term "hybrid antibody" refers to an antibody wherein each chain is separately homologous with reference to a mammalian antibody chain, but the combination represents a novel assembly so that two different antigens are recognized by the antibody. Such hybrids can be formed, for example, by fusion of hybridomas producing the respective component antibodies, or by recombinant techniques. Such hybrids can, of course, also be formed using chimeric chains.

The antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby to ameliorate or prevent pathological conditions associated with an immune response, e.g., in the context of an autoimmune disease.

The targeting inaction of the antibody can be further used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Also included within the meaning of "antibody" are conjugates of antibody fragments and antigen binding proteins (single chain antibodies) as described, for example, in U.S. Pat. No. 4,704,692, the contents of which are hereby incorporated by reference.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY. Alternatively, the peptide or polypeptide can be independently synthesized in vivo as described above. Once isolated, these independent peptides or polypeptides can be linked to form an antibody via similar peptide condensation reactions.

For example, enzymatic ligation of cloned or synthetic peptide segments allow relatively short peptide fragments to be joined to produce larger peptide fragments, polypeptides or whole protein domains (Abrahmsen L. et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

The antibody can be bound to a substrate or labeled with a detectable moiety or both bound and labeled. The detectable moieties contemplated with the present compositions include fluorescent, enzymatic and radioactive markers.

In the case where there are two or more definitions of a term which is used and/or accepted within the art, the definition of the term as used herein is intended to include all such meanings unless explicitly stated to the contrary. A specific example is the use of the term, "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 4 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 4

| CDR Definitions[1] | Kabat | Chothia |
|---|---|---|
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbing of an CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an HA stem antibody or antigen-binding fragment, variant, or derivative thereof of the disclosed antibodies are according to the Kabat numbering system.

In camelid species, the heavy chain variable region, referred to as $V_{HH}$, forms the entire antigen-binding domain. The main differences between camelid $V_{HH}$ variable regions and those derived from conventional antibodies ($V_H$) include (a) more hydrophobic amino acids in the light chain contact surface of $V_H$ as compared to the corresponding region in $V_{HH}$, (b) a longer CDR3 in $V_{HH}$, and (c) the frequent occurrence of a disulfide bond between CDR1 and CDR3 in $V_{HH}$.
immunoglobulin molecule.

Antibody fragments, including single-chain antibodies, can comprise the variable region(s) alone or in combination with the entirety or a portion of the following: hinge region, $C_{H1}$, $C_{H2}$, and $C_{H3}$ domains. Also disclosed are antigen-binding fragments also comprising any combination of variable region(s) with a hinge region, $C_{H1}$, $C_{H2}$, and $C_{H3}$ domains. For example, antibody fragments comprising all or a portion of the heavy chain of a HA stem antibody can be used. Such antibody fragments can be effective because the heavy chain is inserted into stem region pocket and is dominant in specifying binding to the stem region (see Examples). Antibodies or immunospecific fragments thereof for use in the disclosed methods can be from any animal origin including birds and mammals. In some forms, the antibodies can be human, murine, donkey, rabbit, goat, guinea pig, camel, llama, horse, or chicken antibodies. In other forms, the variable region can be condricthoid in origin (e.g., from sharks). As used hereto, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described elsewhere herein and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion can comprise at least one of: a $C_{H1}$ domain, a hinge (e.g., upper, middle, and/or lower hinge region) domain, a $C_{H2}$ domain, a $C_{H3}$ domain, or a variant or fragment thereof. For example, an antibody for use in the disclosed methods can comprise a polypeptide chain comprising a $C_{H1}$ domain; a polypeptide chain comprising a $C_{H1}$ domain, at least a portion of a hinge domain, and a $C_{H2}$ domain; a polypeptide chain comprising a $C_{H1}$ domain and a $C_{H3}$ domain; a polypeptide chain comprising a $C_{H1}$ domain, at least a portion of a hinge domain, and a $C_{H3}$ domain, or a polypeptide chain comprising a $C_{H1}$ domain, at least a portion of a hinge domain, a $C_{H2}$ domain, and a $C_{H3}$ domain. In some forms, the disclosed antibody can comprise a polypeptide chain comprising a $C_{H3}$ domain. Further, an for us in the disclosed methods can lack at least a portion of a $C_{H2}$ domain (e.g., all or part of a $C_{H2}$ domain). As discussed elsewhere herein, it will be understood by one of ordinary skill in the art that these domains (e.g., the heavy chain portions) can be modified such that they vary in amino acid sequence from the naturally occurring immunoglobulin molecule.

In some forms, the disclosed antibodies (such as, for example, HA stem antibodies, and epitope- or antigen-binding fragments, variants, or derivatives thereof), the heavy chain portions of one polypeptide chain of a multimer can be identical to those on a second polypeptide chain of the multimer. Alternatively, heavy chain portion-containing monomers need not be identical. For example, each monomer can comprise a different target binding site, forming, for example, a bispecific antibody.

The heavy chain portions of an antibody can be derived from different immunoglobulin molecules. For example, a heavy chain portion of an antibody can comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. In some forms, the light chain portion can comprise at least one of a $V_L$ or $C_L$ domain.

The disclosed antibodies (such as, for example, HA stem antibodies, and epitope- or antigen-binding fragments, variants, or derivatives thereof) can be described or specified in terms of the epitope(s) or portion(s) of an antigen, for example, a target protein or polypeptide (a hemagglutinin composition, hemagglutinin fragment, or hemagglutinin stem portion, for example) that they recognize or specifically bind. The portion of a target polypeptide which specifically interacts with the antigen binding domain of an antibody is an "epitope," or an "antigenic determinant." As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies can be raised against N-terminal or C-terminal peptides of a polypeptide.

Particularly useful epitopes are, for example, the stem region of hemagglutinin and the epitope for antibody F10. A target polypeptide can comprise a single epitope, but typically comprises at least two epitopes, and can include any number of epitopes, depending on the size, conformation, and type of antigen. Furthermore, it should be noted that an "epitope" on a target polypeptide can be or include non-polypeptide elements, e.g., an "epitope" can include a carbohydrate side chain. Although antibodies, their generation and their binding properties are described herein in alternatively and individually in terms of epitope(s), antigen(s), peptide(s), polypeptide(s), protein(s), etc., it is understood that use or mention of one or a subset of these and related terms (which are intended to refer to epitopes and various molecules that comprise such epitopes) should be considered a reference to all such terms individually and in any combination. Thus, for example, reference to binding of an antibody to a protein should also be considered a reference to binding of the antibody to the relevant antigen, epitope, etc. that the protein comprises.

The minimum size of a peptide or polypeptide epitope for an antibody is thought to be about four to five amino acids. Peptide or polypeptide epitopes can contain, for example, at least seven, at least nine, or between at least about 15 to about 30 amino acids. Since a CDR can recognize an antigenic peptide or polypeptide in its tertiary form, the amino acids comprising an epitope need not be contiguous, and in some cases, may not even be on the same peptide chain. The HA stem region epitope described herein fall into this latter category. An epitope recognized by antibodies can contain a sequence of a least 4, at least 5, at least 6, at least 7, at least 8, at least9, at least 10, at least 15, at least 20, at least 25, or between about 15 to about 30 contiguous or non-contiguous amino acids of the target protein or polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{On}$) and the "off rate constant" ($K_{Off}$) can be determined by calculation of the concentrations and the actual rates of association and dissociation (See Nature 361:186-87 (1993)). The ratio of $K_{Off}/K_{On}$ enables the cancellation of all parameters not related to affinity, and is equal to the dissociation constant $K_d$ (See, generally, Davies et al. (1990) Annual Rev Biochem 59:439-473).

By "specifically binds" or "immunoreacts with" is meant that the antibody reacts with one or more antigenic determinants of the desired antigen and does not react with other polypeptides. Thus, "specifically binds" generally means that an antibody binds to an epitope via its antigen binding domain, and that the binding entails some complementarity between the antigen binding domain and the epitope.

According to this definition, an antibody is said to "specifically bind" to an epitope when it binds to that epitope, via its antigen binding domain more readily than it would bind to a random, unrelated epitope. The term, "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody can be considered to bind a first epitope preferentially if it binds said first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds, the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope.

An antibody can be said to bind a target polypeptide with an off rate (k(off)) of less than or equal to $5\times10^{-2}$ $sec^{-1}$, $10^{-2}$ $sec^{-1}$, $5\times10^{-3}$ $sec^{-1}$ or $10-3$ $sec^{-1}$. An antibody can be said to bind a target polypeptide with an off rate (k(off)), for example, less than or equal to $5\times10^{-4}$ $sec^{-1}$, $10^{-4}$ $sec^{-1}$, $5\times10^{-5}$ $sec^{-1}$, or $10^{-5}$ $sec^{-1}$, $5\times10^{-6}$ $sec^{-1}$, $10^{-6}$ $sec^{-1}$, $5\times10^{-7}$ $sec^{-1}$ or $10^{-7}$ $sec^{-1}$.

An antibody or antigen-binding fragment, variant, or derivative disclosed herein can be said to bind a target polypeptide with an on rate (k(on)) of greater than or equal to $10^3$ $M^{-1}$ $sec^{-1}$, $5\times10^3$ $M^{-1}$ $sec^{-1}$, $10^4$ $M^{-1}$ $sec^{-1}$, or $5\times10^4$ $M^{-1}$ $sec^{-1}$. An antibody can be said to bind a target polypeptide with an on rate (k(on)) greater than or equal to $10^5$ $M^{-1}$ $sec^{-1}$, $5\times10^5$ $M^{-1}$ $sec^{-1}$ $10^6$ $M^{-1}$ $sec^{-1}$, or $5\times10^6$ $M^{-1}$ $sec^{-1}$ or $10^7$ $M^{-1}$ $sec^{-1}$.

An antibody can be said to specifically bind to a influenza epitope when, for example, the equilibrium binding constant ($K_d$) can be, for example, $\leq 1$ µM, $\leq 100$ nM, $\leq 10$ nM, and $\leq 100$ pM to about 1 pM, as measured by assays such as radioligand binding assays or similar assays known to those skilled in the art.

An antibody is said to competitively inhibit binding of a reference antibody to a given epitope if it preferentially binds to that epitope to the extent that it blocks, in some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term, "avidity"5 refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Antibodies can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Antibodies can also be described or specified in terms of their binding affinity to a protein, polypeptide, epitope, antigen, etc. Examples of binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Antibodies can be "multispecific," e.g., bispecific, trispecific or of greater multispecificity, meaning that it recognizes and binds to two or more different epitopes present on one or more different antigens (e.g., proteins) at the same time. Thus, whether an antibody is "monospecific" or "multispecific," e.g., "bispecific," refers to the number of different epitopes with which an antibody reacts. Multispecific antibodies can be specific for different epitopes of a target polypeptide or can be specific for a target polypeptide as well as for a heterologous epitope, such as a heterologous polypeptide or solid support material.

As used herein the term "valency" refers to the number of potential binding domains, e.g., antigen binding domains, present in an antibody. Each binding domain specifically binds one epitope. When an antibody comprises more than one binding domain, each binding domain can specifically bind the same epitope, for an antibody with two binding domains, termed "bivalent monospecific," or to different epitopes, for an antibody with two binding domains, termed "bivalent bispecific." An antibody can also be bispecific and bivalent for each specificity (termed "bispecific tetravalent antibodies"). In some forms, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Those skilled in the art will recognize that it is possible to determine, without undue experimentation if an antibody (such as a human antibody or human monoclonal antibody) has the same specificity as a disclosed antibody (such as a human antibody or human monoclonal antibody) by ascertaining whether the former prevents the latter from binding to the HA protein of the influenza virus. If the antibody being tested competes with the disclosed antibody, as shown by a decrease in binding by the disclosed antibody, then it is likely that the two antibodies bind to the same, or to a closely related, epitope.

Another way to determine whether an antibody (such as a human antibody or human monoclonal antibody) has the specificity of a disclosed antibody (such as a human antibody or human monoclonal antibody) is to pre-incubate the disclosed antibody with the influenza HA protein, with which it is normally reactive, and then add the antibody being tested to determine if the antibody being tested is inhibited in its ability to bind the HA protein. If the antibody being tested is inhibited then, in all likelihood, it has the same, or functionally equivalent, epitope specificity as the disclosed antibody. Screening of disclosed antibodies can be also carried out by utilizing the influenza virus and determining whether the test antibody is able to neutralize the influenza virus.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "$C_{H1}$ domain" includes the first (most amino terminal) constant region domain of an immunoglobulin heavy chain. The $C_{H1}$ domain is adjacent to the $V_H$ domain and is amino terminal to the hinge region of an immunoglobulin heavy chain molecule.

As used herein the term "$C_{H2}$ domain" includes the portion of a heavy chain molecule that extends, for example, from about residue 244 to residue 360 of an antibody using conventional numbering schemes (residues 244 to 360, Kabat numbering system; and residues 231-340, EU numbering system; see Kabat E A et al. op. cit. The $C_{H2}$ domain is unique in that it is not closely paired with another domain. Rather, two N-linked branched carbohydrate chains are interposed between the two $C_{H2}$ domains of an intact native IgG molecule. It is also well documented that the $C_{H3}$ domain extends from the $C_{H2}$ domain to the C-terminal of the IgG molecule and comprises approximately 108 residues.

As used herein, the term "hinge region" includes the portion of a heavy chain molecule that joins the $C_{H1}$ domain to the $C_{H2}$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_{H1}$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" means any antibody where some regions, sites or sequences come form two or more different species. For example, the immunoreactive region or site can obtained or derived from a first species and the constant region (which may be intact, partial or modified as described herein) can be obtained from a second species. In some forms, the target binding region or site can be from a non-human source (e.g. mouse or primate) and the constant region can be human.

As used herein, the term "engineered antibody" refers to an antibody in which the variable domain in either the heavy and light chain or both is altered by at least partial replacement of one or more CDRs from an antibody of known specificity and, optionally, by partial framework region replacement and sequence changing. Although the CDRs can be derived from an antibody of the same class or even subclass as the antibody from which the framework regions are derived, the CDRs can also be derived from an antibody of different class and/or from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded" protein or polypeptide includes proteins and polypeptides (e.g., HA and HA stem region) in which all of the functional domains comprising the protein or polypeptide are distinctly active. As used herein, the term "improperly folded" protein or polypeptide includes proteins and polypeptides in which at least one of the functional domains of the protein or polypeptide is not active. In some forms, a properly folded polypeptide comprises polypeptide chains linked by at least one disulfide bond and, conversely, an improperly folded polypeptide comprises polypeptide chains not linked by at least one disulfide bond. In the context of hemagglutinin, properly folded hemagglutinin or properly folder hemagglutinin stem region refers hemagglutinin (or hemagglutinin region) that has a native conformation. In the context of the disclosed HA stem antibodies and methods, a properly folded hemagglutinin or properly folded hemagglutinin stem region is, for example, one to which antibody F10 can bind, specifically bind, preferentially bind, etc.

As used herein the term "engineered" includes manipulation of nucleic acid, or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Any of the disclosed antibodies or other described antibodies can be included or excluded from any group or genus of antibodies and from use in any method, including the disclosed methods. Thus, for example, antibodies D7, D8, F10, G17, H40, A66, H98, D80, E90, and E8 described herein: C179 (described by Okuno et al., A common neutralizing epitope conserved between the hemagglutinins of influenza A virus H1 and H2 strains. *J Virol* 67, 2552-8 (1993)), and the antibodies described by Kashyap et al., Combinatorial antibody libraries from survivors of the Turkish H5N1 avian influenza outbreak reveal virus neutralization strategies. *Proc Natl Acad Sci USA* 105, 5986-91 (2008), can be, individually of in any combination, included or excluded.

B. Hemagglutinin Compositions

Disclosed are hemagglutinin compositions. The disclosed hemagglutinin compositions are useful as immunogens, e.g. vaccines, to stimulate a subjects immune response to influenza virus. For example, disclosed are hemagglutinin compositions that comprise, for example, the hemagglutinin stem region, either as part of a full hemagglutinin complex, as part of a trimeric ectodomain of hemagglutinin, as part of the extracellular portion of hemagglutinin, or in isolation from other parts of hemagglutinin. The hemagglutinin composition can be immobilized on a surface. For example, the hemagglutinin composition can be the stem region of hemagglutinin in the neutral pH conformation in isolation from the head region of hemagglutinin, thereby identifying antibodies of interest. For example, the hemagglutinin composition can be hemagglutinin in the neutral pH conformation in isolation from other components of influenza virus, where the head region of the hemagglutinin is modified to reduce the antigenicity of the head region. Because the stem region is formed in trimeric hemagglutinin, hemagglutinin compositions that include the stem region of trimeric hemagglutinin are particularly useful. For example, the hemagglutinin composition includes an isolated peptide (natural or synthetic) that includes the F10 epitope, an F10 epitope unit and any mimotope thereof. An F10 epitope or an F10 epitope unit for the purposes of the present invention is a portion of an antigen molecule, e.g. hemagglutinin, which is delineated by the area of interration with the F10 antibody. The meaning of mimotope is defined as an entity which is sufficiently similar to the native F10 epitope so as to be capable of being recognized by antibodies which recognize the native F10 epitope; (Gheysen, H. M., et al., 1986, Synthetic peptides as antigens. Wiley, Chichester, Ciba foundation symposium 119, p 130-149; Gheysen, H. M., 1986, Molecular Immunology, 23, 7, 709-715); or are capable of raising antibodies, when coupled to a suitable carrier, which antibodies cross-react with the native F10 epitope.

In some forms the hemagglutinin compositions are immunogen compositions. The immunogen compositions according to the invention contain an epitope or epitope unit recognized by a protective monoclonal antibody having the specificity for the stem region of hemagglutinin protein of an influenza virus. A protective monoclonal antibody having the specificity for the stem region of hemagglutinin protein of an influenza virus includes monoclonal antibody D7, F8, F10, G17, H40, A66, D80, E88, E90, or H98 disclosed herein or a monoclonal antibody that competes with the binding of monoclonal antibody D7, D8, F10, G17, H40, A66, D80, E88, E90, or H98 to the HA protein. The antibody binds both the HA1 and HA2 peptide.

An epitope or epitope unit is for example the F10 epitope. By F10 epitope it is meant the epitope recognized by the F10 antibody disclosed herein. The epitope is a confirmation epitope defined by amino acids of the HA1 and HA2 peptide of hemagglutinin protein of the influenza virus. The hemagglutinin protein is in the neutral pH conformation. Specifically, the F10 epitope is defined by amino acid residues 18, 38, 39, 40 and 291 of HA1 and 18, 19, 20, 21, 38, 41, 42, 45, 49, 52, 53, and 56 of HA2 when the hemagglutinin in the neutral pH conformation.

In some forms the hemagglutinin composition is conjugated (e.g. a chimeric peptide) having one or more peptides or peptide fragments linked to a backbone where peptides or peptide fragments are spatially positioned relative to each other so that they together form a non-linear sequence which mimics the tertiary structure of an F10 epitope, wherein said conjugate competes with the binding of monoclonal antibody F10 to the HA protein. The backbone is a peptide backbone wherein peptides corresponding to segments of native hemagglutinin are coupled to form an epitope mimicking an the F10 epitope. Alternatively the peptide backbone mimics the structure of the native hemagglutin protein such that peptides are coupled to for form an epitope mimicking an the F10 epitope. Optionally, the backbone is a non-peptide backbone having two or more attachment points onto which peptides are coupled. See, WO9738011, the contents of which are incorporated by reference.

The peptides or peptide fragments that make up the F10 epitope include one or more of the following peptides a)
(SEQ ID NO: 130)
$[Xaa_0]_m$-$Xaa_1$-$Xaa_2$-$[Xaa_0]_p$ wherein, m, and p are independently 0 or 1-10,
$Xaa_0$, is independently any amino acid,
  $Xaa_1$ is S, T, F H or Y, and
  $Xaa_2$ is H, Y, M, L or Q;

b)
(SEQ ID NO: 131)
$[Xaa_0]_m$-$Xaa_1$-$Xaa_2$-$[Xaa_0]_p$ wherein, m, and p are independently 0 or 1-10,
$Xaa_0$, is independently any amino acid, and
  $Xaa_1$ is H, Q, Y, S, D, N or T,
  $Xaa_2$ is Q, E, K, I, V, M, E, R or T;

c)
(SEQ ID NO: 132)
$[Xaa_0]_m$-$Xaa_1$-$Xaa_2$-$Xaa_3$-$Xaa_4$-$[Xaa_0]_p$ wherein, m, and p are independently 0 or 1-10,
$Xaa_0$, is independently any amino acid, and
  $Xaa_1$ is I, V, M, or L;
  $Xaa_2$ is D, N, H, Y, D, A, S or E,
  $Xaa_3$ is G or A, and
  $Xaa_4$ is W, R, or G; or d)
(SEQ ID NO: 133)
$[Xaa_0]_m$-$Xaa_1$-$[Xaa_0]_q$ $Xaa_2$-$Xaa_3$-$[Xaa_0]_q$ $Xaa_4$-

$[Xaa_0]_r$ $Xaa_5$-$[Xaa_0]_q$-$Xaa_6$ $Xaa_7$-$[Xaa_0]_q$-$Xaa_8$-

$[Xaa_0]_p$ wherein, m, and p are independently 0 or 1-10, q is 2, and r is 3
$Xaa_0$, is independently any amino acid, and
  $Xaa_1$ is K, Q, R, N, L, G, F, H or Y,
  $Xaa_2$ is S or T, $Xaa_3$ is Q or P,
  $Xaa_4$ is F, V, I, M, L, or T,
  $Xaa_5$ is I, T, S, N, Q, D, or A,
  $Xaa_6$ is I, V, M, or L,
  $Xaa_7$ is N, S, T, or D
  $Xaa_8$ is I, F, V, A, or T;

e)
(SEQ ID NO: 134)
$[Xaa_0]_m$-$Xaa_1$-$[Xaa_0]_q$ $Xaa_2$-$Xaa_3$-$[Xaa_0]_q$ $Xaa_4$-

$[Xaa_0]_r$ $Xaa_5$-$[Xaa_0]_q$-$Xaa_6$ $Xaa_7$-$[Xaa_0]_s$-$[Xaa_8]_t$-

$[Xaa_0]_p$ wherein, m, and p are independently 0 or 1-10, q is 2, r is 3, s is 0 or 2, and t is 0 or 1,
$Xaa_0$, is independently any amino acid, and
  $Xaa_1$ is K, Q, R, N, L, G, F, H or Y,
  $Xaa_2$ is S or T,
  $Xaa_3$ is Q or P,
  $Xaa_4$ is F, V, I, M, L, or T,
  $Xaa_5$ is I, T, S, N, Q, D, or A,
  $Xaa_6$ is I, V, M, or L,
  $Xaa_7$ is N, S, T, or D,
  $Xaa_8$ I, F, V, A, or T.

The peptide can be a linear peptide of a cyclic peptide. Linear peptide can be prepared synthetically and then screened for a particular characteristic in various biological assays. E. g., Scott, J. K. and G. P. Smith, Science 249:384, 1990; Devlin, J. J., et al., Science 24:404, 1990; Furka, A. et al., Int. J. Pept. Protein Res. 37:487, 1991; Lam, K. S., et al., Nature 354:82, 1991.

Cyclized peptides are often found to possess superior immunogenic activity compared to linear peptide immunogens. Linear peptide immunogens comprising three or more core sequences are found to bind with the terminal sequences only, while cyclization allows binding by all core sequences present in the peptide immunogens. Various methods for producing cyclic peptides have been described. One involves solution or liquid phase peptide synthesis, where amino acid residues in solution are linked by peptide bonds, with reactive groups not involved in the peptide bond formation, such as the amino group of the N-terminal residue, the carboxy group of the C-terminal residue, sulfhydryl groups on cysteine residues and similar or other reactive groups in the amino acid side chains, protected by suitable protecting groups.

In one embodiment cyclic peptide immunogens are formed using terminal cysteine residues by reduction of thiol groups to form disulfide bridges.

Another approach involves solid phase peptide synthesis, is which synthesis is carried out on an insoluble solid matrix. Protecting groups are employed for reactive side chains. The general methodology of solid phase synthesis is well known in the art. Merrifield, R. B., Solid phase synthesis (Nobel lecture). Angew Chem 24:799-810 (1985) and Barany et al., The Peptides, Analysis, Synthesis and Biology, Vol. 2, Gross, E. and Meienhofer, J., Eds. Academic Press 1-284 (1980). For example, chemical reaction protocols, such as those described in U.S. Pat. Nos. 4,033,940 and 4,102,877, have been devised to produce circularized peptides. In other techniques, biological and chemical methods are combined to produce cyclic peptides. These latter methods involve first expressing linear precursors of cyclic peptides in cells (e.g., bacteria) to produce linear precursors of cyclic peptides and then adding of an exogenous agent such as a protease or a nucleophilic reagent to chemically convert these linear precursors into cyclic peptides. See, e.g., Camerero, J. A., and Muir, T. W., J. Am. Chem. Society. 121:5597 (1999); Wu, H. et al. Proc. Natl. Acad. Sci. USA, 95:9226 (1998).

Head-to-tail (backbone) peptide cyclization has been used to rigidify structure and improve in vivo stability of small bioactive peptides (see Camarero and Muir, J. Am. Chem. Soc., 121:5597-5598 (1999)). An important consequence of peptide cyclization is retention of biological activity and/or the identification of new classes of pharmacological agents. A chemical cross-linking approach was used to prepare a backbone cyclized version of bovine pancreatic trypsin inhibitor (Goldenburg and Creighton, J. Mol. Biol., 165: 407-413 (1983)). Other approaches include chemical (Camarero et al., Angew. Chem. Int. Ed., 37:347-349 (1998); Tam and Lu, Prot. Sci., 7:1583-1592 (1998); Camarero and Muir, Chem. Commun., 1997:1369-1370 (1997); and Zhang and Tam, J. Am. Chem. Soc. 119:2363-2370 (1997)) and enzymatic (Jackson et al., J. Am. Chem. Soc., 117:819-820 (1995)) intramolecular ligation methods which allow linear synthetic peptides to be efficiently cyclized under aqueous conditions.

A native chemical ligation approach utilizes inteins (internal proteins) to catalyze head-to-tail peptide and protein ligation in vivo (see, for example, Evans et al., J. Biol. Chem. 274:18359-18363 (1999); Iwai and Pluckthun, FEBS Lett. 459.166-172 (1999); Wood et al., Nature Biotechnology 17:889-892 (1999); Camarero and Muir, J. Am. Chem. Soc. 121:5597-5598 (1999); and Scott et al., Proc. Natl. Acad. Sci. USA 96:13638-13643 (1999)).

Preparation of vaccines, which contain hemagglutinin compositions as active ingredients, is generally well understood in the art as exemplified by U.S. Pat. Nos. 4,608,251; 4,601,903; 4,599,231; 4,599,230, 4,596,792, and 4,578,770, all incorporated herein by reference.

The hemagglutinin composition used in the vaccinal strategy according to the present invention can also be obtained using genetic engineering methods. The one skilled in the art can refer to the known sequence of the phage insert that expresses a specific epitope unit of an immunogenic polypeptide mimic of the invention and also to the general literature to determine the appropriate codons that can be used to synthesize the desired peptide. There is no need to say that the expression of the polynucleotide that encodes the immunogenic polypeptide mimic of interest may be optimized, according to the organism in which the sequence has to be expressed and the specific codon usage of this organism (mammal, plant, bacteria, etc.). For bacteria and plant, respectively, the general codon usages can be found in European patent application No. EP 0 359 472 (Mycogen).

As an alternative embodiment, the epitope unit according to the present invention is recombinantly expressed as a part of longer polypeptide that serves as a carrier molecule. Specifically, the polynucleotide coding for the immunogenic polypeptide of the invention, for example a polypeptide having an amino acid length between 10 and 200 amino acid residues, is inserted at at least one permissive site of the polynucleotide coding for the *Bordetella* cyaA adenylate cyclase, for example, at a nucleotide position located between amino acids 235 and 236 of the *Bordetella* adenylate cyclase. Such a technique is fully described in the U.S. Pat. No. 5,503,829 granted on Apr. 2, 1996 (Leclere et al.).

In another embodiment of the hemagglutinin composition according to the present invention, the nucleotide sequence coding for the desired immunogenic polypeptide carrying one or more epitope units is inserted in the nucleotide sequence coding for surface protein of Haemophilus influenza, such as described in PCT Application No. PCT/US96/17698 (The Research Foundation of State University of New York), which is incorporated by reference herein.

In another embodiment of the hemagglutinin composition according to the invention, the composition comprises a polynucleotide coding for the immunogenic polypeptide or oligomeric peptide of pharmaceutical interest.

For the purpose of the present invention, a specific embodiment of comprises the in vivo production of a hemagglutinin composition for example in an oligomeric form by the introduction of the genetic information in the mammal organism, specifically in the patient organism. This genetic information can be introduced in vitro in a cell that has been previously extracted from the organism, the modified cell being subsequently reintroduced in the said organism directly in vivo into the appropriate tissue. The method for delivering the corresponding protein or peptide to the interior of a cell of a vertebrate in vivo comprises the step of introducing a preparation comprising a pharmaceutically acceptable injectable carrier and a polynucleotide operatively coding for the polypeptide into the interstitial space of a tissue comprising the cell, whereby the polynucleotide is taken up into the interior of the cell and has a pharmaceutical effect.

In a specific embodiment, the invention provides a hemagglutinin composition comprising a polynucleotide operatively coding for the ypeptide of interest or one of its above-described peptides in solution in a physiologically acceptable injectable carrier and suitable for introduction interstitially into a tissue to cause cells of the tissue to express the said protein or polypeptide.

The polynucleotide operatively coding for the hemagglutinin composition, mimic or oligomeric peptide can be a vector comprising the genomic DNA or the complementary DNA (cDNA) coding for the corresponding protein or its protein derivative and a promoter sequence allowing the expression of the genomic DNA or the complementary DNA in the desired eukaryotic cells, such as vertebrate cells, specifically mammalian cells. The vector component of a therapeutic composition according to the present invention is advantageously a plasmid, a part of which is of viral or bacterial origin, which carries a viral or a bacterial origin of replication and a gene allowing its selection, such as an antibiotic resistance gene. By "vector" according to this specific embodiment of the invention is intended a circular or linear DNA molecule. This vector can also contain an origin of replication that allows it to replicate in the eukaryotic host cell, such as an origin of replication from a bovine papillomavirus.

Therapeutic compositions comprising a polynucleotide are described in PCT application No. WO 90/11092 (Vical Inc.), and also in PCT application No. WO 95/11307 (Institut Pasteur, INSERM, Universite d'Ottawa), as well as in the articles of Tacson et al. (1996, Nature Medicine, 2(8):888-892) and of Huygen et al. (1996, Nature Medicine, 2(8): 893-898).

In another embodiment, the DNA to be introduced is complexed with DEAE-dextran (Pagano et al., 1967, J. Virol., 1:891) or with nuclear proteins (Kaneda et al., 1989, Science, 243:375), with lipids (Felgner et al., 1987, Proc. Natl. Acad. Sci., 84:7413), or encapsulated within liposomes (Fraley et al., 1980, J. Biol. Chem., 255:10431).

In another embodiment, the therapeutic polynucleotide can be included in a transfection system comprising polypeptides that promote its penetration within the host cells as described in PCT application No. WO 95/10534 (Seikagaku Corporation).

The therapeutic polynucleotide and vector according to the present invention can advantageously be administered in the form of a gel that facilitates transfection into the cells. Such a gel composition can be a complex of poly-L-l-lysine and lactose as described by Midoux (1993, Nucleic Acids Research, 21:871-878) or also poloxamer 407 as described by Pastore (1994, Circulation, 90:1-517). The therapeutic polynucleotide and vector according to the invention can also be suspended in a buffer solution or be associated with liposomes.

Thus, the polynucleotide and vector according to the invention are used to make pharmaceutical compositions for delivering the DNA (genomic DNA or cDNA) coding for the immunogenic polypeptide mimic of the invention at the site of the injection. The amount of the vector to be injected varies according to the site of injection. As an indicative dose, the vector can be injected in an amount of about 0.1 and about 100 μg of the vector in a patient.

In another embodiment of the therapeutic polynucleotide according to the invention, the polynucleotide can be introduced in vitro into a host cell, preferably in a host cell previously harvested from the patient to be treated, and more preferably a somatic cell such as a muscle cell. In a subsequent step, the cell that has been transformed with the vaccinal nucleotide coding for the immunogenic polypeptide of the invention is implanted back into the patient in order to deliver the recombinant protein within the body either locally or systemically.

Consequently, the present invention also concerns an immunogenic composition comprising a polynucleotide or an expression vector as described hereinabove in combination with a pharmaceutically acceptable vehicle allowing its administration to the human or other animal. A further embodiment of the invention comprises a vaccine composition comprising a polynucleotide or a vector as described above in combination with a pharmaceutically acceptable vehicle allowing its administration to the human or the animal.

The approach of increasing immunogenicity of small immunogenic molecules by conjugating these molecules to large "carrier" molecules has been utilized successfully for decades (see, e.g., Goebel et al. (1939) J. Exp. Med. 69: 53). For example, many immunogenic compositions have been described in which purified capsular polymers have been conjugated to carrier proteins to create more effective immunogenic compositions by exploiting this "carrier effect." Schneerson et al. (1984) Infect. Immun. 45: 582-591).

In one aspect of the invention, method for conjugating a hemagglutinin composition, e.g. immunogen according to the invention via a reactive group of an amino acid residue of the peptide immunogen to a protein/polypeptide carrier having one or more functional groups is provided. The protein/polypeptide carrier may be human serum albumin, keyhole limpet hemocyanin (KLH), immunoglobulin molecules, thyroglobulin, ovalbumin, influenza hemagglutinin, PAN-DR binding peptide (PADRE polypeptide), malaria circumsporozite (CS) protein, hepatitis B surface antigen ($HBSAg_{19-28}$, Heat Shock Protein (HSP) 65, *Bacillus* Calmette-Guerin (BCG), cholera toxin, cholera toxin mutants with reduced toxicity, diphtheria toxin, $CRM_{197}$ protein that is cross-reactive with diphtheria toxin, recombinant Streptococcal C5a peptidase, *Streptococcus pyogenes* ORF1224, *Streptococcus pyogenes* ORF1664, *Streptococcus pyogenes* ORF 2452, *Chlamydia pneumoniae* ORF T367, *Chlamydia pneumoniae* ORF T858, Tetanus toxoid, HIV gp120 T1, microbial surface components recognizing adhesive matrix molecules (MSCRAMMS), growth factor/hormone, cytokines or chemokines.

The hemagglutinin composition, e.g. immunogen can be used as vaccines to generate an anti-influenza HA-mediated immune response in order to prevent influenza infections. Synthetic peptides require both stabilization and adjuvantation for the induction of an effective immune response in vivo. Various methods have been employed to protect synthetic peptide immunogens against degradation in vitro and in vivo, mediated by various processes including chemical and physical pathways, (Manning M C, et al. Pharmaceutical Research, 1989, 6:903-918).

Numerous adjuvants and/or depot-based parenteral, mucosal or transdermal delivery systems destined for use with human or veterinary vaccines have been developed to enhance the immune response. These include the use of mineral salts, water-in-oil (w/o)-emulsions, liposomes, polymeric microparticles, nanoparticles and gels/hydrogels. (Cox J C, et al. Vaccine, 1997, 15:248-256). Freund's complete adjuvant (FCA), a suspension of heat-killed *M. tuberculosis* mycobacteria in mineral oil containing a surfactant, has been recognized as one of the most powerful adjuvants. Adjuvants are well known in the art (Vaccine Design—The Subunit and Adjuvant Approach, 1995, Pharmaceutical Biotechnology, Volume 6, Eds. Powell, M. F., and Newman, M. J., Plenum Press, New York and London, ISBN 0-306-44867-X). Preferred adjuvants for use with immunogens of the present invention include aluminium or calcium salts (hydroxide or phosphate). Adjuvants may be selected from GM-CSF, 529 SE, IL-12, aluminum phosphate, aluminum hydroxide, *Mycobacterium tuberculosis, Bordetella pertussis*, bacterial lipopolysaccharides, aminoalkyl glucosane phosphate compounds, MPL™ (3-O-deacylated monophosphoryl lipid A), a polypeptide, Quil A, STIMULON™ QS-21, a pertussis toxin (PT), an *E. coli* heat-labile toxin (LT), IL-1alpha, IL-1β, IL-2, IL-4, IL-5, IL-6, IL-7, IL-8, IL-10, IL-13, IL-14, IL-15, IL-16, IL-17, IL-18, interferon-alpha, interferon-β, interferon-gamma, G-CSF, TNF-alpha and TNF-β.

Still other adjuvants include mineral oil and water emulsions, calcium salts such as calcium phosphate, aluminum, salts (alum), such as aluminum hydroxide, aluminum phosphate, etc., Amphigen, Avridine, L121/squalene, D-lactide-polylactide/glycoside, pluronic acids, polyols, muramyl dipeptide, killed *Bordetella*, saponins, such as Stimulon™. QS-21 (Antigenics, Framingham, Mass.), described in U.S. Pat. No. 5,057,540, which is hereby incorporated by reference3, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, which are/incorporated herein by reference for all purposes.

Also useful as adjuvants are cholera toxins and mutants thereof, including those described in published International Patent Application No. WO 00/18434 (wherein the glutamic acid at amino acid position 29 is replaced by another amino acid (other than aspartic acid, preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid position 35 and 36).

Various methods may be employed to adjuvant synthetic peptide-based immunogens, but normally a carrier or depot system is required for effective long-term immunogenic responses. Notable examples include adsorbing the immunogen onto a mineral salt or gel. For example, encapsulating a peptide immunogen within a polymeric matrix (monolithic matrix) or gel, or layering a polymeric material around a peptide immunogen (core-shell) may be an effective strategy. Or, an immunogen may be incorporated in a liposome or vesicular type of formulation, with the immunogen either embedded in the lipid matrix or physically entrapped in the internal aqueous phase. Another strategy may employ a mineral-based, vegetable-based or animal-based oil, with an aqueous solution of the immunogen in various proportions, to prepare a water-in-oil (w/o)-emulsion or a water-in-oil-in-water (w/o/w)-double emulsion. Powell M F, et al., Pharmaceutical Biotechnology, Vol. 6, Plenum Press, New York, 1995

In some forms, the head region of the hemagglutinin can be modified by removing or replacing glycosylation sites. In some forms, the head region of the hemagglutinin can be modified by adding glycosylation sites. In some forms, the head region of the hemagglutinin can be modified by removing all or a portion of the head region.

In some forms, the hemagglutinin composition can be or be derived from hemagglutinin from a group 2 influenza virus. In some forms, the hemagglutinin composition can be or be derived form hemagglutinin from a group 1 influenza virus. In some forms, the hemagglutinin composition can be or be derived from hemagglutinin from a particular cluster, subcluster or subtype of influenza virus. In some forms, the hemagglutinin composition can be or be derived from a combination of hemagglutinins from a combination of particular clusters, subclusters and/or subtypes of influenza virus.

In some forms, the disclosed hemagglutinin compositions can produce an immune reaction in a subject. For example, in some forms, the subject can produce an immune response that prevents or reduces the severity of an influenza infection. In some forms, the immune response can be reactive to influenza viruses within a subtype. In some forms, the immune response can be reactive to influenza viruses in each subtype within a cluster. In some forms, the immune response can be reactive to influenza viruses in each cluster within a group. In some forms, the immune response can be reactive to all influenza viruses in each subtype within a group. In some forms, the immune response can be reactive to influenza viruses within group 1.

Disclosed are hemagglutinin compositions comprising, for example, hemagglutinin, a trimeric ectodomain of hemagglutinin, the extracellular portion of hemagglutinin, a trimeric stem region of hemagglutinin lacking all or a portion or portions of the head structure, or the hemagglutinin stem region in isolation from other parts of hemagglutinin. Disclosed are hemagglutinin compositions comprising, for example, hemagglutinin, a trimeric ectodomain of hemagglutinin, the extracellular portion of hemagglutinin, or a trimeric stem region of hemagglutinin lacking a portion or portions of the head structure where the head region of the hemagglutinin is modified by removing and/or replacing one or more glycosylation sites. Disclosed are hemagglutinin compositions comprising, for example, hemagglutinin, a trimeric ectodomain of hemagglutinin, the extracellular portion of hemagglutinin, or a trimeric stem region of hemagglutinin lacking a portion or portions of the head structure where the head region of the hemagglutinin is modified by adding one or more glycosylation sites. Disclosed are hemagglutinin compositions comprising, for example, hemagglutinin, a trimeric ectodomain of hemagglutinin, the extracellular portion of hemagglutinin, or a trimeric stem region of hemagglutinin lacking a portion or portions of the head structure where the head region of the hemagglutinin is modified by removing and/or replacing one or more glycosylation sites and by adding one or more glycosylation sites. In some forms, the head region of the hemagglutinin can be modified by removing all or a portion of the head region. For example, some or all of the amino acids of the head regions in a trimeric ectodomain of hemagglutinin can be removed to leave portions of the head region of loops between the stem region portions of the trimer.

It has been discovered that hemagglutinin bound or immobilized on a substrate or surface exposes or presents the stem region epitope(s) of hemagglutinin for effective binding by antibodies. This allowed the identification of a number of broad-spectrum neutralizing antibodies against hemagglutinin and against influenza virus. Accordingly, disclosed are compositions comprising hemagglutinin composition bound or immobilized on a substrate or surface. Binding, attachment, and/or immobilization of proteins to substrates, solid supports an surfaces is a well established art and those of skill in the art can use any known techniques, chemistries and materials to bind hemagglutinin and hemagglutinin compositions to any suitable material.

Hemagglutinin and hemagglutinin compositions immobilized on a solid support can also be used, for example, to generate an immune response in a subject. For example, beads, microparticles or nanoparticles with hemagglutinin composition bound to the surface can be administered to subjects. Because of the discovery that immobilized hemagglutinin can be bound by antibodies specific for the hemagglutinin stem region, such compositions can be used to generate an immune response in a subject. Such an immune response can produce antibodies and immune system components that can inhibit influenza virus.

A influenza protein (e.g., HA or neuramindase), or a derivative, fragment, analog, homolog or ortholog thereof, can be utilized as an immunogen in the generation of antibodies that immunospecifically bind these protein components. The disclosed hemagglutinin compositions are an example.

Solid supports or surface are solid-state substrates, compositions, surfaces and/or supports with which molecules, such as hemagglutinin, hemagglutinin compositions and/or antibodies, can be associated. Molecules can be associated with solid supports directly or indirectly. For example, molecules can be bound to the surface of a solid support or associated with capture agents (e.g., compounds or molecules that bind an analyte) immobilized on solid supports. An array is a solid support to which multiple molecules have been associated in an array, grid, or other organized pattern.

Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a polygonal (e.g., rectangular, square, triangular, circular) small piece of material. Useful forms for solid-state substrates are plates, dishes, thin films, beads, or chips. A useful form for a solid-state substrate is a microtiter dish. In some embodiments, a multiwell glass slide can be employed.

An array can include a plurality of molecules immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification.

Although useful, it is not required that the solid support be a single unit or structure. A set of molecules can be distributed over any number of solid supports. For example, at one extreme, each component can be immobilized in a separate reaction tube or container, or on separate beads or microparticles.

Each of the components immobilized on the solid support can be located in a different predefined region of the solid support. The different locations can be different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,00 different components immobilized on the solid support.

C. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for identifying HA stem antibodies, the kit comprising one or more of the antibodies D7, D8, F10, G17, H40, A66, H98, D80, E90, and E8.

D. Mixtures

Disclosed are mixtures formed by performing or preparing to perform the disclosed method. For example, disclosed are mixtures comprising a cell and one or more of the antibodies D7, D8, F10, G17, H40, A66, H98, D80, E90, and E8.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

E. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising one or more of the antibodies D7, D8, F10, G17, H40, A66, H98, D80, E90, and E8 and a machine to detect antibody binding.

F. Data Structures and Computer Control

Disclosed are data structures used in, generated by, or generated from, the disclosed method. Data structures generally are any form of data, information, and/or objects collected, organized, stored, and/or embodied in a composition or medium. An antibody titre stored in electronic form, such as in RAM or on a storage disk, is a type of data structure.

The disclosed method, or any part thereof or preparation therefor, can be controlled, managed, or otherwise assisted by computer control. Such computer control, can be accomplished by a computer controlled process or method, can use and/or generate data structures, and can use a computer program. Such computer control, computer controlled processes, data structures, and computer programs are contemplated and should be understood to be disclosed herein.

Uses

The disclosed methods and compositions are applicable to numerous areas including, but not limited to, identifying and confirming the potency of HA stem antibodies, passive immunization with the HA stem antibodies and active immunization using the disclosed hemagglutinin compositions. Other uses include as a control for detecting HA stem antibodies in a body fluid. Other uses are disclosed, apparent from the disclosure, and/or will be understood by those in the art.

Method

Disclosed are methods of treating subjects, methods of screening and producing antibodies and methods of screening for F10 mimitopes useful as immunogens. For example, disclosed is a method of treating a subject suffering or at risk of influenza infection, the method comprising administering to the subject one or more of the disclosed hemagglutinin compositions and/or antibodies, such as the disclosed HA stem antibodies. For example, disclosed is a method of treating a subject, the method comprising administering to the subject the stem region of influenza hemagglutinin in the neutral pH conformation in isolation from other components of influenza virus, wherein the subject produces an immune response to the stem region. For example, disclosed is a method of treating a subject, the method comprising administering to the subject the stem region of influenza hemagglutinin in the neutral pH conformation in isolation from the head region of hemagglutinin, wherein the subject produces an immune response to the stem region. For example, disclosed is a method of treating a subject, the method comprising administering to the subject influenza hemagglutinin in the neutral pH conformation in isolation from other components of influenza virus, wherein the head region of the hemagglutinin is modified to reduce the antigenicity of the head region, wherein the subject produces an immune response to the stem region. For example, disclosed is a method for treating a subject by administering a hemagglutinin composition. The hemagglutinin composition according to the invention contain an epitope or epitope unit recognized by a protective monoclonal antibody having the specificity for the stem region of hemagglutinin protein of an influenza virus. A protective monoclonal antibody having the specificity for the stem region of hemagglutinin protein of an influenza virus includes monoclonal antibody D7, D8, F10, G17, H40, A66, D80, E88, E90, or H98 disclosed herein or a monoclonal antibody that competes with the binding of monoclonal antibody D7, D8, F10, G17, H40, A66, D80, E88, E90 or H98 to the HA protein. The antibody binds both the HA1 and HA2 peptide.

An epitope or epitope unit is for example the F10 epitope. By F10 epitope it is meant the epitope recognized by the F10 antibody disclosed herein. The epitope is a confirmation epitope defined by amino acids of the HA1 and HA2 peptide of hemagglutinin protein of the influenza virus. The hemagglutinin protein is in the neutral pH conformation. Specifically, the F10 epitope is defined by amino acid residues 18, 38, 39, 40 and 291 of HA1 and 18, 19, 20, 21, 38, 41, 42, 45, 49, 52, 53, and 56 of HA2 when the hemagglutinin in the neutral pH conformation.

In some forms the hemagglutinin composition is conjugated (e.g. a chimeric peptide) having one or more peptides or peptide fragments linked to a backbone where peptides or peptide fragments are spatially positioned relative to each other so that they together form a non-linear sequence which mimics the tertiary structure of an F10 epitope, wherein said conjugate competes with the binding of monoclonal antibody F10 to the HA protein. The backbone is a peptide backbone wherein peptides corresponding to segments of native hemagglutinin are coupled to form an epitope mimicking the F10 epitope. Alternatively the peptide backbone mimics the structure of the native hemagglutin protein such that peptides are coupled to for form an epitope mimicking the F10 epitope. Optionally, the backbone is a non-peptide backbone having two or more attachment points onto which peptides are coupled. See, WO9738011, the contents of which are incorporated by reference.

The peptides or peptide fragments that make up the F10 epitope include one or more of the following peptides a) (SEQ ID NO: 130)

$[Xaa_0]_m\text{-}Xaa_1\text{-}Xaa_2\text{-}[Xaa_0]_p$ wherein, m, and p are independently 0 or 1-10,
$Xaa_0$, is independently any amino acid,
  $Xaa_1$ is S, T, F H or Y, and
  $Xaa_2$ is H, Y, M, L or Q;

b) (SEQ ID NO: 131)

$[Xaa_0]_m\text{-}Xaa_1\text{-}Xaa_2\text{-}[Xaa_0]_p$ wherein, m, and p are independently 0 or 1-10,
$Xaa_0$, is independently any amino acid, and
  $Xaa_1$ is H, Q, Y, S, D, N or T,
  $Xaa_2$ is Q, E, K, I, V, M, E, R or T;

c) (SEQ ID NO: 132)

$[Xaa_0]_m\text{-}Xaa_1\text{-}Xaa_2\text{-}Xaa_3\text{-}Xaa_4\text{-}[Xaa_0]_p$ wherein, m, and p are independently 0 or 1-10,
$Xaa_0$, is independently any amino acid, and
  $Xaa_1$ is I, V, M, or L;
  $Xaa_2$ is D, N, H, Y, D, A, S or E,
  $Xaa_3$ is G or A, and
  $Xaa_4$ is W, R, or G; or d) (SEQ ID NO: 133)

$[Xaa_0]_m\text{-}Xaa_1\text{-}[Xaa_0]_q\ Xaa_2\text{-}Xaa_3\text{-}[Xaa_0]_q\ Xaa_4\text{-}$ $[Xaa_0]_r\ Xaa_5\text{-}[Xaa_0]_q\text{-}Xaa_6\ Xaa_7\text{-}[Xaa_0]_q\text{-}Xaa_8\text{-}$ $[Xaa_0]_p$ wherein, m, and p are independently 0 or 1-10, q is 2, and r is 3
$Xaa_0$, is independently any amino acid, and
  $Xaa_1$ is K, Q, R, N, L, G, F, H or Y,
  $Xaa_2$ is S or T,
  $Xaa_3$ is Q or P,
  $Xaa_4$ is F, V, I, M, L, or T,
  $Xaa_5$ is I, T, S, N, Q, D, or A,
  $Xaa_6$ is I, V, M, or L,
  $Xaa_7$ is N, S, T, or D
  $Xaa_8$ is I, F, V, A, or T;

e) (SEQ ID NO: 134)

$[Xaa_0]_m\text{-}Xaa_1\text{-}[Xaa_0]_q\ Xaa_2\text{-}Xaa_3\text{-}[Xaa_0]_q\ Xaa_4\text{-}$ $[Xaa_0]_r\ Xaa_5\text{-}[Xaa_0]_q\text{-}Xaa_6\ Xaa_7\text{-}[Xaa_0]_s\text{-}[Xaa_8]_t\text{-}$ $[Xaa_0]_p$ wherein, m, and p are independently 0 or 1-10, q is 2, r is 3, s is 0 or 2, and t is 0 or 1,
$Xaa_0$, is independently any amino acid, and
  $Xaa_1$ is K, Q, R, N, L, G, F, H or Y,
  $Xaa_2$ is S or T,
  $Xaa_3$ is Q or P,
  $Xaa_4$ is F, V, I, M, L, or T,
  $Xaa_5$ is I, T, S, N, Q, D, or A, Xaa$_6$ is I, V, M, or L,
Xaa$_7$ is N, S, T, or D,
Xaa$_8$ I, F, V, A, or T.

Disclosed is a method, the method comprising screening antibodies reactive to hemagglutinin for binding to hemagglutinin immobilized on a surface, thereby identifying antibodies of interest. For example, disclosed is a method comprising screening antibodies reactive to hemagglutinin for binding to the stem region of influenza hemagglutinin in the neutral pH conformation in isolation from the head region of hemagglutinin, thereby identifying antibodies of interest. For example, disclosed is a method comprising screening antibodies reactive to hemagglutinin for binding to influenza hemagglutinin in the neutral pH conformation in isolation from other components of influenza virus, wherein the head region of the hemagglutinin is modified to reduce the antigenicity of the head region, thereby identifying antibodies of interest.

In some forms, the head region of the hemagglutinin can be modified by removing or replacing glycosylation sites. In some forms, the head region of the hemagglutinin can be modified by adding glycosylation sites. In some forms, the head region of the hemagglutinin can be modified by removing all or a portion of the head region.

Disclosed are antibodies that can be used, identified or produced in the disclosed methods. For example, disclosed are antibodies that bind to the stem region of influenza hemagglutinin in the neutral pH conformation ("HA stem antibodies"). For example, disclosed are antibodies that bind the epitope of influenza hemagglutinin bound by antibody F10. For example, disclosed are antibodies that bind the epitope of influenza hemagglutinin in the neutral pH conformation defined by amino acid residues 18, 38, 39, 40 and 291 of HA1 and 18, 19, 20, 21, 38, 41, 42, 45, 49, 52, 53, and 56 of HA2. For example, disclosed are antibodies that bind the epitope of influenza hemagglutinin in the neutral pH conformation defined by amino acid residues 17, 18, 38, 39, 40 and 291 of HA1 and 18, 19, 20, 21, 38, 41, 42, 45, 49, 52, 53, 56, and 111 of HA2. For example, disclosed are antibodies that bind to every subtype within an influenza virus group.

In some forms, the antibody can compete with antibody F10 for binding to hemagglutinin. In some forms, the antibody can have a VH CDR2 sequence that is the same as the VH CDR2 sequence of antibody D7, D8, F10, G17, H40 or A66 or of the consensus VH sequence SEQ ID NO:1. In some forms, the antibody can have a VH CDR3 sequence that is the same as the VH CDR3 sequence of antibody D7, D8, F10, G17, H40 or A66 or of the consensus VH sequence SEQ ID NO:1. In some forms, the antibody can have a VH CDR1 sequence that is the same as the VH CDR1 sequence of antibody D7, D8, F10, G17, H40 or A66 or of the consensus VH sequence SEQ ID NO:1. In some forms, the antibody can have a VH sequence that is the same as the VH sequence of antibody D7, D8, F10, G17, H40 or A66 or of the consensus VH sequence SEQ ID NO:1. In some forms, the antibody can have a VL sequence that is the same as the VL sequence of antibody D7, D8, F10, G17, H40, A66, D80, E88, E90, or H98 or of the consensus VL sequence SEQ ID NO:2. In some forms, the antibody can have any combination of the VH FR1, VH CDR1, VH FR2, VH CDR2, VH FR3, VH CDR3, and VH FR4 sequences of antibodies D7, D8, F10, G17, H40 and A66 and the consensus VH sequence SEQ ID NO:1, and any combination of the VL FR1, VL CDR1, VL, FR2, VL CDR2, VL FR3, VL CDR3, and VL FR4 sequences of antibodies D7, D8, F10, G17, H40, A66, D80, E88, E90, and H98 and the consensus VL sequence SEQ ID NO:2. In some forms, the antibody can prevent or inhibit virus-host membrane fusion. In some forms, the antibody can prevent or inhibit cell fusion mediated by cell surface-expressed influenza hemagglutinin.

In some forms, the disclosed antibodies, the disclosed hemagglutinins, and the disclosed methods can produce an immune reaction in a subject. For example, in some forms, the subject can produce an immune response that prevents or reduces the severity of an influenza infection. In some forms, the immune response can be reactive to influenza viruses within a subtype. In some forms, the immune response can be reactive to influenza viruses in each subtype within a cluster. In some forms, the immune response can be reactive to influenza viruses in each cluster within a group. In some forms, the immune response can be reactive to all influenza viruses in each subtype within a group. In some forms, the immune response can be reactive to influenza viruses within group 1.

In some forms, the disclosed methods can further comprise screening the antibodies of interest for competing with antibody F10 for binding to hemagglutinin, thereby identifying F10-competing antibodies. In some forms, the hemagglutinin can be hemagglutinin from a group 2 influenza virus. In some forms, the hemagglutinin can be hemagglutinin from a group 1 influenza virus. In some forms, the disclosed methods can further comprising producing the identified antibodies. Also disclosed are antibodies produced by the disclosed methods. Also disclosed are antibodies identified by the disclosed methods.

In some forms, the disclosed methods can further comprise screening a compound of interest, e.g., an F10 mimitope composition for competing with antibody F10 for binding to hemagglutinin, thereby identifying F10 mimitopes. The F10 mimitopes are useful as immunogens. In some forms, the hemagglutinin can be hemagglutinin from a group 2 influenza virus. In some forms, the hemagglutinin can be hemagglutinin from a group 1 influenza virus. Also included in the invention are F10 mimitopes identified by the disclosed methods.

The disclosed antibodies and/or hemagglutinin compositions can be administered to a subject alone or in combination prior to and/or following exposure or possible exposure of the subject to influenza virus. For example, the disclosed antibodies and/or hemagglutinin compositions can be administered to a subject prior to entering an area of infection or suspected infection, prior to coming into the presence of infected subjects or subjects suspected of infection, after entering an area of infection or suspected infection, after coming into the presence of infected subjects or subjects suspected of infection prior to and after entering an area of infection or suspected infection, or prior to and after coming into the presence of infected subjects or subjects suspected of infection.

As used herein the phrase "immune response" or its equivalent "immunological response" refers to the development of a humoral (antibody mediated) and/or a cellular (mediated by antigen-specific T cells or their secretion products) response directed against a target protein or polypeptide in a subject. Such a response can be an active response induced by administration of immunogen (such as the peptide immunogens described herein) or a passive response induced by administration of antibody or primed T-cells. A cellular immune response is elicited by the presentation of polypeptide epitopes in association with Class I or Class II MHC molecules, to activate antigen-specific CD4$^+$ T helper cells and/or CD8$^+$ cytotoxic T cells. The response may also involve activation of monocytes, macrophages, NK, cells, basophils, dendritic cells, astrocytes, microglia cells, eosinophils or other components of innate immunity.

As used herein "active immunity" refers to any immunity conferred upon a subject by administration of an antigen, e.g. the disclosed hemagglutinin compositions As used herein "passive immunity" refers to any immunity conferred upon a subject without administration of an antigen. "Passive immunity" therefore includes, but is not limited to, administration of a an antibody, such as the disclosed antibodies and, for example, a HA stem antibody, or, for example, a replicating display vehicle which includes an immunological portion of an antibody presented on its surface to a subject. Although replication of such a vehicle is active, the immune response is passive from the standpoint of the subject.

Passive immunization has proven to be as effective and safe strategy for the prevention and treatment of viral diseases (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using neutralizing human monoclonal antibodies can provide an immediate treatment strategy for emergency prophylaxis and treatment of influenza such as bird flu as an alternative or in combination with the disclosed vaccines and drugs.

Subunit vaccines offer significant advantages over conventional immunogens. They avoid the safety hazards inherent in production, distribution, and delivery of conventional killed or attenuated whole-pathogen vaccines. Furthermore, they can be rationally designed to include only confirmed protective epitopes, thereby avoiding suppressive T epitopes (see Steward et al., J. Virol. 69:7668 (1995)) or immunodominant B epitopes that subvert the immune system by inducing futile, non-protective responses (e.g. "decoy" epitopes). (See Garrity et al., J. Immunol. 159:279 (1997)). For example, the subunit vaccine comprises the F10 epitope Moreover, those skilled in the art will recognize that good correlation exists between the antibody neutralizing activity in vitro and the protection in vivo for many different viruses, challenge routes, and animal models (See Burton, Natl. Rev. Immunol. 2:706-13 (2002); Parren et al., Adv. Immunol. 77:195-262 (2001)). The data presented herein demonstrate that the D7, D8, F10, G17, H40, A66, D80, E88, E90, and H98 human monoclonal antibodies can the analyzed in in vivo animal studies to confirm its clinical utility as a potent viral entry inhibitor for emergency prophylaxis and treatment of influenza.

Methods for the screening of antibodies that possess the desired specificity include, but are not limited to, enzyme linked immunosorbent assay (ELISA) and other immunologically mediated techniques known within the art.

Antibodies directed against a influenza virus protein such as HA (or a fragment thereof) can be used in methods known within the art relating to the localization and/or quantitation of a influenza virus protein (e.g., for use in measuring levels of the influenza virus protein within appropriate physiological samples, for use in diagnostic methods, for use in imaging the protein, and the like). In some forms, antibodies specific to an influenza virus protein, or derivative, fragment, analog or homolog thereof, that contain the antibody derived antigen binding domain, can be utilized as pharmacologically active compounds (referred to herein as "therapeutics").

An antibody specific for an influenza virus protein can be used to isolate an influenza virus polypeptide by standard techniques, such as immunoaffinity, chromatography or immunoprecipitation. Antibodies directed against an influenza virus protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The disclosed antibodies, including polyclonal, monoclonal, humanized and fully human antibodies, can be used as therapeutic agents. Such agents can generally be employed to treat or prevent an influenza virus-related disease or pathology (e.g., bird flu) in a subject. An antibody preparation, such as, for example, one having high specificity and high affinity for its target antigen, can be administered to the subject and will generally have an effect due to its binding with the target. Administration of the antibody can abrogate or inhibit or interfere with the internalization of the virus into a cell. In this case, the antibody binds to the target and masks a binding site of the naturally occurring ligand, thereby blocking fusion the virus to the cell membrane inhibiting internalization of the virus.

A therapeutically effective amount of an antibody or hemagglutinin composition relates generally to the amount needed to achieve a therapeutic objective. As noted elsewhere herein, this can be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment can be, by way of nonlimiting example, from about 0.1 mg/kg body weight to about 50 mg/kg body weight. Common dosing frequencies can range, for example, from twice daily to once a week.

Antibodies specifically binding an influenza virus protein or a fragment thereof, as well as other molecules identified by the screening assays disclosed herein, can be administered for the treatment of an influenza virus-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances in Parenteral Sciences, Vol. 4), 1991, M. Dekker, New York.

Where antibody fragments are used, it can be useful to use the smallest inhibitory fragment that specifically binds to the binding domain of the target protein. For example, based upon the variable-region sequences of an antibody, peptide molecules can be designed that retain the ability to bind the target protein sequence. Such peptides can be synthesized chemically and/or produced by recombinant DNA technology (See, e.g., Marasco et al., Proc. Natl. Acad. Sci. USA, 90: 7889-7893 (1993)).

The formulation can also contain more than one active compound as necessary for the particular indication being treated, such as, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This can readily be accomplished, for example, by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™0 (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

The disclosed antibodies can be used as agents for detecting the presence of an influenza virus (or a protein or a protein fragment thereof) in a sample. The antibody can contain a detectable label. Antibodies can be, for example, polyclonal or monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term, "biological sample", therefore, is blood and a fraction or component of blood including blood serum, blood plasma, or lymph. That is, the disclosed detection method can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a solid support or display vehicle. For example, beads, microparticles or nanoparticles with hemagglutinin composition bound to the surface can be administered to subjects. Because of the discovery that immobilized hemagglutinin can be bound by antibodies specific for the hemagglutinin stem region, such compositions can be used to generate an immune response in a subject. Such an immune response can produce antibodies and immune system components that can inhibit influenza virus.

As used herein the term "adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages.

A pharmaceutical preparation can include, as an active ingredient, a composition comprising at least one epitope of a target protein or polypeptide, the at least one epitope being capable of eliciting antibodies capable of binding to the stem region of hemagglutinin. Preferably, the at least one epitope is the F10 epitope or F10 epitope unit disclosed herein. Alternatively, a pharmaceutical composition can include, as an active ingredient, a composition comprising at least an immunological portion of an antibody being for binding at least one epitope of the stem region of hemagglutinin.

The preparation can be administered to a subject or organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to a subject or organism.

Herein the term "active ingredient" refers to the preparation accountable for the biological effect.

As used herein, the phrases "physiologically acceptable carrier" and "pharmaceutically acceptable carrier" which can be interchangeably used refer to a carrier or a diluent that does not cause significant irritation to a subject or organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in Remington's Pharmaceutical Sciences, Mack Publishing Co., Eastern, Pa., latest edition, which is incorporated herein by reference.

Suitable routes of administration can, for example, include oral, rectal, transmucosal, especially transnasal, intestinal or parenteral delivery, including intramuscular subcutaneous and intramedullary injections as well as intrathecal, direct intraventricular, intravenous, intraperitoneal, intranasal, or intraocular injections. Alternately, one can administer a preparation in a local rather than systemic manner.

Pharmaceutical compositions can be manufactured by processes well known in the art, e.g., by means of conventional mixing, dissolving, granulating, dragee-making, levigating, emulsifying, encapsulating, entrapping or lyophilizing processes.

Pharmaceutical compositions for use in the disclosed methods thus can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients can be formulated in aqueous solutions, preferably in physiologically compatible buffers such as Hank's solution, Ringer's solution, or physiological salt buffer. For transmucosal administration, penetrants appropriate to the barrier to the permeated are used in the formulation. Such penetrants are generally known in the art.

For oral administration, the compounds can be formulated readily by combining the active compounds with pharmaceutically acceptable carriers well known in the art. Such carriers enable the compounds to be formulated as tablets, pills, dragees, capsules, liquids, gels, syrups, slurries, suspensions, and the like, for oral ingestion by a patient. Pharmacological preparations for oral use can be made using a solid excipient optionally grinding the resulting mixture, and processing the mixture of granules, after adding suitable auxiliaries if desired, to obtain tablets or dragee cores. Suitable excipients are, in particular, filters such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents can be added, such as cross-linked polyvinyl pyrrolidone, agar, or alginic acid or a salt thereof such as sodium alginate.

Dragee cores are provided with suitable coatings. For this purpose, concentrated sugar solutions can be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments can be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules can contain the active ingredients in admixture with filler such as lactose, binders such as starches, lubricants such as talc or magnesium stearate and, optionally, stabilizers. In soft capsules, the active ingredients can be dissolved or suspended in suitable liquids, such as fatty oils, liquid paraffin, or liquid polyethylene glycols. In addition, stabilizers can be added. All formulations for oral administration should be in dosages suitable for the chosen route of administration.

For buccal administration, the compositions can take the form of tablets or lozenges formulated in conventional manner.

For administration by nasal inhalation, the active ingredients for use in the disclosed methods can be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit can be determined by providing a valve to deliver a metered amount. Capsules and cartridges of, e.g., gelatin for use in a dispenser can be formulated containing a powder mix of the compound and a suitable powder base such as lactose or starch.

The preparations described herein can be formulated for parenteral administration e.g., by bolus injection or continuous infusion. Formulations for injection can be presented in unit dosage form, e.g., in ampoules or in multidose containers with optionally, an added preservative. The compositions can be suspensions, solutions, or emulsions in oily or aqueous vehicles, and can contain formulatory agents such as suspending, stabilizing and/or dispersing agents.

Pharmaceutical compositions for parenteral administration include aqueous solutions of the active preparation in water-soluble form. Additionally, suspensions of the active ingredients can be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents which increase the solubility of the active ingredients to allow for the preparation of highly concentrated solutions.

Alternatively, the active ingredient can be in powder form for constitution with a suitable vehicle, e.g., sterile, pyrogen-free water based solution, before use.

The preparations can also be formulated in rectal compositions such as suppositories or retention enemas, using, e.g., conventional suppository bases such as cocoa butter or other glycerides.

Pharmaceutical compositions for use in the disclosed methods include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the disclosed methods, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from those in vitro and cell culture assays and animal studios can be used in formulating a range of dosage for use in human. The dosage may vary depending upon the dosage form employed and the route of administration utilized. The exact formulation, route of administration and dosage can be chosen by the individual physician in view of the patient's condition, (See e.g., Fingl et al in The Pharmacological Basis of Therapeutics, Ch. 1 p. 1. (1975)).

Dosage amount and interval can be adjusted individually to provide plasma of antibodies which are sufficient to prevent or reduce viral entry (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels above the MEC for example, 10-90% of the time, preferable between 30-90% of the time and most preferably 50-90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The disclosed antibodies, hemagglutinin compositions or agents (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Examples of such carriers or diluents include, but are not limited to, water, saline, ringer's solutions, dextrose solution, and 5% human serum albumin. Liposomes and non-aqueous vehicles such as fixed oils can also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition can be formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELÔ (BASF, Parsippany, N.J.) or phosphate buffered saline (PBS). In all cases, the composition must be sterile and should be fluid to the extent that easy syringeability exist. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze drying that yields a powder of the active ingredient plus any additional desired ingredient from a previously sterile filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a gildant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds can be formulated into ointments, salves, gels, or creams as generally known in the art. The compounds can also be prepared in the form of suppositories (e.g., with conventional suppository bases such as cocoa batter and other glycerides) or retention enemas for rectal delivery.

In some forms, the active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for case of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms can be dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The disclosed compositions can, if desired, be presented in a pack or dispenser device, such as an FDA approved kit, which may contain one or more unit dosage forms containing the active ingredient. The pack can, for example, comprise metal or plastic foil, such as a blister pack. The pack or dispenser device can be accompanied by instructions for administration. The pack or dispenser can also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation formulated in a compatible pharmaceutical carrier can also be prepared, placed in an appropriate container, and labeled for treatment of an indicated condition, as if further detailed above.

The term "activity" as used herein refers to a measurable result of the interaction of molecules. Some exemplary methods of measuring these activities are provided herein. The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease to activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

The terms "higher," "increases," "elevates," or "elevation" refer to increases above basal levels, e.g., as compared to a control. The terms "low," "lower," "reduces," or "reduction" refer to decreases below basal levels, e.g., as compared to a control.

Disclosed are methods (also referred to herein as "screening assays") for identifying modulators, i.e., candidate or test compounds or agents (e.g., peptides, peptidomimetics, small molecules or other drugs) that modulate or otherwise interfere with the fusion of an influenza virus to the cell membrane. Also disclosed are methods of identifying compounds useful to treat influenza infection. Also disclosed are compounds identified using the screening assays described herein.

For example, disclosed are assays for screening candidate or test compounds which modulate the interaction between the influenza virus and the cell membrane. Additionally, disclosed are assays for screening candidate or test compounds that compete for binding of hemagglutinin to the antibodies disclosed herein. Compound identified in these methods are useful as immunogens for influenza virus.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (See, e.g., Lam, 1997. Anticancer Drug Design 12: 145).

A "small molecule" as used herein, is meant to refer to a composition that has a molecular weight of less than about 5 kD, such as, for example, less than about 4 kD. Small molecules can be, e.g., nucleic adds, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the known or disclosed assays.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckerman, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds can be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (sec Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In some forms, a candidate compound can be introduced to an antibody-antigen complex and it can be determined whether the candidate compound disrupts the antibody-antigen complex. In some aspects a disruption of this complex indicates that the candidate compound modulates the interaction between an influenza virus and the cell membrane. For example, the antibody can be monoclonal antibody D7, D8, F10, G17, H40, A66, D80, E88, E90, and H98 and the antigen can be located on the HA protein of an influenza virus.

In some forms, at least one HA protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat a an influenza virus-related disease or disorder, e.g. bird flu or swine flu. For example, the at least one influenza virus protein can be provided as an influenza virus molecule.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label, detected by determination of conversion of an appropriate substrate to product.

In some forms, the assay can comprise contacting an antibody-antigen complex with a test compound, and determining the ability of the test compound to interact with the antigen or otherwise disrupt the existing antibody-antigen complex. In some forms, determining the ability of the test compound to internet with the antigen and/or disrupt the antibody-antigen complex can comprise determining the ability of the test compound to preferentially bind to the antigen or a biologically-active portion thereof, as compared to the antibody.

In some forms, the assay can comprise contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody can be a an influenza virus neutralizing antibody, such as monoclonal antibody D7, D8, F10, G17, H40, A66, D80, E88, E90, and H98. Additionally, the antigen can be a HA protein, or a portion thereof. In any of the assays described herein, the ability of a candidate compound to interfere with the binding between the D7, D8, F10, G17, H40, A66, D80, E88, E90, and H98 monoclonal antibody and the HA protein indicates that the candidate compound will be able to interfere with or modulate the fusion of the influenza virus and the cell membrane Moreover, because the binding of the HA protein to cell is responsible for influenza virus entry into cells such candidate compounds will also be useful in the treatment of a influenza virus related disease or disorder, e.g. bird flu.

The screening methods disclosed herein can be performed as a cell-based assay or as a cell-free assay. The cell-free assays are amenable to use of both the soluble form or the membrane-bound form of the HA proteins and fragments thereof. In the case of cell-free assays comprising the membrane-bound forms of the HA proteins, it can be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In some forms, it can be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In some forms, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also the used in the screening assays. For example, either the antibody or the antigen can the immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

Also disclosed are novel agents identified by any of the disclosed screening assays and uses thereof for treatments as described herein.

Antibodies can be detected by appropriate assays, e.g., conventional types of immunoassays. For example, an assay can be performed in which a influenza protein (e.g., HA1, HA 2 or neurominidase) or fragment thereof is affixed to a solid phase. Incubation can be maintained for a sufficient period of time to allow the antibody in the sample to bind to the immobilized polypeptide on the solid phase. After this first incubation, the solid phase can be separated from the sample. The solid phase can be washed to remove unbound materials and interfering substances such as non-specific proteins which may also be present in the sample. The solid phase containing the antibody of interest bound to the immobilized polypeptide can subsequently be incubated with a second, labeled antibody or antibody bound to a coupling agent such as biotin or avidin. This second antibody can be another anti-influenza antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of a influenza virus (in a biological sample, for example) can involve obtaining a biological sample from a test subject and contacting the biological sample with a labeled monoclonal or scFv antibody such that the presence of the influenza virus is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method can be used to detect an influenza virus in a biological sample in vitro as well as in vivo. For example, in vitro techniques for detection of an influenza virus include enzyme linked immunosorbent assays (ELISAs), Western blots, immunoprecipitations, and immunofluorescence. Furthermore, in vivo techniques for detection of an influenza virus include introducing into a subject a labeled anti-influenza virus antibody. For example, the antibody can be labeled with a radioactive marker whose presence and location in a subject can be detected by standard imaging techniques.

In some forms, the biological sample can contain protein molecules from the test subject. The biological sample can be, for example, a peripheral blood leukocyte sample isolated by conventional means from a subject.

Also disclosed are kits for detecting the presence of an influenza virus in a biological sample. For example, the kit can comprise: a labeled compound or agent capable of detecting an influenza virus (e.g., an anti-influenza scFv or monoclonal antibody) in a biological sample; means, materials, and/or a system for determining the amount of an influenza virus in the sample; and means, materials, and/or a system for comparing the amount of an influenza virus in the sample with a standard. The compound or agent can be packaged in a suitable container. The kit can further comprise instructions for using the kit to detect an influenza virus in a sample.

It has been over a decade since the first antibodies were used as scaffolds for the efficient presentation of antigenic determinants to the immune systems. (See Zanetti, Nature 355:476-77 (1992); Zaghouani et al., Proc. Natl. Acad. Sci. USA 92:631-35 (1995)). When a peptide is included as an integral part of an IgG molecule, the antigenicity and immunogenicity of the peptide epitopes are greatly enhanced as compared to the free peptide. Such enhancement can be due to the antigen-IgG chimeras longer half-life, better presentation and constrained conformation, which mimic their native structures.

Moreover, an added advantage of using an antigen-Ig chimera is that either the variable or the Fc region of the antigen-Ig chimera can be used for targeting professional antigen-presenting cells (APCs). Recombinant Igs have been generated in which the complementarity-determining regions (CDRs) of the heavy chain variable gene ($V_H$) are replaced with various antigenic peptides recognized by B or T cells. Such antigen-Ig chimeras have been used to induce both humoral and cellular immune responses (See Bona, et al., Immunol. Today 19:126-33 (1998)).

Chimeras with specific epitopes engrafted into the CDR3 loop have been used to induce humoral responses to either HIV-1 gp120 V3-loop or the first extracellular domain (D1) of human CD4 receptor (See Lanza et al., Proc. Natl. Acad. Sci. USA 90:11683-87 (1993); Zaghouani et al., Proc. Natl. Acad. Sci. USA 92:631-35 (1995)). The immune sera were able to prevent infection of CD4 SupT1 cells by HIV-1MN (anti-gp120 V3C) or inhibit syncytia formation (anti-CD4-D1). The CDR2 and CDR3 can be replaced with peptide epitopes simultaneously, and the length of peptide inserted can be up to 19 amino acids long. Alternatively, one group has developed a "troybody" strategy in which peptide antigens are presented in the loops of the Ig constant (C) region and the variable region of the chimera can be used to target IgD on the surface of B-cells or MHC class II molecules on professional APCs including B-cells, dendritic cells (DC) and macrophages (See Lunde et al., Biochem. Soc. Trans. 30:500-6 (2002)).

An antigen-Ig chimera can also be made by directly fusing the antigen with the Fc portion of an IgG molecule. You et al., Cancer Res. 61:3704-11 (2001) were able to obtain all arms of specific immune response, including very high levels of antibodies to hepatitis B virus core antigen using this method.

DNA vaccines are stable, can provide the antigen an opportunity to be naturally processed, and can induce a longer-lasting response. Although a very attractive immunization strategy, DNA vaccines often have very limited potency to induce immune responses. Poor uptake of injected DNA by professional APCs, such as dendritic cells (DCs), may be the main cause of such limitation. Combined with the antigen-Ig chimera vaccines, a promising new DNA vaccine strategy based on the enhancement of APC antigen presentation has been reported (see Casares, et al., Viral Immunol. 10:129-36 (1997); Gerloni et al., Nat. Biotech. 15:876-81 (1997); Gerloni et al., DNA Cell Biol. 16:611-25 (1997); You et al., Cancer Res. 61:3704-11 (2001)), which takes advantage of the presence of Fc receptors (FcγRs) on the surface of DCs.

It is possible to generate a DNA vaccine encoding an antigen (Ag)-Ig chimera. Upon immunization, Ag-Ig fusion proteins can be expressed and secreted by the cells taking up the DNA molecules. The secreted Ag-Ig fusion proteins, while inducing B-cell responses, can be captured and internalized by interaction of the Fc fragment with FcγRs on DC surface, which will promote efficient antigen presentation and greatly enhance antigen-specific immune responses. Applying the same principle, DNA encoding antigen-Ig chimeras carrying a functional anti-MHC II specific scFv region gene can also target the immunogens to all three types of APCs. The immune responses could be further boosted with use of the same protein antigens generated in vitro (i.e., "prime and boost"), if necessary. Using this strategy, specific cellular and humoral immune responses against infection of influenza virus were accomplished through intramuscular (i.m.) injection of a DNA vaccine (See Casares et al., Viral. Immunol. 10:129-36(1997)).

Therapeutic or prophylactic compositions are provided herein, which can comprise, for example, mixtures of one or more hemagglutinin compositions, monoclonal antibodies or ScFvs and combinations thereof. The prophylactic vaccines can be used to prevent an influenza virus infection and the therapeutic vaccines can be used to treat individuals following an influenza virus infection. Prophylactic uses include the provision of increased antibody titer to an influenza virus in a vaccination subject and or decrease influenza virus titer in a subject. In this manner, subjects at high risk of contracting influenza can be provided with passive immunity to an influenza virus.

These vaccine compositions can be administered in conjunction with ancillary immunoregulatory agents. For example, cytokines, lymphokines, and chemokines, including, but not limited to, IL-2, modified IL-2 (Cys125→Ser125), GM-CSF, IL-12, γ-interferon, IP-10, MIP1β, and RANTES.

The disclosed vaccines have superior immunoprotective and immunotherapeutic properties over other anti-viral vaccines. Also disclosed is a method of immunization, e.g., inducing an immune response, of a subject. A subject can be immunized by administration to the subject a composition containing a membrane fusion protein of a pathogenic enveloped virus. The fusion protein can be coated or embedded in a biologically compatible matrix.

The fusion protein can be glycosylated, e.g. can contain a carbohydrate moiety. The carbohydrate moiety can be in the form of a monosaccharide, disaccharide(s), oligosaccharide(s), polysaccharide(s), or their derivatives (e.g. sulfo- or phospho-substituted). The carbohydrate can be linear or branched. The carbohydrate moiety can be N-linked or O-linked to a polypeptide. N-linked glycosylation is to the amide nitrogen of asparagine side chains and O-linked glycosylation is to the hydroxy oxygen of serine and threonine side chains.

The carbohydrate moiety can be endogenous to the subject being vaccinated. Alternatively, the carbohydrate moiety can be exogenous to the subject being vaccinated. The carbohydrate moieties can be carbohydrate moieties that are not typically expressed on polypeptides of the subject being vaccinated. For example, the carbohydrate moieties can be plant-specific carbohydrates. Plant specific carbohydrate moieties include for example N-linked glycan having a core bound α1,3 focose or a core bound β1,2 xylose. Alternatively, the carbohydrate moieties can be carbohydrate moieties that are expressed on polypeptides or lipids of the subject being vaccinate. For example many host cells have been genetically engineered to produce human proteins with human-like sugar attachments.

For example, the fusion protein can be a trimeric hemagglutinin protein. Optionally, the hemagglutinin protein can be produced in a non-mammalian cell such as a plant cell.

The subject can be at risk of developing or suffering from a viral infection. Enveloped viruses include for example, epstein-barr virus, herpes simplex virus, type 1 and 2, human cytomegalovirus, human herpesvirus, type 8, varicella zoster virus, hepatitis B virus, hepatitis C virus, human, immunodeficiency virus, influenza virus, measles virus, mumps virus, parainfluenza virus, respiratory syncytial virus, rabies virus, and rubella virus.

The methods described herein lead to a reduction in the severity or the alleviation of one or more symptoms of a viral infection. Infections can be diagnosed and or monitored, typically by a physician using standard methodologies A subject requiring immunization can be identified by methods know in the art. For example subjects can be immunized as outlined in the CDC's General Recommendation on Immunization (51(RR02) pp 1-36) Cancer is diagnosed for example by physical exam, biopsy, blood test, or x-ray.

The subject can be e.g., any mammal, e.g., a human, a primate, mouse, rat, dog, cat, cow, horse, pig, a fish or a bird. The treatment ican be administered prior to diagnosis of the infection. Alternatively, treatment can be administered after diagnosis.

Efficaciousness of treatment can be determined in association with any known method for diagnosing or treating the particular disorder or infection. Alleviation of one or more symptoms of the disorder indicates that the compound confers a clinical benefit.

A vaccine candidate targeting humoral immunity can fulfill at least three criteria to be successful: provoke a strong antibody response ("immunogenicity"); a significant fraction of the antibodies it provokes must cross-react with the pathogen ("immunogenic fitness"); and the antibodies it provokes must be protective. While immunogenicity can often be enhanced using adjuvants or carriers, immunogenic fitness and the ability to induce protection (as evidenced by neutralization) are intrinsic properties of an antigen which will ultimately determine the success of that antigen as a vaccine component.

"Immunogenic fitness" is defined as the fraction of antibodies induced by an antigen that cross-react with the pathogen (See Matthews et al., J. Immunol. 169:837 (2002)). It is distinct from immunogenicity, which is gauged by the titer of all of the antibodies induced by an antigen, including those antibodies that do not cross-react with the pathogen. Inadequate immunogenic fitness has probably contributed to the disappointing track record of peptide vaccines to date. Peptides that bind with high affinity to antibodies and provoke high antibody titers frequently lack adequate immunogenic fitness, and, therefore, they fail as potential vaccine components. Therefore, it can be useful to include immunogenic fitness as one of the criteria for selecting influenza vaccine candidates.

A common explanation for poor immunogenic fitness is the conformational flexibility of most short peptides. Specifically, a flexible peptide may bind well to antibodies from patients, and elicit substantial antibody titers in naïve subjects. However, if the peptide has a large repertoire of conformations, a preponderance of the antibodies it induces in naïve subjects may fail, to cross-react with the corresponding native epitope on intact pathogen.

Like short peptides, some APFs may be highly flexible and, therefore may fail as vaccine components. The most immunogenically fit APFs are likely to consist of self-folding protein subdomains that are intrinsically constrained outside the context of the whole protein.

Because immunogenic fitness is primarily a property of the APF itself, and not of the responding immune system, immunogenic fitness can be evaluated in an animal model (e.g. in mice) even though ultimately the APF will have to perform in humans.

The immunogenic fitness achieved by APFs can be evaluated by immunosorption of anti-APF sera with purified spike or membrane protein, in a procedure analogous to that described in Matthews et al., J. Immunol. 169:837 (2002). IgG is purified from sera collected from mice that have been immunized. Purified biotinylated proteins (as appropriate, depending on the particular APF with which the mice were immunized) can be mixed with the mouse IgG and incubated. Streptavidin-coated sepharose beads can then be added in sufficient quantity to capture all of the biotinylated protein, along with any bound IgG. The streptavidin-coated beads are removed by centrifugation at 13,000 rpm in a microcentrifuge, leaving IgG that has been depleted of antibodies directed against the protein, respectively. Mock immunoabsorptions can be performed in parallel in the same way, except that biotinylated BSA will be substituted for influenza protein as a mock absorbent.

To measure the immunogenic fitness of APFs, the absorbed antibodies and the mock-absorbed antibodies can be titered side-by-side in ELISA against the immunizing APF. For APFs affinity selected from a phage display NPL, the antigen for these ELISAs can be purified APF-GST fusion proteins. For the potentially glycosylated APFs from the mammalian cell display NPL, the antigen for these ELISAs can be APF-Fc fusion proteins secreted by mammalian cells and purified with protein A. The percentage decrease in the anti-APF titer of absorbed antibodies compared with the mock-absorbed antibodies can provide a measure of the immunogenic fitness of the APF.

Also disclosed are both prophylactic and therapeutic methods of treating a subject at risk of (or susceptible to) an influenza virus-related disease or disorder. Such diseases or disorders include but are not limited to, e.g., bird flu.

Also disclosed are methods for preventing an influenza virus-related disease or disorder in a subject by administering to the subject a hemagglutinin composition, a monoclonal antibody or scFv antibody of the invention or an agent identified according to the methods of the invention. For example, hemagglutinin compositions, scFv and/or monoclonal antibody D7, D8, F10, G17, H40, A66, D80, E88, E90, and H98 can be administered in therapeutically effective amounts. Optionally, two or more anti-influenza antibodies are co-administered.

Subjects at risk for an influenza virus-related diseases or disorder include patients who have come into contact with an infected person or who have been exposed to the influenza virus in some other way. Administration of a prophylactic agent can occur prior to the manifestation of symptoms characteristic of the influenza virus-related disease or disorder, such that a disease or disorder is prevented or, alternatively, delayed in its progression.

The appropriate agent can be determined based on screening assays described herein. Alternatively, or in addition, the agent to be administered can be a scFv or monoclonal antibody that neutralizes an influenza virus that has been identified according to the known or disclosed methods.

Also disclosed are methods of treating an influenza virus-related disease or disorder in a patient. In some forms, the method involves administering an agent (e.g., an agent identified by a screening assay described herein and/or an scFv antibody or monoclonal antibody identified according to known or disclosed methods), or combination of agents that neutralize the influenza to a patient suffering from the disease or disorder.

Also disclosed is a method of treating an influenza-related disease or disorder, such as bird flu or swine flu in a patient by administering two or more antibodies, such as D7, D8, F10, G14, H40, A66, D80, E88, E90, and H98 that bind to the same epitope of the HA protein.

The disclosed subject matter is further described in the following examples, which do not limit the scope of the invention as described in the claims.

EXAMPLES

A. Example 1: Isolation and Analysis of Neutralizing Antibodies to Hemagglutinin Stem Region In this example, a phage-display antibody library and recombinant H5 trimeric ectodomain were used to isolate a group of high-affinity neutralizing mAbs ("nAbs") that were potent inhibitors of H5N1 viral infection in vitro and in vivo. Based on crystallographic and functional studies, it was shown that the nAbs bind to a common epitope—a highly conserved pocket in the stem region of HA containing the "fusion peptide"—that rationalizes their ability to block membrane fusion rather than cell attachment. Sequence and structural analysis of all 16 HA subtypes points to the existence of just two variants of this epitope, corresponding to the two classic phylogenetic groupings of HA (Groups 1 and 2). Eight further Group 1 HA subtypes were tested and demonstrated a remarkable and unprecedented cross-subtype binding and/or neutralization spectrum. Since a Group 1 subtype (H5) was used for panning, the nAbs, as expected, failed to neutralize a Group 2 subtype, H7. These results nevertheless indicate that a cocktail comprising a small subset of nAbs raised against representatives of the two groups can provide broad protection against all seasonal and pandemic influenza A viruses.

1. Methods i. Crystallization of the H5-F10 Complex

H5-F10 complexes were formed by incubating the two purified components with an excess of F10, and isolated by Superdex 200 in TBS buffer. Peak fractions were pooled and concentrated to ~11 mg ml$^{-1}$. The integrity of the H5 trimer was examined using Gel filtration and SDS-PAGE. Crystals grew at 22° C. by equilibrating equal volumes of protein and reservoir solution (12.5% PEG 1K (w/v), 25% ethylene glycol (w/v), 10 mM Tris, pH 8.5) using the hanging drop vapor diffusion technique.

ii. Data Collection, Structure Determination, and Refinement

Diffraction data were collected from crystals flash-frozen at 100K in the reservoir buffer at the Stanford Synchrotron Radiation Laboratory beam-line 9.2, set at a wavelength of 1.0 Å, and processed with XDS (Kabsch, Automatic processing of rotation diffraction data from crystals of initially unknown symmetry and cell constants. *Journal of Applied Crystallography* 26, 795-800 (1993)) and HKL2000 (Otwinowski & Minor, Processing of X-ray diffraction data collected in oscillation mode, in *Methods in Enzymology, Volume* 276: *Macromolecular Crystallography, Part A* (eds. Carter Jr. & Sweet) 307-326 (Academic Press, New York, 1997)). The structure was solved at 3.2 Å resolution by molecular replacement with PHASER using the structures of H5 (A/Vietnam/1194/04; PDB code 2IBX) and a homology model of F10 based on the structure of SARS nAb 80R (PDB code 2GHW) (Hwang et al., Structural basis of neutralization by a human anti-severe acute respiratory syndrome spike protein antibody, 80R, *J Biol Chem* 281, 34610-6 (2006); Rodriguez et al., Homology modeling, model and software evaluation: three related resources. *Bioinformatics* 14, 523-8 (1998)) as starting models. The asymmetric unit contains two H5 trimers and three F10 molecules per trimer, and was refined using REFMAC5 (Murshudov et al., Refinement of macromolecular structures by the maximum-likelihood method. *Acta Crystallogr D Biol Crystallogr* 53, 240-55 (1997)) with simulated annealing to CNS (Murshudov et al. (1997)) and manual rebuilding with Coot (Emsley & Cowtan, Coot: model-building tools for molecular graphics. *Acta Crystallogr D Biol Crystallogr* 60, 2126-32 (2004)) and Xtalview (McRee, A visual protein crystallographic software system for X11/Xview. *Journal of Molecular Graphics* 10, 44-46 (1992)). The final maps are of high quality, and key features such as the F10 CDR loops and interfacial residues are unambiguous and consistent in the 6 copies. The final model includes 503/503/503/497/497/497 residues for the 6 independent copies of H5, 235/235/236/233/234/234 residues for the 6 F10scFvs, 24 N-acetyl-D-glucosamine and 6 β-D-mannose units, but no water molecules. The R$_{FREE}$ is 0.29 with excellent geometry as assessed with PROCHECK (Laskowski et al., PROCHECK: a program to check the stereochemical quality of protein structures. *Journal of Applied Crystallography* 26, 283-291 (1993)) and Rampage (Table 1): percentage of residues in favored, allowed and outlier regions are 90.0%, 9.5%, and 0.5%, respectively,

TABLE 1

Data collection and refinement staistics for H5-F10.

| Table 1A | Native H5-F10 |
|---|---|
| Data Collection | |
| Space group | C2 |
| Cell dimensions | |
| a, b, c (Å) | 205., 119., 339. |
| α, β, γ (°) | 90, 99.6, 90 |
| Resolution (Å) | 3.2(3.28-3.20) * |
| $R_{merge}$ | 0.13(0.81) |
| I/σI | 9.5(2.0) |
| Completeness (%) | 85(68) |
| Redundancy | 4.5(4.5) |
| Refinement | |
| Resolution (Å) | 50-3.2(3.28-3.20) |
| No. reflections | 106885 |
| $R_{work}/R_{free}$ | 0.23(0.32)/0.29(0.38) |
| No. atoms | |
| Protein | 34573 |
| Carbohydrate | 402 |
| Water | 0 |
| B-factors | |
| Protein | 83.5 |
| Carbohydrate | 123.7 |
| Water | N/A |
| R.m.s. deviations | |
| Bond lengths (Å) | 0.010 |
| Bond angles (°) | 1.31 |

| Table IB | H5-F10 |
|---|---|
| Data Collection | |
| Cell parameters | a = 205.3, b = 118.5, c = 338.9 β = 99.6° |
| Space group | C2 |
| Resolution (Å)* | 3.2(3.28-3.20) |
| Total reflections | 509705 |
| Unique reflection | 112570 |
| Completeness (%)* | 85.0 (68.4) |
| Average I/σ(I)* | 9.5 (2.0) |
| $R_{MERGE}$ (%)* | 12.8 (81.0) |
| Redundancy* | 4.5 (4.5) |
| σ cutoff | −3 |
| Refinement | |
| Resolution | 50-32(3.28-3.20) |
| $R_{WORK}$* | 0.23 (0.32) |
| $R_{FREE}$ (5% data)* | 0.29 (0.38) |
| RMSD bond distance (Å) | 0.01 |
| RMSD bond angle (°) | 1.31 |
| Average B value | 75.7 |
| Solvent atoms | 0 |
| σ cutoff | none |
| Ramachandran plot | |
| Residues in favored regions (%) | 90.0 |
| Residues in allowed regions (%) | 9.5 |
| Residues in outlier regions (%) | 0.5 |

A single crystal used for both structure determination at 3.2-Å resolution and refinement.
*Values in parentheses are for highest-resolution shell.

iii. Phage Display Library Selection

Recombinant trimeric H5-VN04 ectodomain was produced for crystallization studies (see below) except that furin co-infection to ensure complete activation was not employed. Abs were identified by two-rounds of selection of a 27 billion member human scFv phage display library against recombinant trimeric H5 immobilized on Immunotube (Nunc), followed by ELISA screening. Ten unique anti-H5 Abs were identified by sequence analysis of 97 H5-positive clones out of 392 clones screened.

iv. Plaque Reduction Assay

H5-VN04, H5-IN05 or A/Netherland/219/03 (H7N7) (H7-NL03) viruses (10,000 pfu) were incubated with anti-H5 scFv-Fcs at three different concentrations (1, 10 or 100 μg $mL^{-1}$) at 37° C. For 30 mins. The virus-Ab mixture was diluted logarithmically and transferred onto MDCK cell monolayers in 12-well plates and incubated at 37° C. for 1 h. Cells were then washed and overlaid with agar. After 4 days of incubation, the overlay was discarded, and plaques visualized by crystal violet staining.

v. Microneutralization Assay

The method was performed as described previously (Rowe et al., Detection of antibody to avian influenza A (H5N1) virus in human serum by using a combination of serologic assays. *J Clin Microbiol* 37, 937-43 (1999)). Briefly, 100 $TCID_{50}$ (median tissue culture infectious doses) of virus were mixed in equal volume with two-fold serial dilutions of Ab stock solution (0.1 mg $ml^{-1}$) in 96-well tissue culture plates, and incubated for 1 h at 37° C. Indicator MDCK cells ($1.5\times10^4$ cells per well) were added to the plates, followed by incubation at 37° C. for 20 h. To establish the endpoint, cell monolayers were then washed with PBS, fixed in acetone, and viral antigen detected by indirect ELISA with a mAb against influenza A NP (A-3, Accurate).

vi. Viral Binding Inhibition Assay $0.5\times10^6$ 293T cells were incubated with H5-TH04-pseudotyped HIV viruses (~500 ng of p24) in the presence of anti-H5 nAbs, control mAbs, or in the absence of antibodies, in PBS buffer containing 0.5% (w/v) BSA and 0.02% (w/v) $NaN_3$ at 4° C. After 1 h incubation, cells were spun down. Supernatants were collected and tested for p24 levels using an HIV-1 $p24^{CA}$ capture ELISA kit (NCI, Frederick, NIH) to quantify unbound virus. Cells were then washed once or twice and lysed to quantify the cell-bound virus using the same method.

vii. Cell Fusion Inhibition Assay

HeLa cells, ~90% confluent in six-well plates, were transfected with pcDNA3.1-H5-TH04 plasmid (3 μg total DNA per well) using lipofectamine 2000 (Invitrogen). After ~30 hours of transfection, the culture medium was supplemented with 1 ml of anti-H5 or control mAbs for 1-2 hours, and cells were then washed and incubated with low-pH fusion buffer (150 mM NaCl+10 mM HEPES, adjusted to pH 5.0) for 4-5 mins. Cells were then returned to the standard culture medium for 2-3 hours at 37° C., and finally fixed with 0.25% (v/v) glutaraldehyde and stained with 0.1% (w/v) crystal violet. Photomicrographs were taken at 10× magnification.

viii. Prophylactic Therapeutic Efficacy Studies in Mice

Female 8-10 weeks old BALB/c mice were used in all experiments. Mice were weighed on the day of virus challenge and then daily for 2 weeks. Body weight was used as the clinical endpoint; mice with body weight loss ≥25% of pre-infection values were euthanized. Animal studies were conducted per approved Institutional Animal Care and Use Committee protocols.

a. Prophylactic Efficacy Study

Three human nAbs (D8-IgG1, F10-IgG1 and A66-IgG1) or control human mAb 80R-IgG1 (Sui et al. (2004)) at 2.5 mg kg$^{-1}$ or 10 mg kg$^{-1}$ were administered into 4 groups of 5 mice each by i.p. injection in 0.5 mL volume. One hour after mAb administration, two groups of mice were challenged with H5-VN04 and two groups with H5-HK97 by i.n. inoculation with 10 MLD$_{50}$ in 50 µl volumes per mouse. Mice were observed and weighed daily for two-weeks after infection. Analogous studies were performed to evaluate the protective efficacy of the nAbs against A/Puerto Rico/8/1934 (H1N1) or A/WSN/1933 (H1N1) viruses.

b. Post-Exposure Therapy Efficacy Study

The experimental design recapitulates the prophylaxis study, with the following exceptions. Twelve groups of 10 mice were first inoculated i.n. with 10 MLD$_{50}$ of VN04. At 24, 48 and 72 hours after H5-VN04 infection, one group of mice received i.p. injections of 15 mg kg$^{-1}$ body weight of one of the three nAbs or control (80R).

ix. Expression and Preparation of Various HA Proteins for Panning

HA1 is an N-terminal fragment of HA of H5N1 A/Thailand/2(SP-33)/2004 (H5-TH04), residues 11 to 325 (H3 numbering). The gene was codon-optimized and expressed as fusion protein with a C-terminal 9 amino-acids tag (C9-tag:GTETSQVAPA (SEQ ID NO: 135)). The fusion protein HA1-C9 was expressed in 293T cells transiently and the secreted proteins in supernatant were harvested 48 hours after transfection and purified from the supernatant by affinity chromatography using Protein A Sepharose that coupled covalently with anti-C9 antibody 1D4 (National Cell Culture Center). The method to produce HA0 protein of H5-VN04 is the same as described below for crystallization of H5-F10 complex but without the baculovirus coinfection for furin-cleavage.

x. Epitope Mapping of Anti-HA5 Antibodies D8, F10, and A66

All the mutants of pcDNA3.1-H5-TH04 were constructed by the QuikChange method (Stratagene, La Jolla, Calif.). Various full-length wild type HA and HA mutants expressing plasmids of H1, H5 or H7 were transfected transiently into 293T cells. 24 hours after transection, cells were harvested for immunostaining. Anti-H5 or control mAb 80R (Sui et al., Potent neutralization of severe acute respiratory syndrome (SARS) coronavirus by a human mAb to S1 protein that blocks receptor association. Proc Natl Acad Sci USA 101, 2536-41 (2004)) at 10 μg/mL or ferret anti-H5N1 serum at 1:300 were incubated with transacted 293T cells at 4° C. for 1 hour. Cells were then washed three times with PBS containing 0.5% BSA and 0.1% $NaN_3$. FITC-labeled goat anti-human IgG (Pierce Biotech., Rockford, Ill.) or FITC-labeled goat anti-ferret IgG (Bethyl, Montgomery, Tex.) were then added to cells and incubated for 30 mins at 4° C. Cells were washed as above, and binding of antibodies to cells was analyzed using a Becton Dickinson FACScalibur with CellQuest software.

xi. Expression and Preparation Phages-scFvs, Soluble scFv-Fcs and Full-Length Human IgG1

Phage-scFvs of individual clones were produced as described previously (Sui et al., Potent neutralization of severe acute respiratory syndrome (SARS) coronavirus by a human mAb to S1 protein that blocks receptor association. Proc Natl Acad Sci USA 101, 2536-41 (2004)). scFv-Fcs and whole human IgG1 were produced as described previously (Sui et al., Potent neutralization of severe acute respiratory syndrome (SARS) coronavirus by a human mAb to S1 protein that blocks receptor association. Proc Natl Acad Sci USA 101, 2536-41 (2004); Gould et al., Protective and therapeutic capacity of human single-chain Fv-Fc fusion proteins against West Nile virus. J Virol 79, 14606-13 (2005); Reff et al., Depletion of B cells in vivo by a chimeric mouse human monoclonal antibody to CD20. Blood 83, 435-445 (1994)). In brief, selected scFvs were converted to scFv-Fcs by subcloning the scFv into an Fc expression vector pcDNA 3.1-Hinge which contains the hinge, CH2, and CH3 domains of human IgG1 but lacks CH1. For whole human IgG1s, the VH and VL gene fragments of scFv were separately subcloned into human IgG1 kappa light chain or lambda light chain expression vector TCAE5 or TCAE6 (Reff et al., Depletion of B cells in vivo by a chimeric mouse human monoclonal antibody to CD20. Blood 83, 435-445 (1994)). scfv-Fcs or IgG1s were expressed in 293T or 293F cells (Invitrogen) by transient transfection and purified by protein A sepharose affinity chromatography.

xii. ELISA 0.2 μg of pure H5 HA proteins was coated onto 96-well Maxisorb ELISA plate (Nunc, NY) at 2 μg/mL in PBS at 4° C. overnight. The plate was washed with PBS for 3 times to remove uncoated proteins. For regular ELISA, 1 μg/mL of anti-H5 scFv-Fcs followed by HRP-anti-human IgG1 were used to detect the binding of anti-H5 scFv-Fcs to H5 HA proteins. For competition ELISA, 50 μL($10^{12}$ pfu) of anti-H5 phage-scFvs were mixed with 5 μg/mL of anti-H5 scFv-Fcs and applied to H5-VN04 HA coated ELISA plate. The competition of scFv-Fcs for the binding of phage-scFvs to HA0 were determined by measuring the remaining binding of phage-scFvs using HRP-anti-M13. The optical density at 450 nm was measured after incubation of peroxidase tetramethylbenzidine (TMB) substrate system (KPL, Gaithersburg Md.)).

xiii. Surface Plasmon Resonance (SPR) Analysis

Kinetic analyses of H5 HA mAbs binding to recombinant H5-VN04 HA0 trimer were performed on a Biacore T100 (Biacore, Sweden) at 25° C. Anti-human IgG Fc antibody (Biacore) was covalently attached to individual flow cell surfaces of a CM4 sensor chip by amine-coupling using the amine coupling kit (Biacore). HA mAbs were captured onto anti-human IgG Fc surfaces (flow rate of 10 μl/min in HBS buffer (Biacore)) to ensure that mAb-H5 binding occurred as a homogenous 1:1 Langmuir interaction. H5 was injected over each flow cell at a flow rate of 30 μl/min in HBS buffer, and at concentrations ranging from to 0.31 to 20 nM. A buffer injection served as a negative control. All experiments contained an additional anti-human IgG Fc antibody control surface that served to account for changes in the buffer refractive index and to test for potential nonspecific interactions between H5 and anti-human IgG Fc. Upon completion of each association and dissociation cycle, surfaces were regenerated with 3 M MgCl$_2$ solution. The association rates (kα), dissociation rates (kd), and affinity constants ($K_D$) were calculated using Biacore T100 evaluation software. The quality of each fit was based on the agreement between experimental data and the calculated fits, where the Chi$^2$ values were below 1.0. Surface densities of mAbs against H5 were optimized to minimize mass transfer and avoid any contribution of avidity effects. All kα, kd, $K_D$ values reported here represent the mean and standard error of three experiments, xiv. Haemagglutination Inhibition (HI) Assay The HI test was performed as previously described (Donald & Isaacs, Counts of influenza virus particles. J Gen Microbiol 10, 457-64 (1954)). Briefly, H5N1/PR8 (Subbarao et al., Evaluation of a genetically modified reassortant H5N1 influenza A virus vaccine candidate generated by plasmid-based reverse genetics. Virology 305, 192-200 (2003)). H5-VN04 and HI-PR34 viruses were mixed with Log 2 antibody dilutions in PBS and iucubated at 20-22° C. for 30 minutes. A 0.5% suspension of turkey erythrocytes was added to each well and the mixture incubated for 30 min at RT before visual scoring for haemagglutination activity.

xv. Expression, Purification, and Crystallization of the 115-F10 Complex

The gene encoding single chain (VH-linker-VL) F10 (scFv) was cloned into pSynI vector containing an N-terminal periplasmic secretion signal pelB, and a C-terminal 6xHis tag (SEQ ID NO: 136). F10 scFv was expressed in XL10 cells in 2YT media containing 0.1% glucose (w/v) at 25° C. for 15 hours with 0.5 mM IPTG. Protein was purified first by Hisbind Ni-NTA (Novagen) according to the manufacturer's instructions, and then by Superdex 200 (Amersham Biosciences) in 50 mM Tris-HCl, 0.5 M NaCl, pH 8.

The ectodomain of H5-VN04 HA gene was expressed in insect cells as a fusion protein by adapting the protocol described previously (Stevens et al., Structure and receptor specificity of the hemagglutinin from an H5N1 influenza virus. Science 312, 404-10 (2006)). This construct contains a C-terminal trimerizing 'foldon' sequence from the bacteriophage T4 fibritin to stabilize the trimeric structure, followed by a thrombin site and a His$_6$ tag (SEQ ID NO: 136). The cDNA of the fusion protein was cloned into the baculovirus transfer vector, pAcGP67A (BD Biosciences, Bedford, Mass.), to allow for efficient secretion of recombinant protein. To obtain fully cleaved HA (as HA1-HA2 trimers), sf9 cells were co-infected with baculovirus stocks of HA0 and furin at an empirically derived ratio. The furin cDNA was a gift from Dr. Robert Fuller (University of Michigan). Three days after infection, the cells were spun down and the supernatant was incubated with Ni-NTA beads (Qiagen Inc., Valencia, Calif.). The beads were washed with TBS buffer (10 mM Tris.HCl, 80 mM NaCl, pH8.0) with 10 mM imidazole, and eluted with TBS with 250 mM Imidazole. The eluted H5 protein was dialyzed against TBS buffer and further purified by ion-exchange using Mono Q HR10/10 column (GE Healthcare, Piscataway, N.J.). The purified H5 was digested by thrombin overnight and further purified by Superdex 200 column in TBS buffer.

Figure 9:
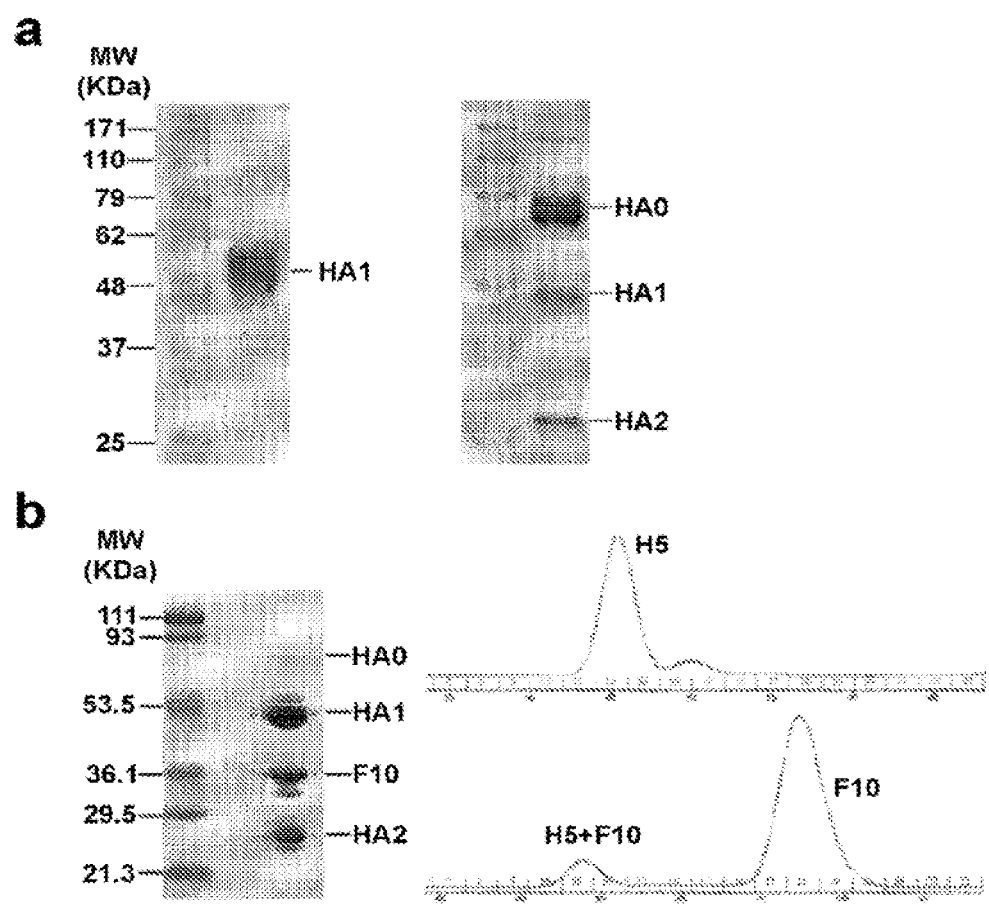
FIGS. 9A and 9B show SDS-PAGE and gel filtration analysis of HA proteins. (A) Antibody 2A was obtained from a separate HA1-targeted selection against the HA1 (residues 11-325) fragment of H5-TH04 (left panel). H5 HA (H5-VN04 strain) used for library selection is shown in the right panel, (B) H5-VN04 (H5) and scFv F10 complex. HA0 was fully cleaved into HA1 and HA2 by co-expression with furin (left panel). Complexes were formed by first mixing H5 and F10 at a molar ratio of 1:10, and then purified by gel filtration.

H5-F10 complexes were formed by mixing the two purified components, and isolated by Superdex 200 in TBS buffer (FIG. 9B). Peak fractions were pooled and concentrated to ~1 mg/ml. The integrity of the H5 trimer was examined using Gel filtration (Superdex 200 column) and SDS-PAGE, Crystals grew by the hanging drop vapor diffusion method at 22° C. Two μL of H5-F10 were mixed with an equal volume of 12.5% PEG 1K, 25% ethylene glycol, 100 mM Tris, pH 8.5. Crystals were flash-frozen in liquid nitrogen prior to data collection.

xvi. Data Collection, Structure Determination, and Refinement

X-ray diffraction data were collected at the Stanford Synchrotron Radiation Laboratory (SSRL) beam-lines 7.1 and 9.2. Data were processed with XDS (Kabsch, Automatic processing of rotation diffraction data from crystals of initially unknown symmetry and cell constants. J. Appl Cryst 26, 795-800 (1993)) and the HKL2000 package (Otwinowski & Minor, in Macromolecular Crystallography, part A (ed. C. W. Carter, J. R. M. S.) 307-326. (Academic Press (New York), 1997)).

The structure of the H5-F10 complex was determined by molecular replacement with PHASER using the structure of H5 (A/Vietnam/1194/04; PDB code 2IBX) and the scFv structure of SARS nAb 80R (PDB code 2GHW) as search models. The scFv structure homology model was build with WHATIF (Rodriguez et al., Homology modeling, model and software evaluation: three related resources. CABIOS 14, 523-528 (1998)). The asymmetric unit contains two H5 trimers and six F10 molecules.

Solutions from molecular replacement were subjected to several rounds of refinement with the program REFMAC5 (Murshudov et al., Refinement of Macromolecular Structures by the Maximum-Likelihood Method. Acta Cryst D53, 240-255 (1997)) with simulated annealing in CNS (Murshudov et al. (1997)) and manual model rebuilding with Coot (Emsley & Cowtan, Model-Building Tools for Molecular Graphics. Acta Crystallographica Section D—Biological Crystallography 60, 2126-2132 (2004)) and Xtalview (McRee, A visual protein crystallographic software system for X11/XView. J. Molecular Graphics 10, 44-46 (1992)). The final model includes 506/503/503/496/495/496 residues for 6 independent copies of HA, respectively, 233 residues for each nAb10, 24 N-acetyl-d-glucosamine and 6 β-d-mannose, 0 water molecules. Geometric parameters were assessed with PROCHECK (Morris et al., A program to check the stereochemical quality of protein structures. J. Appl Cryst 26, 283-291 (1993)) and Rampage.

Accession codes. Protein Data Bank: Coordinates and structure factors for the H5-F10 complex have been deposit with codes PDB ID 3FKU and RCSB ID RCSB050713.

2. Results i. Identification of nAbs Against H5N1

The current H5N1 epidemics involve viruses derived from a single lineage of H5 HA. Within this lineage, four distinct clades have been identified as major threats to public health (W.H.O. web site who.int/csr/disease/avian_influenza/guidelines/summaryH520070403.pdf (2007); W.H.O. Evolution of H5N1 avian influenza viruses in Asia. Emerg Infect Dis 11, 1515-21 (2005)). Recombinant trimeric ectodomain of H5 HA from one of these viruses (strain A/Vietnam/1203/04 (H5N1), "H5-VN04", Clade 1) was expressed in insect cells (Stevens et al., Structure and receptor specificity of the hemagglutinin from an H5N1 influenza virus. *Science* 312, 404-10 (2006)) (FIG. 9), immobilized it on a plastic surface, and selected Abs from a "non-immune" human Ab phage display library (utilizing single-chain VH-VL fragments ("scFv")) (Sui et al., Potent neutralization of severe acute respiratory syndrome (SARS) coronavirus by a human mAb to S1 protein, that blocks receptor association. *Proc Natl Acad Sci USA* 101, 2536-41 (2004)). Two rounds of panning and the screening of 392 clones identified 10 unique Abs that were formed by six distinct VH (variable region of heavy chain) fragments in combination with seven different VL (variable region of light chain) fragments (Table 2).

Table 2 shows framework regions 1-4 (FR1-4) and complementarity-determining regions 1-3 (CDR1-3) for both the VH and VL are shown. FR and CDR regions are defined using the Kabat database. The VH and VL gene names are shown on the right (using the IMGT database). Dots denote identity with the consensus sequence, whereas hyphens denote gaps. Six different VH and 10 different VL genes were found. Some antibodies share the same VH gene. Five out of the six different VH belong to one gene family, IGHV1-69*01. The VL genes are more diverse then the VH genes, three out of the 10 VL are κ chain. Highlighted residues for F10 are critical for binding to H5, and their conservation is indicated. VH sequences, from top to bottom: SEQ ID NO:1 (consensus) and SEQ ID NOs:3-9. VL sequences, from top to bottom: SEQ ID NO:2 (consensus) and SEQ ID NOs:10-19.

TABLE 2

Amino acid sequences of variable regions of anti-H5 mAbs

| VH | FR1 | CDR1 | FR2 | CDR2 |
|---|---|---|---|---|
| Consensus | QVQLQSGAEVKKPGSSVKVSCKASGGTFS | SYAIS | WVRQAPGQGLEWMG | GIIPMFGTPNYAQKFQG |
| IGHV1-69*01 | ............................. | ..... | .............. | ....I............ |
| D7/H98 | ....................P..IFN | TN.F. | .............V. | .V..I.R.AS...NV.. |
| D8/D80 | ............................. | AY.FT | .............. | ...GM...A........ |
| F10/E90 | ..................TS.EV... | .F... | .............L. | ..S.M............ |
| G17 | ..............A.......T..V... | ..... | .............. | ...GV..V.K....... |
| H40 | ..........R...A..........Y..T | G.Y.H | .............. | W.N.MT.GT.......V |
| A66/E8 | ........................P.. | MT.FT | .L............ | ..S.I.R..K....... |

| | FR3 | CDR3 | FR4 | IGHV gene |
|---|---|---|---|---|
| Consensus | RVTITADESTSTAYMELSSLRSEDTAVYYCAR | ---SSGYY-YG GG--FDV | WGQGTLVTVSS | |
| IGHV1-69*01 | ................................ | -------------------- | ----------- | |
| D7/H98 | ..........N......T....A......... | ---...H-F-RSH--..S | ..L........ | 1-69 |
| D8/D80 | ........L............T.....L..... | ----GL..-.-ESS--L.Y | ........... | 1-69 |
| F10/E90 | .......Q..R....D.R.............. | ---.PS.R-CSG.TCV..H | ........... | 1-69 |
| G17 | .......KP...V....N...A.......... | ---EP..-V.KN.--..V | .....M..... | 1-69 |
| H40 | W..M.R.T.IN.....VTR.T.D......... | GASVLR.FSWQPEA--L.I | ..L...T..... | 1-2 |
| A66/E8 | ..........N..N...T..K........... | --TL.S.Q-PNNDA--.AI | .....M..... | 1-69 |

| VH | FR1 | CDR1 | FR2 | CDR2 |
|---|---|---|---|---|
| Consensus | QPVLTQPPSASGSPGQRVTISC | TGSSSNIG--NYVA | WYQQKPGQAFKLLIY | SNSD----RPS |
| D7VL | NFM....H.V.A...KT..... | .......A-A...Q | ....R..S..TTV.. | EDDR----... |
| D8VL | .S.............S..... | ..T..DV.GY.S.S | ....H..K....M.. | EVTK----... |
| F10VL | ..G......V.KGLR.TA.LT. | ..N.N.V.-NQGA. | .L..HQ.HP....S. | R.N.------... |
| G17VL | SYE......V.KGLR.TAILT. | ..D.N.V.-HQGT. | .L..HQ.HP....S. | R.GN----... |

TABLE 2-continued

Amino acid sequences of variable regions of anti-H5 mAbs

| | | | | |
|---|---|---|---|---|
| H40VL | .........V.VA...TAS.P. | G.--NN..-GYS.H | ..........L.... | DDK.------... |
| A66VK | EI....S.ATLL...E.A.L.. | RA.Q.VSS----.L. | ..........R.... | DA.N-----.AT |
| D80VK | EI....S.GTLL...E.A.L.. | RA.Q.LSSK--.L. | ..........R.... | GA.S-----.AT |
| E88VL | L...........T...R.TI.. | S.......-S.T.N | ....L..T....... | S.NQ-----... |
| E90VK | DIQM..S..SLSASVGD....T. | RA.Q.ISS----.LN | .......K....... | AA.S----LQR |
| H98VL | SYE...P.....KH..R..... | S.GT....-R.H.N | ....L..T....... | ..EQ-----... |

| | FR3 | CDR3 | FR4 | IGLV gene |
|---|---|---|---|---|
| Consensus | GIPDRFSGS--RSGTTASLTISGLQPEDEADYYC | QSYDS-LSAYV | FGGGTKLTVL | |
| D7VL | .V.......ID..SNS.........T........ | ....T-NNHA. | .....H.... | LV6-57 |
| D8VL | .V.....A.--K..N.....V....A......F. | C...AG-H.... | ..T...V... | LV2-11 |
| F10VL | .ISE...A.--...N......T............ | STW...S...V. | .......... | LV10-54 |
| G17VL | .ISE..A...--...N......I............ | SVW...S...W. | .......... | LV10-54 |
| H40VL | .I.E......--N...S...T....RVEAG...G.... | .VW...GNDRPL | .......... | LV3-21 |
| A66VK | .I.A......--G...DFT....R.E...F.V.F. | .Q.G.---.PQ- | ..Q..R.EIK | KV3-20 |
| D80VK | .I.D......--G...DFT....R.E...F.V.S. | .Q...G--VPRT | ..Q..TVEIK | KV3-20 |
| E88VL | .V.D.....--....S...A.I..R......... | .....R...SL | ..T..TV... | LV1-44 |
| E90VK | .V.S......--G...DFT....S.....F.V... | QQ...---.PYT | ..Q...VEIK | KV1-39 |
| H98VL | .V.D......--K...S...AV....S........ | A.W.DN..GW. | .......... | LV1-44 |

Figure 10:
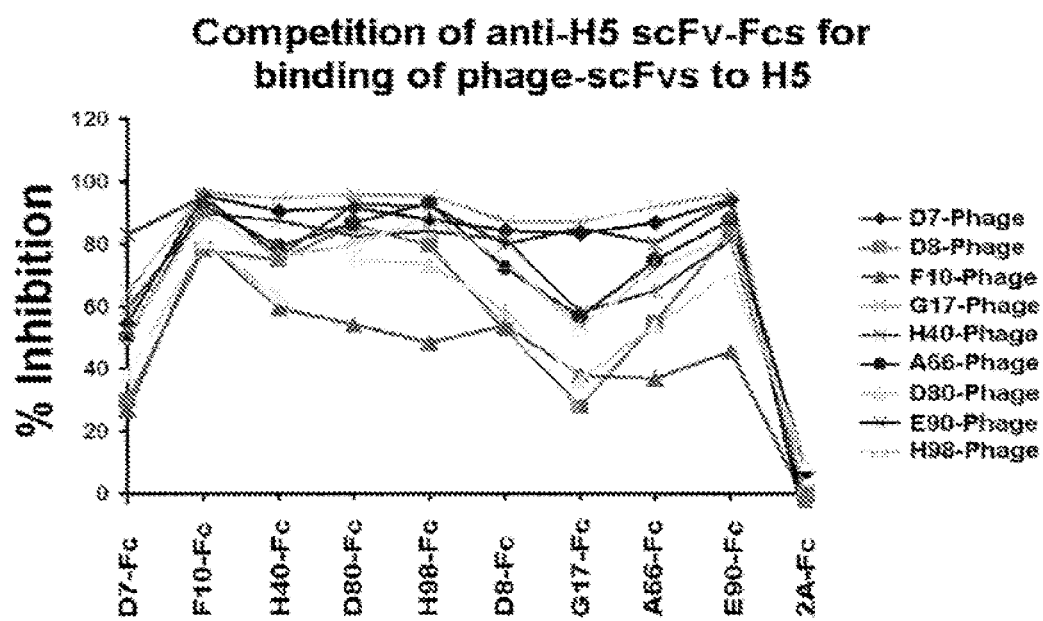
FIG. 10 shows binding of anti-H5 scFv-Fcs so H5 or HA1 by competition ELISA. $10^{12}$ pfu of anti-H5 phage-scFvs were mixed with 5 μg/mL of anti-H5 scFv-Fcs and added to H5 (H5-VN04)-coated plates, washed, and followed by HRP-anti-M13 to detect phage-scFvs bound to H5. mAb 2A-Fc did not compete for the epitope recognized by the 10 H5-selected Abs. All H5-selected scFv-Fcs cross-competed. Of these, Ab F10 (phage-scFv) binding to the H5 trimer was the least inhibited by the other scFv-Fcs suggesting that it has the highest affinity among all Abs tested.
Figure 11:
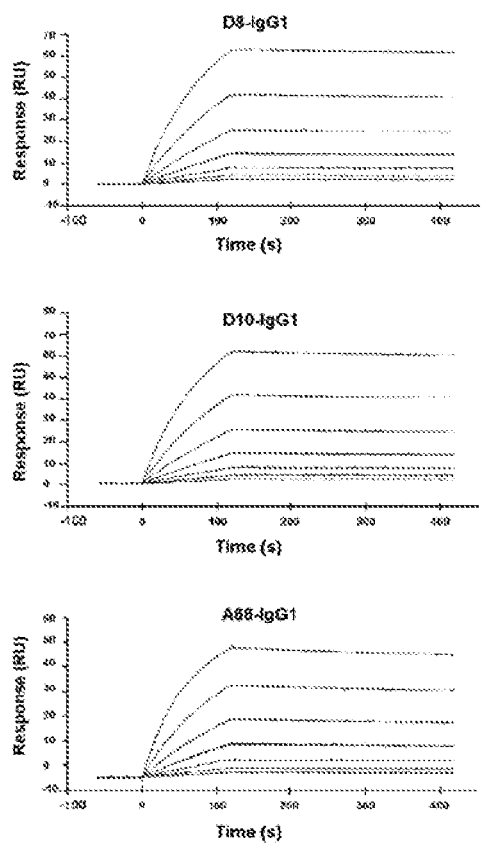
FIG. 11 shows kinetic and thermodynamic characterization of the binding of H5 to nAbs D8, F10 and A66-IgG1s. nAbs were captured on a CM4 chip via anti-human IgG1; trimeric H5 (H5-VN04) at various concentrations (20, 10, 5, 2.5, 2.5, 1.25, 0.625 nM) was injected over the chip surface. Binding kinetics were evaluated using a 1:1 Langmuir binding model. The recorded binding curves (with blank reference subtracted) and the calculated curves are closely superimposable. Each ka, kd and $K_D$ value represents the mean and standard error of three experiments. Note: the middle graph labeled "D10-IgG" is actually a graph of F10-IgG.

All 10 nAbs were found to bind trimeric H5-VN04 with similar avidity, but did not bind monomeric HA1 (FIG. 1A). Presented as scFv-Fc constructs, they potently neutralized the Clade 1 H5 pseudo-virus, A/Thailand/2-SP-33/2004 (H5N1) ("H5-TH04") (FIG. 1B); and, in a stringent plaque-reduction assay, they all exhibited high levels of neutralization against H5-VN04, as well as the more divergent (Clade 2.1) A/Indonesia/5/2005 ("H5-IN05") (FIGS. 1C and 1D). It was also found that the nAbs cross-competed with each other in a competition ELISA (FIG. 10), indicating that they share a common epitope. Based on this finding, as well as VH sequence diversity and neutralization potency, three of the nAbs (D8, F10 and A66) were converted into full-length human IgG1s for further studies; all three IgG1s bound to recombinant H5-VN04 with high affinity (Kd~100-200 pM) and very slow dissociation rates (kd~$10^{-4} s^{-1}$) (FIG. 11).

ii. Prophylactic and Therapeutic Efficacy in Mice

The protective efficacy of the three IgG1s against H5N1 virus infection was evaluated in a BALB/c mouse model (FIG. 2). Mice were treated with IgG1s before (prophylactically) or after (therapeutically) lethal viral challenge. Prophylaxis using 10 mg kg$^{-1}$ of IgG1s effectively protected (80-100%) mice when challenged with a high lethal dose of H5-VN04 (Clade 1) or A/HongKong/483/97 (H5-HK97) (Clade 0) (FIGS. 2A and 2B). Therapeutic treatment with 15 mg kg$^{-1}$ (an achievable dose in humans) of IgG1 at 24 h post-inoculation also protected 80-100% of the mice challenged with either H5-VN04 or H5-HK97 virus (FIGS. 2C and 2D). Mice treated at later times (48 or 72 h post-inoculation) with H5-VN04 showed similar or higher levels of protection (FIGS. 2E and 2F). Furthermore, surviving mice remained healthy and showed minimal body weight loss over the 2-week observation period.

Figure 12:
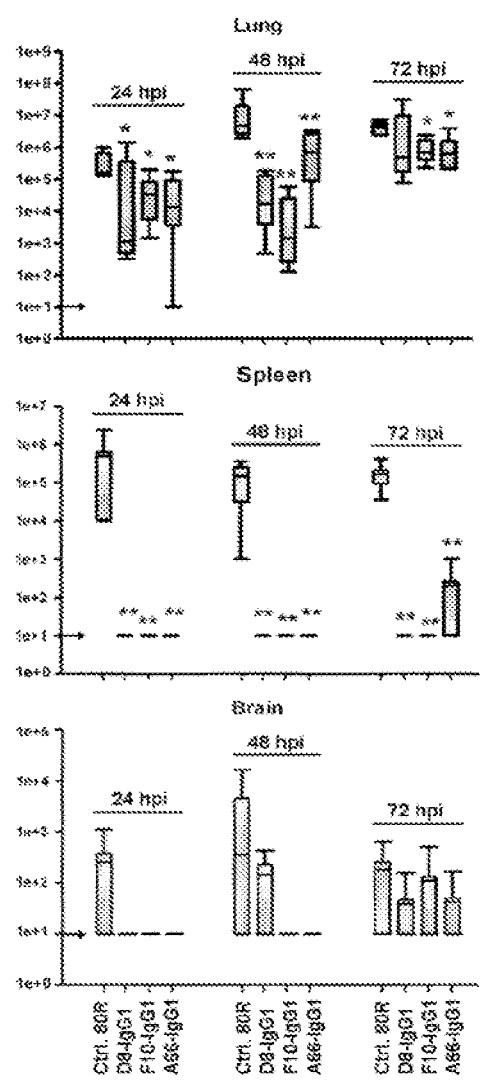
FIG. 12 shows viral titers in lung, spleen and brain of mice treated with anti-H5 nAbs after H5-VN04 challenge. BALB/c mice (n=5) were treated by i.p. injection of 15 mg/kg of mAb at 24, 48 or 72 hrs after i.n. infection with 10 MLD50 of H5-VN04. Viral titers were determined in lung, brain, and spleen collected at 96 hpi. Data are displayed in box-and-whiskers form in which the box extends from the 25th to the 75th percentile, with a horizontal line at the median. Whiskers above and below the box indicate the extreme values. Results of Student T-test statistic analysis are noted with a single star (*) for $p<0.05$, and double stars (**) for $p<0.01$. The arrows crossing the Y axis indicate the detection limit of the titration.
Figure 16:
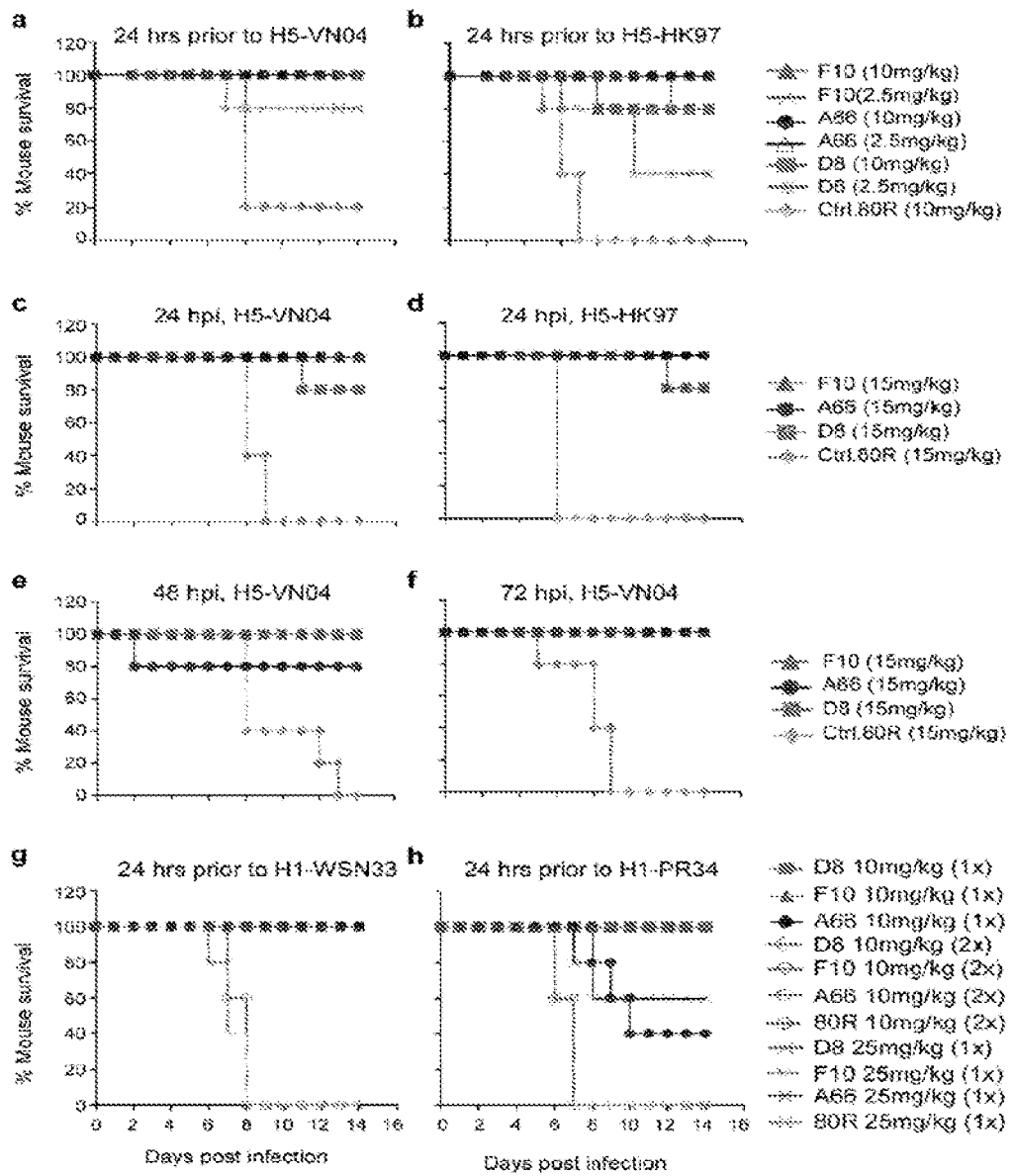
FIG. 16 shows the prophylactic and therapeutic efficacy of anti-H5 nAbs in mice. Mice were treated with different doses of nAb either before or after lethal viral challenge. Prophylactic efficacy (a, b, g and h). Mice were treated with anti-H5 nAbs or control mAb 24 hour before lethal challenge by intranasally (i.n.) with 10 median lethal doses (MLD50) of the H5N1 or H1N1s. (a) Intra-peritoneal (i.p.) injection of 10 mg/kg of any of the three nAbs provided complete protection of mice challenged with H5-VN04 (A/Vietnam/1203/04 (H5N1), Clade 1). A lower antibody dose (2.3 mg/kg) was also highly protective. (b) Prophylactic protection against H5-HK97 (A/HongKong/483/97 (H5N1), Clade 0) virus was observed in 80-100% of the mice treated with 10 mg/kg of any of the three nAbs. (g) Any of the three nAbs (at 10 mg/kg of single injection) provided complete protection of mice challenged with H1-WSN33 (A/WSN/1933(H1N1)) viruses. (h) D8 and F10 completely protected mice challenged with H1-PR34 (A/Puerto Rico/8/34 (H1N1)) when given at 10 mg/kg of single injection. A66 provided complete protection of mice when 25 mg/kg of antibody was given as a single injection. Therapeutic efficacy (c-f). Mice were inoculated with H5-VN04 and injected with nAbs at 24, 48, 72 hpi (c, e and f) or with H5-HK97 at 24 hpi (d). I.p. treatment with 15 mg/kg (a therapeutically achievable dose in humans) of any of the 3 nAbs at 24 h post-inoculation (hpi) protected 80-100% of mice challenged with 10-times the MLD50 of either H5-VN04 or H5-HK97 virus.
Figure 17:
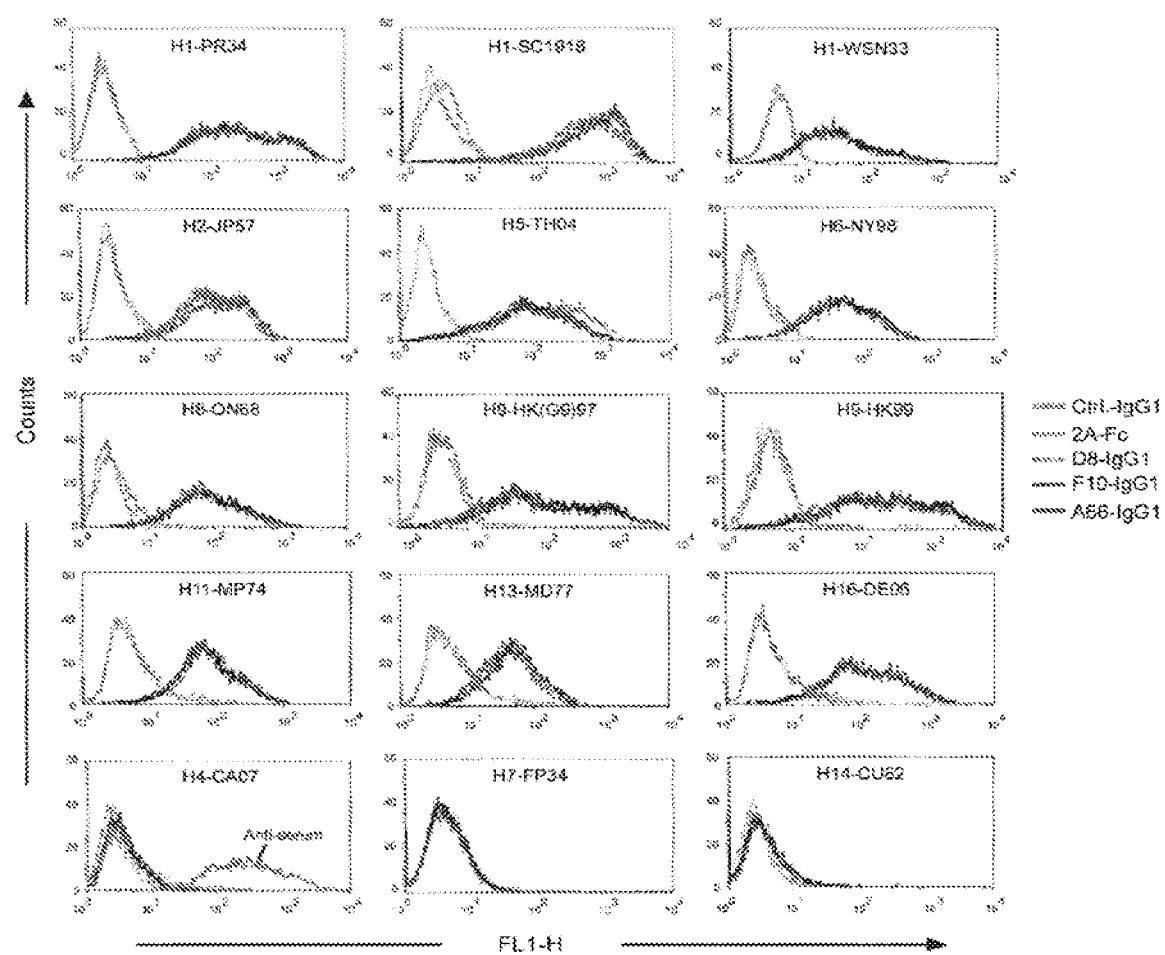
FIG. 17 shows FACS analysis of anti-H5 nAbs binding to H1, H2, H5, H6 (cluster H1a); H11, H13 and H16 (Cluster H1b); and H8 and H9 (Cluster H9). 293T cells were transiently transfected with different HA-expressing plasmids, and mAb binding to the cells was analyzed by FACS. H5-specific antibody 2A and 80R are negative control. Lack of binding to Group 2 HAs, H4, H7, and H14, are also shown. Complete viral strain designations are:
H1-PR34 (A/Puerto Rico/8/34 (H1N1));
H1-SC1918 ((A/South Carolina/1/1918 (H1N1));
H1-WSN33 (A/WSN/1933 (H1N1));
H5-TH04 (A/Thailand/2-SP-33/2004 (H5N1));
H2-JP57 (A/Japan/305/57(H2N2));
H4-CA07 (A/bufflehead/California/HKWF205/2007 (H4N8))
H6-NY98 (A/Chicken/New York/14677-13/1998 (H6N2));
H7-FP34 (A/FPV/Rostock/34 (H7N1));
H8-ON68 (A/turkey/Ontario/6118/68);
H9-HK(G9)97 (A/chicken/HongKong/G9/97 (H9N2));
H9-HK99 (A/HongKong/1073/99 (H9N2));
H11-MP74 (A/duck/memphis/546/74 (H11N9));
H13-MD77 (A/Gull/MD/704/77 (H13N6));
H14-CU82 (A/mallard/Gurjev/263/82(H14N5));
H16-DE06 (A/Shorebird/DE/172/06 (H16N3)).
Figure 18:
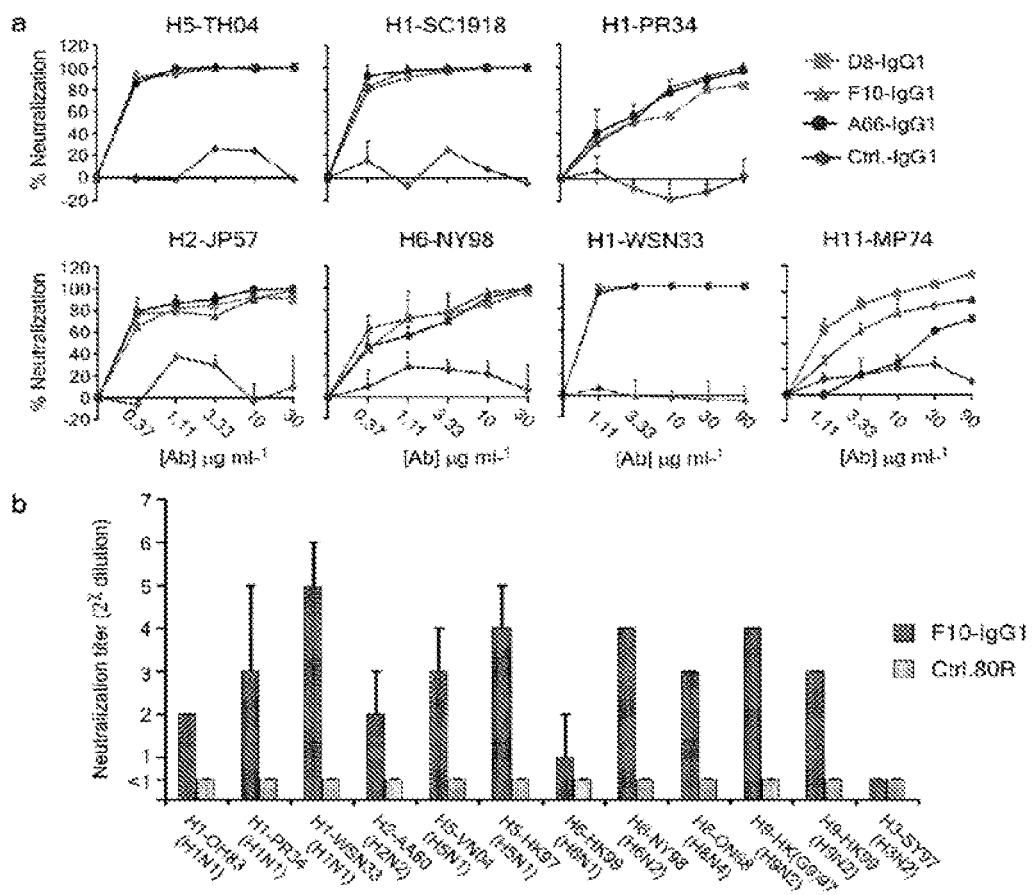
FIG. 18 shows cross subtype neutralization by nAbs. (a) nAbs D8, F10 and A66 all neutralized H5-TH04, H1-SC1918, H1-PR34, H1-WSN33, H2-JPS7, H6-NY98 and H11-MP74 pseudotyped viruses. (b) Microneutralization assay. Neutralization titers (0.1 mg ml$^{-1}$ Ab stock solution) of nAb F10 against two wild-type H5N1, three H1N1, one H2N2, one H6N1, one H6N2, one H8N4, two H9N2 and one H3N2 virus. 80R is the negative control. Vertical bars and whiskers represent the lowest and highest neutralization titer.
Figure 19:
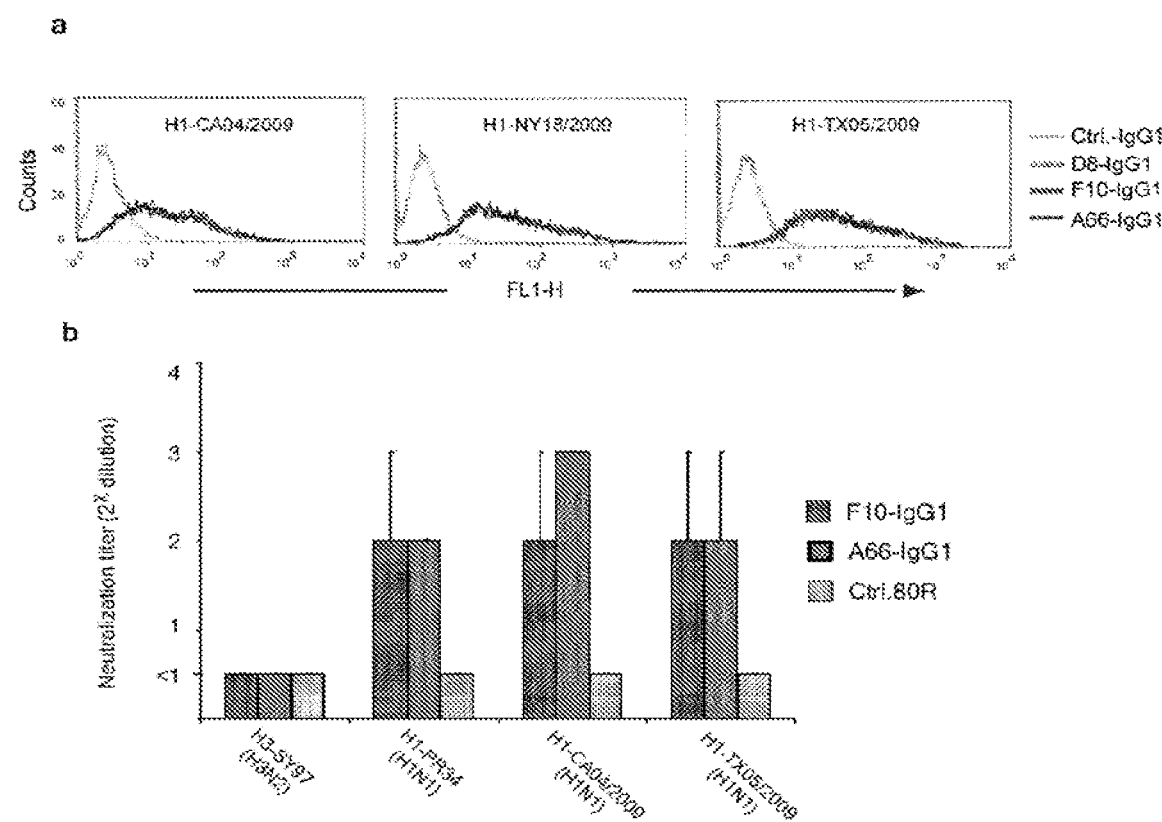
FIG. 19 shows binding to HA of Swine flu H1N1 viruses and neutralization of Swine flu H1N1 viruses by nAbs. (a) FACS analysis of nAbs D8, F10 and A66 binding to H1 proteins of three swine flu H1N1 2009 pandemic strains. 293T cells were transiently transfected with different HA-expressing plasmids, and mAb binding to the cells was analyzed by FACS. Anti-SARS antibody 80R was used as negative control. (b) Microneutralization assay. Neutralization titers (0.1 mg ml$^{-1}$ Ab stock solution) of nAb F10 against H1N1-PR34, two swine flu 2009 H1N1 strains, and a control H3N2 virus. 80R is the negative control. Vertical bars and whiskers represent the lowest and highest neutralization titer (2 values of are shown on the y-axis) of 2-3 independent experiments.

While human influenza viruses are typically restricted to the upper respiratory tract, systemic spread is a typical outcome of H5N1 infection in mice, and has been reported in some humans. It was found that the three IgG1s caused potent suppression of viral replication in the lungs (measured 4 days post-challenge) of mice treated within 48 hours of viral challenge; and that two IgG1s, F10 and A66, were effective when given at 72 hpi. The impact of antibody therapy on systemic infection was dramatically demonstrated by ≥1000-fold suppression of virus spread to the spleen, even when given 72 hpi (FIG. 12). Suppression was also seen in the brain, but in this case systemic spread was too low in control animals for accurate quantitation.

iii. nAbs Inhibit Cell Rather than Receptor Binding

Figure 3:
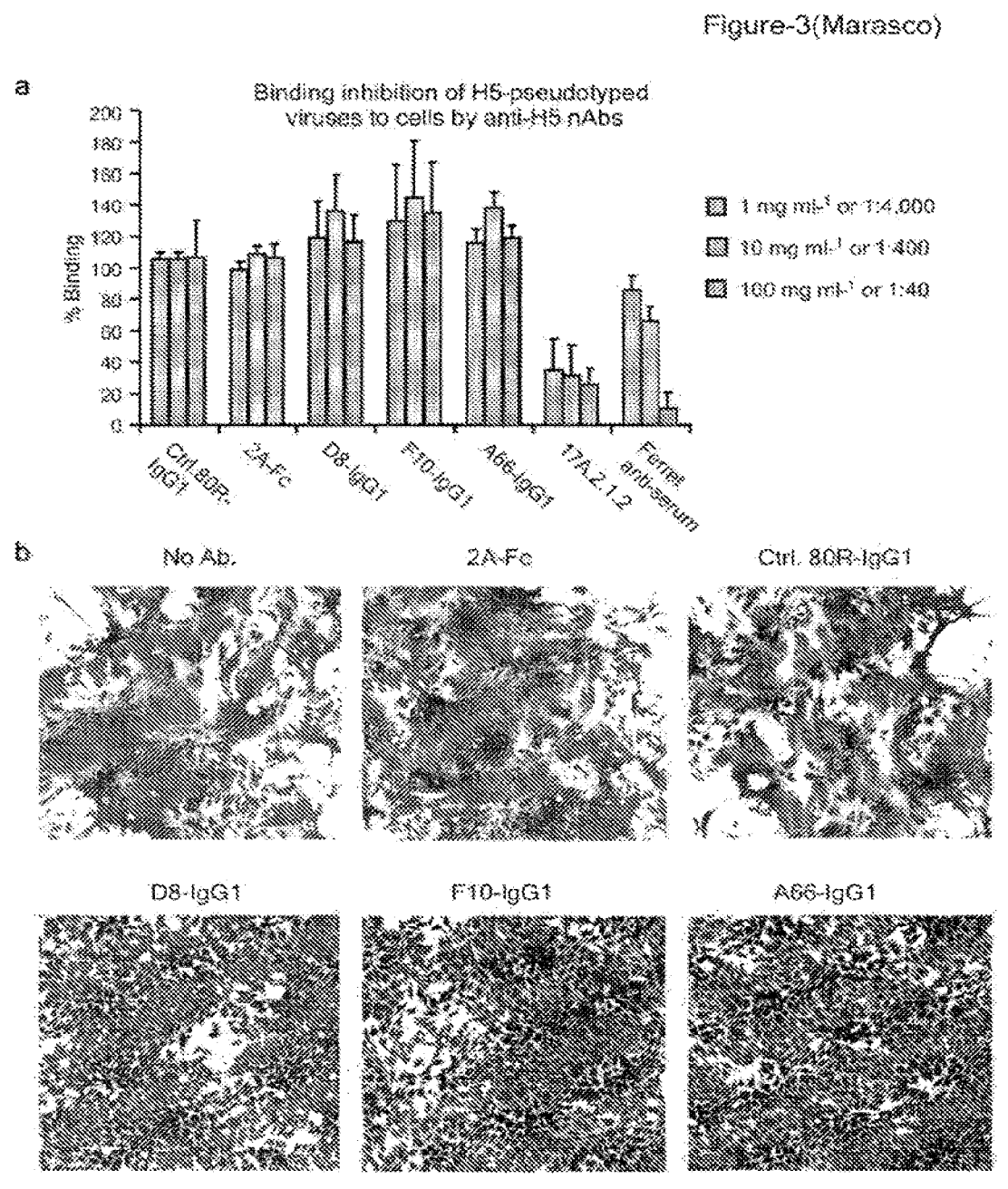

Two ways in which anti-HA Abs can neutralize infection is by blocking the initial binding of HA to its cellular receptor (sialic acid) or by interfering with the subsequent step of HA-mediated virus-host membrane fusion, which occurs in acidic endosomes (Skehel & Wiley, Receptor binding and membrane fusion in virus entry: the influenza hemagglutinin. *Annu Rev Biochem* 69, 531-69 (2000); Kida et al., Interference with a conformational change in the haemagglutinin molecule of influenza virus by antibodies as a possible neutralization mechanism. *Vaccine* 3, 219-22 (1985)). It was found that none of the nAbs inhibited virus binding to cells (FIG. 3A) or hemagglutination of red blood cells. However, it was shown, using a model system of cell fusion, that the nAbs potently inhibited membrane fusion (FIG. 3B).

iv. Structural Characterization of the nAb Epitope

In order to provide a structural basis for neutralization and to establish that even broader-spectrum therapeutics can be based on this discovery, the crystal structure of F10 (as the scFv fragment) in complex with the H5 (H5-VN04) ectodomain (FIG. 4) was determined. H5 activated by cleavage of the single chain precursor, HA0, into two polypeptides, HA1 and HA2 was used. Cleavage leads to the partial burial of the "fusion peptide" (the first ~21 residues of each HA2) into the stem (Skehel & Wiley (2000); Ha et al., H5 avian and H9 swine influenza virus haemagglutinin structures possible origin of influenza subtypes. *Embo J* 21, 865-75 (2002)), which also contributes to the formation of each of three hydrophobic "pockets" located below the large trimeric receptor-binding head. In the complex, one F10 nAb binds into each pocket, burying ~1500 Å$^2$ of protein surface. Only the heavy chain (VH) participates directly in binding, utilizing all three of its complementarity-determining regions (CDRs). The light chain (VL) points out into solution, and makes only non-specific contacts with the distal end of the oligosaccharide of glycosylated residue Asn33$_1$ from a neighboring monomer. The epitope on H5 encompasses the entire pocket, which is formed by the HA2 fusion peptide, flanked by elements of HA1 on one side and helix αA of HA2 on the other.

The key interactions are as follows (FIG. 4B): (i) CDR-H2 adopts the "type 2" conformation (Chothia et al., Structural repertoire of the human VH segments. *J Mol Biol* 227, 799-817 (1992)), which is relatively rare in human Abs. Two hydrophobic residues, Met54 and Phe55, from the tip of H2, insert into the pocket. Phe55 lies across a flat hydrophobic surface formed by the main-chain of the fusion peptide, residues 18$_2$-21$_2$; it also makes favorable orthogonal aromatic interactions (Samanta et al., Packing of aromatic rings against tryptophan residues in proteins. *Acta Crystallogr D Biol Crystallogr* 55, 1421-7 (1999)) with the side-chains of Trp21$_2$ at the back of the pocket, and His18$_1$ at the front (subscripts 1 or 2 refer to HA1 or HA2, and the numbering scheme follows the structure of H3 (pdb:2hmg) (Stevens et al., (2006); Weis et al., Refinement of the influenza virus hemagglutinin by simulated annealing. *J Mol Biol* 212, 737-61 (1990))). The Met54 sulfur makes Π-aromatic interactions (Pal & Chakrabarti, Non-hydrogen bond interactions involving the methionine sulfur atom. *J Biomol Struct Dyn* 19, 115-28 (2001)) with the Trp21$_2$ ring, hydrophobic interactions with Ile45$_2$ from helix αA, an a H-bond between Met54 C=O and the His38$_1$ side-chains; (ii) Tyr102 from CDR-H3 extends from the apex of the H3 loop, to a location only ~3 Å from Phe55, and complements CDR-H2 by cementing together the fusion peptide (via a main-chain H-bond to Asp19$_2$) and the αA helix of HA2 (by intercalating between Thr41$_2$ and Ile45$_2$). A large hydrophobic residue at the neighboring position 103 supports the side-chain conformation of Tyr102; and (iii) the CDR-H1 loop is characterized by small hydrophobic/polar side-chains (notably Val27, Thr 28 and Ser31) such that CDR-H1 fits snugly beneath the HA head while packing against helix αA. A somatic mutation of conserved Gly26=>Glu generates a non-canonical conformation for H1, with Thr27 pointing outward and making contact with H5.

An N-terminal hairpin (residues 129$_2$ and M30$_2$) from HA2 of the counterclockwise neighbor packs against the other side of helix αA at this point, wrapping around its fusion peptide and further locking it into place (FIGS. 4A and 4C). Thus, F10 stabilizes the fusion peptide of more than one subunit. One framework (FR3) residue, Gln74, appears to be especially important in stabilizing the CDR-H1 and CDR-H2 loop conformations, by forming H-bonds to the main chain C=O groups of Pro53 and Met54, as well as the side-chain of Ser30. The FR3 residue at position 72 is the major determinant of the choice between two distinct conformations of the H2 loop (Chothia et al. (1992)).

Consistent with the structural data, mutations in three H5 residues on HA2 αA that make important interactions with F10—Val52$_2$, Asn53$_2$ and Ile56$_2$—greatly reduce or ablate nAb binding, while the conservative mutation, Val52Leu, has no effect (FIGS. 4C and 4D). Mutations to other surfaces of the αA helix either have no effect (typically exposed residues) or lead to increased nAb binding, perhaps by subtly increasing the flexibility of the epitope (FIG. 4D). Significantly, the nine other nAbs show very similar mutant binding profiles. Together with the cross-competition noted above, this indicates that the epitopes for all 10 nAbs overlap very closely, and that the nAbs bind in a similar location and orientation.

v. Structural Basis of H5 Neutralization by the nAb Panel

The broad neutralizing behavior against H5 can be attributed in part to the exclusive role of VH in antigen binding and the use of a common germline gene, VH1-69, in five out of the six VHs—although their CDR3 loops are variable in sequence and length (13-17 residues) (Table 2). In addition, free energy calculations (Champ & Camacho, FastContact: a free energy scoring tool for protein-protein complex structures. *Nucleic Acids Res* 35, W556-60 (2007)) point to dominant binding contributions (~70% of the total favorable free energy) of the three conserved residues in the VH segment (highlighted residues in Table 2). In CDR-H2 derived from germline V1-69, position 55 is always Phe, and position 54 is always hydrophobic (M/I/L/V). In the nAbs used in this example, CDR-H3 always has a Tyr predicted to lie at the tip of the CDR3 loop (conserved at the 6th position). The conformation and sequence of the CDR1 loop does not seem to be critical, since the other Abs that were isolated do not contain the somatic mutation (Gly26=>Glu) found in F10, and are predicted to have canonical structures. The sixth VH gene that was isolated is derived from the germline gene, VH1-2; its H2 loop has the same length as VH1-69, but by virtue of a change from Ala to Arg at position 72 (Chothia et al. (1992)) it is predicted to adopt a distinct conformation ("type 3"), which presents loop residues 3 and 4 to the antigen (rather than residues 4 and 5 in type 2 loops). The specific somatic mutation at position 4, from Asn to Met, presumably promotes H5 binding. It is not possible to predict the structure of the larger H3 loop, but a tyrosine is located at the center of the loop that may play an analogous role to that in VH1-69.

Thus, the F10-H5 crystal structure indicates a common mechanism of H5 virus neutralization for the discovered nAbs. They make no contact with the receptor-binding sites in the head and so do not inhibit cell attachment. Rather, they lock the fusion peptide and helix αA in place, thereby preventing the large structural reorganizations that are required for membrane fusion (Stevens et al., Structure and receptor specificity of the hemagglutinin from an H5N1 influenza virus. *Science* 312, 404-10 (2006); Skehel & Wiley (2000); Stevens et al., Structure of the uncleaved human H1 hemagglutinin from the extinct 1918 influenza virus. *Science* 303, 1866-70 (2004); Daniels et al., Fusion mutants of the influenza virus hemagglutinin glycoprotein. *Cell* 40, 431-9 (1985); Thoennes et al., Analysis of residues near the fusion peptide in the influenza hemagglutinin structure for roles in triggering membrane fusion. *Virology* 370, 403-14 (2008); Earp et al., The many mechanisms of viral membrane fusion proteins. *Curr Top Microbiol Immunol* 285, 25-66 (2005)). The data point to this event occurring at an early step in the infectious process, although it cannot be ruled out that the nAbs act at a later stage, given the close packing of molecules on the surface of the mature virion which might restrict early access to the epitope. The only previously published crystal structure of an HA-nAb complex that inhibits membrane fusion utilizes a different mechanism: it prevents conformational changes by cross-linking the upper surfaces of adjacent subunits in the head (Barbey-Martin et al., An antibody that prevents the hemagglutinin low pH fusogenic transition. *Virology* 294, 70-4 (2002)).

vi. Anti-H5 nAbs Bind and Neutralize a Broad Range of Group 1 Viruses In Vitro and In Vivo Next, all of the available HA sequences (total 6360) in the public influenza sequence database (Table 3) were examined. Of note, the sequences of the F10 epitope are nearly always conserved within the H5 subtype. Indeed, many epitope residues, especially is HA2, are highly conserved across all 16 HA subtypes (FIG. 5). This high sequence conservation provides a rationale for the cross-neutralization of the H5N1 virus clades described above. This was then confirmed by test the antibodies against a broader range of HA subtypes.

Table 3. Highlights: top '( )/', (amino acid variant(s))/ amino acid consensus at the position; bottom '( )/', (number of amino acid variants)/number of consensus amino acids. Non-highlighted amino acids are 100% conserved or variants are observed ≤5 times at those positions for subtypes H4, H6, H9, H10, H11. Histidines H17 (HA1) and H111 (HA2) that can play a role in pH-trigger are in bold underline.

| Group | Cluster | Subtype | # Sequence | # Unique Sequence | HA1 17 | 18 | 38 | 40 | 291 | HA2 18 | 19 | 20 |
|---|---|---|---|---|---|---|---|---|---|---|---|---|
| Group 1 | H1a | H2 | 100 | 95 | Y | H | H | (Q, E)/K (18)/77 | T | (I)/V (20)/75 | D | G |
| | | H5 | 1620 | 1178 | (S, T, F)/Y (4)/1174 | (Y, M)/H (2)/1176 | (Q, Y)/H (4)/1174 | (K)/Q (2)/1176 | (I, N, T, R)/S (6)/1172 | (I)/V (6)/1172 | (N, H, Y, X)/D (5)/1173 | G |
| | | H1 | 1211 | 701 | Y | H | H | (I)/V (2)/699 | (S)/N (16)(685) | (V, M)/I (137)/546 | D | G |
| | | H6 | 278 | 230 | Y | H | H | V | (1)/N (1)/229 | (V)/I (43)/187 | D | G |
| | H1b | H13 | 16 | 16 | Y | L | S | (V)/1 | N | I | N | G |
| | | H16 | 8 | 6 | Y | L | S | (I)/V (2)/6 | N | I | N | G |
| | | H11 | 64 | 64 | Y | L | S | (I)/V (1)/64 | (T)/S (1)/63 | (L)/I (1)/63 | N | G |
| | H9 | H8 | 10 | 10 | Y | Q | Q | M | S | I | D | G |
| | | H12 | 19 | 18 | Y | Q | Q | E | S | V | A | G |
| | | H9 | 252 | 234 | (H)/Y (33)/201 | (L)/Q (1)/233 | (D)/H (1)/233 | (R, E)/K (5)/229 | (I)/T (1)/233 | V | (S)/A (1)/233 | G |
| Group 2 | H3 | H4 | 105 | 90 | H | H | (A)/T (1)/89 | (R)/Q (1)/89 | (A, I, S, N)/T (10)/82 | I | D | G |
| | | H14 | 2 | 2 | H | H | S | K | D | I | D | G |
| | | H3 | 2302 | 1228 | H | H | N | (N)/T (1)/1227 | (N, Y, E, G)/(D) (35)/1193 | (M)/(V/I) (149)/ (70%/30) | (N)/D (15)/1213 | G |
| | H7 | H15 | 8 | 5 | H | H | N | T | P | I | D | G |
| | | H7 | 334 | 273 | H | H | N | T | (S, R, P)/N (131)/142 | (V)/I (41)232 | (N)/D (57)213 | G |
| | | H10 | 31 | 28 | H | H | N | T | (E)/K (1)/27 | V | (N, E)/D (2)/26 | (A)/G (1)/27 |

| Group | Cluster | Subtype | HA2 21 | 38 | 41 | 42 | 45 | 49 | 52 | 53 | 56 | 111 |
|---|---|---|---|---|---|---|---|---|---|---|---|---|
| Group 1 | H1a | H2 | W | K | T | Q | (F)/VI (39)/56 | T | (I)/V (1)/94 | N | I | H |
| | | H5 | (R)/W (1)/1177 | (Q, R, N)/K (23)/1155 | (S)/T (3)/1175 | (P)/Q (1)/1177 | (M, L, T)/I (8)/1170 | (I)/T (1)/1177 | V | N | (F)/V (1)/1177 | H |
| | | H1 | W | (K, R, L)/Q (60)/641 | T | Q | (V)/I (2)/699 | (S, N, X)/T (19)/682 | (M, I)/V (2)/699 | N | (V)/I (1)/700 | H |
| | | H6 | (R)/W (1)/229 | (R)/K (102)/128 | T | Q | (V)/I (78)/152 | (I,)/T (1)/229 | (I,)/V (3)/227 | N | I | H |
| | H1b | H13 | W | K | T | Q | I | T | V | N | I | H |
| | | H16 | W | K | T | Q | I | T | V | N | I | H |
| | | H11 | W | (R)/K (5)/59 | T | Q | (V)/I (3)/61 | (I)/I (1)/63 | V | N | (I, A)/V (17)/47 | H |
| | H9 | H8 | W | Q | T | Q | I | T | (I)/V (1)/9 | N | I | H |
| | | H12 | W | R | T | Q | I | Q | L | N | I | H |
| | | H9 | (G)/W (1)/233 | (K, G)/R (14)/220 | T | Q | (V, F, M, R)/I (43)/191 | (I)/T (1)/233 | V | (S, T, D)/N (3)/231 | (I)/V (55)/179 | (C)/H (1)/233 |

-continued

| | | | | | | | | | | | |
|---|---|---|---|---|---|---|---|---|---|---|---|
| Group 2 | H3 | H4 | (G)/W (1)/91 | L | T | Q | I | (N)/T (1)/89 | L | N | I | (A)/T (2)/90 |
| | | H14 | W | L | T | Q | I | N | L | N | I | T |
| | | H3 | W | (F)/L (1)/1227 | T | Q | (V, T, L)/I (5)/1223 | (D, S, T, A)/N (22)/1206 | (M)/L (1)/1227 | (D)/N (1)/1227 | (V, T, F)/I (19)/1209 | (A)/T (7)/1221 |
| | H7 | H15 | W | Y | T | Q | I | T | L | N | I | A |
| | | H7 | W | (H)/Y (1)/272 | T | (P)/Q (2)/271 | (V)/L (3)/270 | T | L | N | I | (T)/A (35)/238 |
| | | H10 | W | Y | T | Q | I | T | L | N | (V)/I (1)/27 | A |

Group 1 viruses, which contain 10 of the 16 subtypes, are further classified into 3 "clusters", H1a, H1b, and H9 (Russell, et al., H1 and H7 influenza haemagglutinin structures extend a structural classification of haemagglutinin subtypes. *Virology* 325, 287-96 (2004); Fouchier et al., Characterization of a novel influenza A virus hemagglutinin subtype (H16) obtained from black-headed gulls. *J Virol* 79, 2814-22 (2005)) (FIG. 5). nAb binding to eight members of Clusters H1a, H1b and H9, which include avian H5 as well as the most common human influenza subtypes (the major exception is the Group 2 subtype, H3), were tested. In addition to H5, it was found that all three IgG1s bound to cells expressing full-length H1 from two different strains of H1N1, including the 1918 "Spanish flu"; H2 from H2N2; and H6 from H6N2; the Cluster 1b subtypes: H11 from H11N9; H13 from H13N6; and H16 from H16N3; as well as Cluster H9 subtypes from two H9N2 strains. However, none of them bound to a Group 2 subtype, H7 from H7N1 (FIG. 1D).

Figure 6:
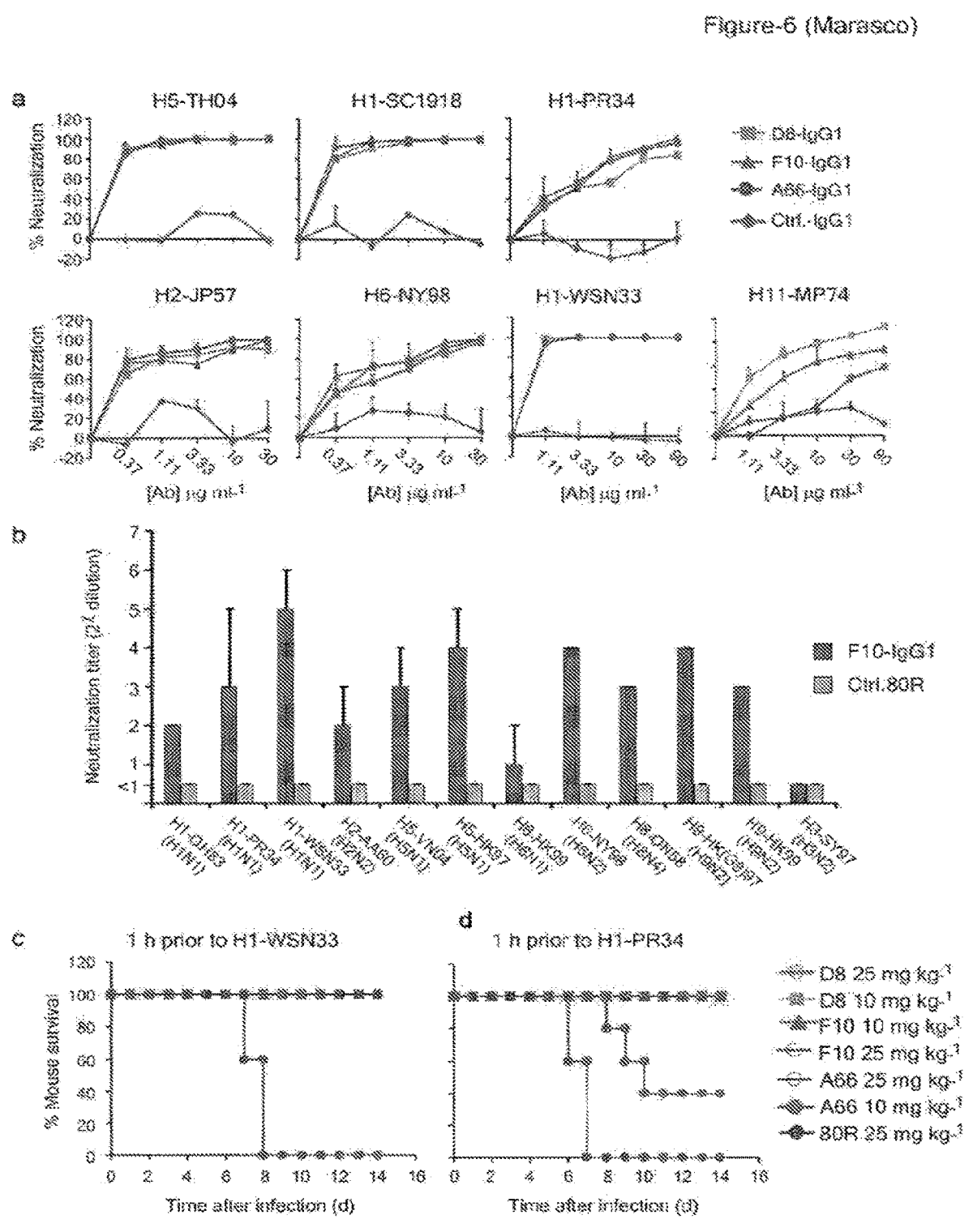

The IgG1s also neutralized H5-, H1-, H2-, H6- and H11-pseudotyped virus infections (FIG. 6A). In a microneutralization assay, F10-IgG1 also neutralized H5N1, H1N1, H2N2, H6N1, H6N2, H8N4, and H9N2 influenza viruses (FIG. 6B). However, none of the nAbs neutralized Group 2 viruses, e.g. H3N2 (FIG. 6B). Thus, these nAbs recognize an epitope on HA that is conserved among H5 clades as well as in all members of Group 1 viruses. Finally, the in vivo protective efficacy of two of the IgG1s was demonstrated against two lethal H1N1 viral strains in a BALB/c mouse model, using the same protocol as for the H5N1 studies (FIGS. 6C and 6D).

vii. Structural Basis of the Group-Specific Broad-Spectrum Virus Neutralization The ability of the nAbs to recognize all Group 1 (cluster H1a/b and H9) viruses (H12 was not tested) can be attributed to the key conserved features of the nAbs described above in combination with the highly conserved pocket on HA (FIGS. 4 and 5). The epitope can be divided into 3 elements: (i) at its center, the sequence of the N-terminal segment of HA2—fusion peptide residues $18_2$-$21_2$—is conserved across all HA subtypes (note that the side-chain at position $19_2$ does not participate in binding); (ii) a downstream segment of HA2 adopts part of the αA helix (residues $39_2$-$56_2$), which is nearly invariant; the only significant difference is a Thr to Gln change at position $49_2$ in the untested H9 cluster subtype, H12. Thr$49_2$ lies at the periphery of the epitope and makes one long H-bond (3.5 Å) to Ser31. Simple modeling suggests there is plenty of space to accommodate the larger Gln side-chain and that it can make comparable H-bonds; and (iii) smaller contributions from segments of the HA1 chain (residues $18_1$ and $38_1$) and a loop at the base of the head (residues $291_1$ and $292_1$).

3-dimensional comparisons of the epitope in the 5 known crystal structure subtypes (three Group 1 (H1, H5 and H9) and two Group 2 (H3 and H7)) (Russell et al., H1 and H7 influenza haemagglutinin structures extend a structural classification of haemagglutinin subtypes. *Virology* 325, 287-96 (2004); Ha et al., H5 avian and H9 swine influenza virus haemagglutinin structures: possible origin of influenza subtypes. *Embo J* 21, 865-75 (2002); Gamblin et al., The structure and receptor binding properties of the 1918 influenza hemagglutinin. *Science* 303, 1838-42 (2004); Yamada et al., Haemagglutinin mutations responsible for the binding of H5N1 influenza A viruses to human-type receptors. *Nature* 444, 378-82 (2006); Ha et al., X-ray structure of the hemagglutinin of a potential H3 avian progenitor of the 1968 Hong Kong pandemic influenza virus. *Virology* 309, 209-18 (2003)) show that they adopt two distinct structural classes consistent with the phylogenetic groupings (Russell et al. (2004); Fouchier et al. (2005)) (FIG. 7). These differences arise from group-specific differences in the location of buried residues, notably histidines (H$111_2$ is unique to Group 1; H$17_1$ is unique to Group 2) that have been proposed to be the "triggers" for pH-induced conformational changes (Thoennes et al. (2008)). The differences cause the side-chain of Trp$21_2$ to turn through 90° in Group 2 subtypes, eliminating favorable binding to Phe55 from the tested nAbs. In addition, four out of six Group 2 subtypes are glycosylated at position $38_1$, at the periphery of the F10 epitope; modeling studies predict steric clashes with the CDR-H1 loop. These structural differences rationalize the observed lack of binding/neutralization of Group 2 HA subtypes and viruses.

viii. Prospects for Immune Escape

The remarkable transformation to the fusogenic state includes repacking of the central helices of three HA2 protomers to form a new triple-helical bundle, in which residues 34-37 form an N-terminal cap, as well as the creation of C-terminal arms that extend to the N-terminal of the new bundle (Chen et al., N- and C-terminal residues combine in the fusion-pH influenza hemagglutinin HA(2) subunit to form an N cap that terminates the triple-stranded coiled coil. *Proc Natl Acad Sci USA* 96, 8967-72 (1999)). it is straightforward to model the locations of the F10 epitope residues in this model of the fusogenic state. All 8 epitope residues, which were fully exposed in the neutral pH structure, become either part of the new hydrophobic bundle core (Thr$41_2$, Ile$45_2$, Val$56_2$ and Ile$56_2$), or they make networks of H-bonds with the C-terminal arms and other elements that stabilize the new bundle (Lys $38_2$, Gln$42_2$, Thr$49_2$, Asn$53_2$). The requirement for adopting two entirely different conformations, each with a distinct hydrophobic core and H-bonding network may place powerful evolutionary constraints on the sequence of the helix, as evidenced by the almost complete lack of genetic drift within helix αA among the 16 HA subtypes.

To test this hypothesis, an attempt was made to select neutralization escape mutants. VN/04 (H5N1) virus was propagated in MDCK cells for 72 h in the presence of 40 μg ml$^{-1}$ of each of the 3 nAbs as well as a murine Ab, 22F, that targets the receptor-binding head. Following three in vitro passages, a mutant VN04 virus (K193E) that was resistant to 22F was isolated. In contrast, no viruses resistant to any of the 3 IgG1 s (D8, F10, or A66) were identified. While these experiments cannot prove that escape mutants with unimpaired viral fitness will never arise, they clearly support the notion that the pocket is more refractory than epitopes in the head. Notwithstanding, if such mutants should arise, new reactive nAbs can be identified using the disclosed methods, or other of the disclosed HA stem antibodies that are engineered to have even broader spectrum reactivity (Sui et al., Broadening of neutralization activity to directly block a dominant antibody-driven SARS-coronavirus evolution pathway. *PLoS Pathog* 4, e1000197 (2008)) can be used.

3. Discussion

Prior to the present study, the vast majority of nAbs isolated against influenza A virus have targeted the receptor-binding head and lacked broad cross-neutralizing activity. However, a murine nAb, termed C179 (Okuno et al., A common neutralizing epitope conserved between the hemagglutinins of influenza A virus H1 and H2 strains. *J Virol* 67, 2552-8 (1993)), was positively selected on the basis of its cross-neutralization properties (of H1 and H2 subtypes), and subsequently shown to neutralize H5, but not Group 2 subtypes (Okuno et al., A common neutralizing epitope conserved between the hemagglutinins of influenza A virus H1 and H2 stains. *J Virol* 67, 2552-8 (1993); Smirnov et al., An epitope shared by the hemagglutinins of H1, H2, H5, and H6 subtypes of influenza A virus. *Acta Virol* 43, 237-44 (1999)). Moreover, C179 was shown to block membrane fusion rather than cell attachment and to protect mice against viral challenge (Smirnov et al., Prevention and treatment of bronchopneumonia in mice caused by mouse-adapted variant of avian H5N2 influenza A virus using monoclonal antibody against conserved epitope in the HA stem region. *Arch Virol* 145, 1733-41 (2000)), although a detailed mechanism was not reported. The activities of C179 and F10 were compared and found that both showed similar binding towards H5. F10 was found to efficiently compete with C179 for binding to H5, but not vice versa. Furthermore, the point mutant V52$_2$E abrogated binding to both Abs, while T318$_1$K only affected C179 binding. These results suggest that F10 and C179 have partially overlapping epitopes and that their modes of action are similar.

The manner in which HA was presented to the antibody phage display library in this study seems to have been helpful in presenting the stem portion, since similar attempts to isolate broadly nAbs using cell-surface expressed HA showed only partial success against H5, and most Abs recognized linear epitopes (Lim et al., Neutralizing human monoclonal antibody against H5N1 influenza HA selected from a Fab-phage display library. *Virol J* 5, 130 (2008)). As noted above, nAbs that utilize the same VH germline gene (IGHV1-69 or "VH1-69") were repeatedly isolated. Huang et al. (Structural basis of tyrosine sulfation and VH-gene usage in antibodies that recognize the HIV type 1 coreceptor-binding site on gp120. *Proc Natl Acad Sci USA* 101, 2706-11 (2004)) have pointed out that this is the only VH gene that consistently encodes 2 hydrophobic residues at the tip of its CDR-H2 loop: indeed, it is the only germline gene to encode a Phe at this position, which makes several critical interactions with H5. Moreover, the "type 2" H2 loop, which is long and compact, is only predicted to occur in 4 out of the ~50 human germline genes. These factors can explain at least in part the remarkable ability of nAbs derived from this germline gene to cross-react with viral epitopes: their unusual ability to bind to conserved hydrophobic pockets. Such pockets are likely to have an important function and for this reason they are often cryptic in the unactivated state of the antigen. For example, VH1-69 is the predominant gene utilized by a group of CD4-induced ("CD4i") nAbs raised against the HIV-1 surface glycoprotein, gp120, where the "pocket" is part of a conserved co-receptor binding site that is only exposed transiently upon binding to its primary receptor, CD4 (Huang et al. (2004)). Similarly, an antibody raised against the HIV gp41 trimeric "inner-core" fusion protein intermediate utilizes the hydrophobic tip of its VH1-69 CDR-H2 loop to insert into a conserved hydrophobic pocket that blocks further assembly to the fusion-competent 6-helix structure (Luftig et al., Structural basis for HIV-1 neutralization by a gp41 fusion intermediate-directed antibody. *Nat Struct Mol Biol* 13, 740-7 (2006)). In vivo, B cells carrying the VH1-69 gene are the primary mediators of innate defense against HCV infection, generating antibodies against its membrane fusion glycoprotein, E2 (Chan et al., V(H)1-69 gene is preferentially used by hepatitis C virus-associated B cell lymphomas and by normal B cells responding to the E2 viral antigen. *Blood* 97, 1023-6 (2001)), although the epitope and mode of action have not been determined. Notably, as disclosed herein, VH1-69 is not the only germline that is suitable for achieving neutralization in a similar manner. Another recent example is a nAb against Ebola virus surface glycoprotein, KZ52, which uses the VH3-21 germline (Lee et al., Structure of the Ebola virus glycoprotein bound to an antibody from a human survivor. *Nature* 454, 177-82 (2008)). However, the realization and discovery here of their common ability to lock viral envelope proteins into a non-fusogenic conformation represents the discovery of a general strategy for broad-spectrum and/or potent viral neutralization.

Recent work using immune-based phage-display libraries generated from B cell populations of patients who survived H5N1 infection resulted in the isolation of three human nAbs that neutralized both H1 and H5 viral strains. The authors postulated that the reason for survival was an effective humoral immune response mediated by such nAb-generating B cells in vivo (Kashyap et al., Combinatorial antibody libraries from survivors of the Turkish H5N1 avian influenza outbreak reveal virus neutralization strategies. *Proc Natl Acad Sci USA* 105, 5986-91 (2008)), although no control populations were studied. Analysis of their data indicates that the antibodies are also derived from the VH1-69 germline gene, and share other key characteristics, including the Met-Phe pair in CDR-H2 and a tyrosine at the tip of CDR-H3.

As discussed earlier, the broad-spectrum nAbs described herein are not generated/expanded during successive rounds of influenza infection and repeated vaccination. Only the disclosed methods have been effective to produce such antibodies consistently and repeatedly. It is unlikely that the F10 epitope provokes self-tolerance mechanism(s) via auto-antigen mimicry (Scherer et al., Difficulties in eliciting broadly neutralizing anti-HIV antibodies are not explained by cardiolipin autoreactivity. *Aids* 21, 2131-9 (2007)). Rather, an immunodominant Ab response to the highly-exposed globular head can overwhelm the Ab response to the F10-epitope. Thus, eliminating or reducing the antigenicity of the head region of HA provides a composition that can be used to generate an immune to the HA stem region in vivo. It is not surprising that many viruses are highly adept at keeping their most critical (and conserved) determinants of pathogenesis cryptic, in which case subunit-based vaccines as described herein, such as those utilizing properly presented fragments of F10 or F10-like epitopes, for example, can provide distinct advantages over whole-virus-based approaches for the induction of broad spectrum nAbs in vivo (Selvarajah et al., Focused dampening of antibody response to the immunodominant variable loops by engineered soluble gp140. AIDS Res Hum Retroviruses 24, 301-14 (2008); Scheerlinck et al., Redistribution of a murine humoral immune response following removal of an immunodominant B cell epitope from a recombinant fusion protein, *Mol Immunol* 30, 733-9 (1993)).

In summary, in vitro methodologies were used to isolate a family of high affinity broad-spectrum human nAbs against HA that show potent in vitro and in vivo efficacy against both highly pathogenic H5N1s and H1N1s. The nAbs inhibit the post-attachment fusion process by recognizing a highly conserved epitope within the stem region of HA at a point where key elements of the conformational change are brought into close apposition. This region was shown to be recalcitrant to the generation of escape mutants. Thus, the disclosed antibodies can be used for passive immunotherapy, either alone or in combination with small molecule inhibitors. Finally, structural work pinpoints the reasons why Group 2 HAs do not bind the nAbs described here: despite surface sequence similarities, they form a structurally distinct group, but one that is also highly conserved and therefore can be targeted for production of Group 2-reactive antibodies.

When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will, be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will the clearly understood that, although a number of publications are referred to herein, such reference does not constitute an admission that any of these documents forms part of the common general knowledge in the art.

TABLE 7

Contact residues at the H5-F10 interface

| | FRH1 | CDRH1 | | | | CDRH2 | | | CDRH3 | | | | |
|---|---|---|---|---|---|---|---|---|---|---|---|---|---|
| F10 | S25 | V27 | T28 | S30 | S31 | M54 | F55 | T57 | P100 | S101 | Y102 | I103 | S105 |
| HA1 | S291 M292 | S291 | | Q40 | | H38 | H18 H38 | | | | | | |
| HA2 | I56 | V52 N53 | | I45 T49 | W21 I45 | V18 D19 G20 W21 | V18 | Q42 | Q42 | D19 K38 T41 Q42 I45 | D19 K38 | K38 | |

It is understood that the disclosed method and compositions are not limited to the particular methodology, protocols, and reagents described as these may vary. It is also to be understood that the terminology used herein is for the purpose of describing particular embodiments only, and is not intended to limit t be scope of the present invention which will be limited only by the appended claims.

It must be noted that as used herein and in the appended claims, the singular forms "a", "an", and "the" include plural reference unless the context clearly dictates otherwise. Thus, for example, reference to "an antibody" includes a plurality of such antibodies, reference to "the antibody" is a reference to one or more antibodies and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

Although particular embodiments have been disclosed herein in detail, this has been done by way of example for purposes of illustration only, and is not intended to be limiting with respect to the scope of the appended claims, which, follow. In particular, it is contemplated by the inventors that various substitutions, alterations, and modifications may be made to the disclosed subject matter without departing from the spirit and scope of the disclosed subject matter as defined by the claims. Other aspects, advantages, and modifications considered to the within the scope of the following claims. The claims presented are representative of the subject matter disclosed herein. Other, unclaimed subject matter is also contemplated. Applicants reserve the right to pursue such subject matter in later claims.

What is claimed is:

1. A synthetic immunogen comprising an epitope or epitope unit recognized by a monoclonal antibody directed to the stem region of hemagglutinin protein of an influenza virus, wherein the epitope comprises at least 4 amino acid residues selected from the group consisting of amino acid residues 17, 18, 38, 39, 40 and 291 of HA1 and amino acid residues 18, 19, 20, 21, 38, 41, 42, 45, 49, 52, 53, 56, and 111 of HA2 in accordance with the H3 numbering system when said hemagglutinin is in the neutral pH conformation.

2. The immunogen of claim 1, wherein said antibody binds both the HA1 and HA2 peptide.

3. The immunogen of claim 1, wherein said epitope is the F10 epitope.

4. The immunogen of claim 1, wherein the antibody is monoclonal antibody D7, D8, F10, G17, H40, A66, D80, E88, E90, or H98.

5. The immunogen of claim 1, wherein the antibody is a monoclonal antibody that competes with the binding of monoclonal antibody D7, D8, F10, G17, H40, A66, D80, E88, E90, or H98 to the HA protein.

6. The immunogen of claim 1, wherein said immunogen is a peptide or a synthetic peptide.

7. The immunogen of claim 1, wherein the epitope comprises amino acid residues 18, 38, 39, 40 and 291 of HA1 and amino acid residues 18, 19, 20, 21, 38, 41, 42, 45, 49, 52, 53, and 56 of HA2 when said hemagglutinin in the neutral pH conformation.

8. The immunogen of claim 1, wherein the amino acid residues 17 18, 38, 40, and 291 of HA1 comprise the amino acid residues of Table 3.

9. The immunogen of claim 1, wherein the amino acid residues 18, 19, 20, 21, 38, 41, 42, 45, 49, 52, 53, 56, and 111 of HA2 comprise the amino acid residues of Table 3.

10. A nucleic acid encoding the immunogen of claim 8 or claim 9.

11. The immunogen of claim 1, further comprising an adjuvant.

12. The immunogen of claim 1, wherein said immunogen is conjugated to a carrier.

13. A composition comprising the immunogen of claim 1 together with one or more pharmaceutically acceptable excipients, diluents, and/or adjuvants.

* * * * *

SEQUENCE LISTING

```
<160> NUMBER OF SEQ ID NOS: 141

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Gly Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Tyr Tyr Gly Gly Phe Asp Val Trp Gly
            100                 105                 110

Gln Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 2

Gln Pro Val Leu Thr Gln Pro Pro Ser Ala Ser Gly Ser Pro Gly Gln
1               5                   10                  15

Arg Val Thr Ile Ser Cys Thr Gly Ser Ser Ser Asn Ile Gly Asn Tyr
            20                  25                  30

Val Ala Trp Tyr Gln Gln Lys Pro Gly Gln Ala Pro Lys Leu Leu Ile
        35                  40                  45

Tyr Ser Asn Ser Asp Arg Pro Ser Gly Ile Pro Asp Arg Phe Ser Gly
    50                  55                  60

Ser Arg Ser Gly Thr Thr Ala Ser Leu Thr Ile Ser Gly Leu Gln Pro
65                  70                  75                  80

Glu Asp Glu Ala Asp Tyr Tyr Cys Gln Ser Tyr Asp Ser Leu Ser Ala
                85                  90                  95

Tyr Val Phe Gly Gly Gly Thr Lys Leu Thr Val Leu
            100                 105
```

```
<210> SEQ ID NO 3
<211> LENGTH: 98
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 4
<211> LENGTH: 122
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Pro Gly Gly Ile Phe Asn Thr Asn
            20                  25                  30

Ala Phe Ser Trp Val Arg Gln Ala Pro Gly Gln Gly Leu Glu Trp Val
        35                  40                  45

Gly Gly Val Ile Pro Leu Phe Arg Thr Ala Ser Tyr Ala Gln Asn Val
    50                  55                  60

Gln Gly Arg Val Thr Ile Thr Ala Asp Glu Ser Thr Asn Thr Ala Tyr
65                  70                  75                  80

Met Glu Leu Thr Ser Leu Arg Ser Ala Asp Thr Ala Val Tyr Tyr Cys
                85                  90                  95

Ala Arg Ser Ser Gly Tyr His Phe Gly Arg Ser His Phe Asp Ser Trp
            100                 105                 110

Gly Leu Gly Thr Leu Val Thr Val Ser Ser
        115                 120

<210> SEQ ID NO 5
<211> LENGTH: 121
<212> TYPE: PRT
<213> ORGANISM: Homo sapiens

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Ala Phe Thr Trp Val Arg Gln Ala Pro Gly Gln Gly Leu Glu Trp Met
        35                  40                  45

Gly Gly Ile Ile Gly Met Phe Gly Thr Ala Asn Tyr Ala Gln Lys Phe
    50                  55                  60
```

```
Gln Gly Arg Val Thr Ile Thr Ala Asp Glu Leu Thr Thr Ala Tyr
 65                  70                  75                  80

Met Glu Leu Ser Ser Leu Thr Ser Glu Asp Thr Ala Leu Tyr Tyr Cys
                 85                  90                  95

Ala Arg Ser Gly Leu Tyr Tyr Tyr Glu Ser Ser Leu Asp Tyr Trp Gly
                100                 105                 110

Gln Gly Thr Leu Val Thr Val Ser Ser
            115                 120

<210> SEQ ID NO 6
<211> LENGTH: 124
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
  1               5                  10                  15

Ser Val Lys Val Ser Cys Thr Ser Ser Glu Val Thr Phe Ser Ser Phe
                 20                  25                  30

Ala Ile Ser Trp Val Arg Gln Ala Pro Gly Gln Gly Leu Glu Trp Leu
                 35                  40                  45

Gly Gly Ile Ser Pro Met Phe Gly Thr Pro Asn Tyr Ala Gln Lys Phe
         50                  55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                 85                  90                  95

Ala Arg Ser Pro Ser Tyr Ile Cys Ser Gly Gly Thr Cys Val Phe Asp
                100                 105                 110

His Trp Gly Gln Gly Thr Leu Val Thr Val Ser Ser
            115                 120

<210> SEQ ID NO 7
<211> LENGTH: 122
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
  1               5                  10                  15

Ser Val Lys Val Ser Cys Lys Thr Ser Gly Val Thr Phe Ser Ser Tyr
                 20                  25                  30

Ala Ile Ser Trp Val Arg Gln Ala Pro Gly Gln Gly Leu Glu Trp Met
                 35                  40                  45

Gly Gly Ile Ile Gly Val Phe Gly Val Pro Lys Tyr Ala Gln Lys Phe
         50                  55                  60

Gln Gly Arg Val Thr Ile Thr Ala Asp Lys Pro Thr Ser Thr Val Tyr
 65                  70                  75                  80

Met Glu Leu Asn Ser Leu Arg Ala Glu Asp Thr Ala Val Tyr Tyr Cys
                 85                  90                  95

Ala Arg Glu Pro Gly Tyr Tyr Val Gly Lys Asn Gly Phe Asp Val Trp
                100                 105                 110

Gly Gln Gly Thr Met Val Thr Val Ser Ser
            115                 120

<210> SEQ ID NO 8
<211> LENGTH: 126
```

<212> TYPE: PRT
<213> ORGANISM: Homo sapiens

<400> SEQUENCE: 8

```
Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Met Thr Gly Gly Thr Asn Tyr Ala Gln Lys Phe
        50                  55                  60

Gln Val Trp Val Thr Met Thr Arg Asp Thr Ser Ile Asn Thr Ala Tyr
65                  70                  75                  80

Met Glu Val Thr Arg Leu Thr Ser Asp Asp Thr Ala Val Tyr Tyr Cys
                85                  90                  95

Ala Arg Gly Ala Ser Val Leu Arg Tyr Phe Asp Trp Gln Pro Glu Ala
                100                 105                 110

Leu Asp Ile Trp Gly Leu Gly Thr Thr Val Thr Val Ser Ser
            115                 120                 125
```

<210> SEQ ID NO 9
<211> LENGTH: 124
<212> TYPE: PRT
<213> ORGANISM: Homo sapiens

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Met Thr
                20                  25                  30

Ala Phe Thr Trp Leu Arg Gln Ala Pro Gly Gln Gly Leu Glu Trp Met
            35                  40                  45

Gly Gly Ile Ser Pro Ile Phe Arg Thr Pro Lys Asn Tyr Ala Gln Lys
        50                  55                  60

Phe Gln Gly Arg Val Thr Ile Thr Ala Asp Glu Ser Thr Asn Thr Ala
65                  70                  75                  80

Asn Met Glu Leu Thr Ser Leu Lys Ser Glu Asp Thr Ala Val Tyr Tyr
                85                  90                  95

Cys Ala Arg Thr Leu Ser Ser Tyr Gln Pro Asn Asn Asp Ala Phe Ala
                100                 105                 110

Ile Trp Gly Gln Gly Thr Met Val Thr Val Ser Ser
            115                 120
```

<210> SEQ ID NO 10
<211> LENGTH: 111
<212> TYPE: PRT
<213> ORGANISM: Homo sapiens

<400> SEQUENCE: 10

```
Asn Phe Met Leu Thr Gln Pro His Ser Val Ser Ala Ser Pro Gly Lys
1               5                   10                  15

Thr Val Thr Ile Ser Cys Thr Gly Ser Ser Asn Ile Ala Ala Asn
                20                  25                  30

Tyr Val Gln Trp Tyr Gln Gln Arg Pro Gly Ser Ala Pro Thr Thr Val
            35                  40                  45

Ile Tyr Glu Asp Asp Arg Arg Pro Ser Gly Val Pro Asp Arg Phe Ser
```

```
                    50                  55                  60
Gly Ser Ile Asp Arg Ser Ser Asn Ser Ala Ser Leu Thr Ile Ser Gly
 65                  70                  75                  80

Leu Gln Thr Glu Asp Glu Ala Asp Tyr Tyr Cys Gln Ser Tyr Asp Thr
                 85                  90                  95

Asn Asn His Ala Val Phe Gly Gly Gly Thr His Leu Thr Val Leu
            100                 105                 110
```

<210> SEQ ID NO 11
<211> LENGTH: 110
<212> TYPE: PRT
<213> ORGANISM: Homo sapiens

<400> SEQUENCE: 11

```
Gln Ser Val Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Glu Val Thr Lys Arg Pro Ser Gly Val Pro Asp Arg Phe
 50                  55                  60

Ser Ala Ser Lys Ser Gly Asn Thr Ala Ser Leu Thr Val Ser Gly Leu
 65                  70                  75                  80

Gln Ala Glu Asp Glu Ala Asp Tyr Phe Cys Cys Ser Tyr Ala Gly His
                 85                  90                  95

Ser Ala Tyr Val Phe Gly Thr Gly Thr Lys Val Thr Val Leu
            100                 105                 110
```

<210> SEQ ID NO 12
<211> LENGTH: 110
<212> TYPE: PRT
<213> ORGANISM: Homo sapiens

<400> SEQUENCE: 12

```
Gln Pro Gly Leu Thr Gln Pro Pro Ser Val Ser Lys Gly Leu Arg Gln
 1               5                  10                  15

Thr Ala Thr Leu Thr Cys Thr Gly Asn Ser Asn Asn Val Gly Asn Gln
                20                  25                  30

Gly Ala Ala Trp Leu Gln Gln Gly Gln Gly His Pro Pro Lys Leu Leu
            35                  40                  45

Ile Tyr Arg Asn Asn Asp Arg Pro Ser Gly Ile Ser Glu Arg Phe Ser
 50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Thr Trp Asp Ser Ser Leu
                 85                  90                  95

Ser Ala Val Val Phe Gly Gly Gly Thr Lys Leu Thr Val Leu
            100                 105                 110
```

<210> SEQ ID NO 13
<211> LENGTH: 110
<212> TYPE: PRT
<213> ORGANISM: Homo sapiens

<400> SEQUENCE: 13

```
Ser Tyr Glu Leu Thr Gln Pro Pro Ser Ala Ser Lys Gly Leu Arg Gln
 1               5                  10                  15
```

```
Thr Ala Ile Leu Thr Cys Thr Gly Asp Ser Asn Asn Val Gly His Gln
            20                  25                  30

Gly Thr Ala Trp Leu Gln Gln His Gln Gly His Pro Pro Lys Leu Leu
        35                  40                  45

Ser Tyr Arg Asn Gly Asn Arg Pro Ser Gly Ile Ser Glu Arg Phe Ser
 50                  55                  60

Ala Ser Arg Ser Gly Asn Thr Ala Ser Leu Thr Ile Ile Gly Leu Gln
 65                  70                  75                  80

Pro Glu Asp Glu Ala Asp Tyr Tyr Cys Ser Val Trp Asp Ser Ser Leu
                85                  90                  95

Ser Ala Trp Val Phe Gly Gly Gly Thr Lys Leu Thr Val Leu
            100                 105                 110

<210> SEQ ID NO 14
<211> LENGTH: 110
<212> TYPE: PRT
<213> ORGANISM: Homo sapiens

<400> SEQUENCE: 14

Gln Pro Val Leu Thr Gln Pro Pro Ser Val Ser Val Ala Pro Gly Gln
 1               5                  10                  15

Thr Ala Ser Ile Pro Cys Gly Gly Ser Ser Asn Asn Ile Gly Gly Tyr
            20                  25                  30

Ser Val His Trp Tyr Gln Gln Lys Pro Gly Gln Ala Pro Leu Leu Leu
        35                  40                  45

Ile Tyr Asp Asp Lys Asp Arg Pro Ser Gly Ile Pro Glu Arg Phe Ser
 50                  55                  60

Gly Ser Asn Ser Gly Ser Thr Ala Thr Leu Thr Ile Ser Arg Val Glu
 65                  70                  75                  80

Ala Gly Asp Glu Gly Asp Tyr Tyr Cys Gln Val Trp Asp Ser Gly Asn
                85                  90                  95

Asp Arg Pro Leu Phe Gly Gly Gly Thr Lys Leu Thr Val Leu
            100                 105                 110

<210> SEQ ID NO 15
<211> LENGTH: 107
<212> TYPE: PRT
<213> ORGANISM: Homo sapiens

<400> SEQUENCE: 15

Glu Ile Val Leu Thr Gln Ser Pro Ala Thr Leu Leu Ser Pro Gly Glu
 1               5                  10                  15

Arg Ala Thr Leu Ser Cys Arg Ala Ser Gln Ser Val Ser Ser Tyr Phe
            20                  25                  30

Ala Trp Tyr Gln Gln Lys Pro Gly Gln Ala Pro Arg Leu Leu Ile Tyr
        35                  40                  45

Asp Ala Ser Asn Arg Ala Thr Gly Ile Pro Ala Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Phe Cys Gln Gln Tyr Gly Ser Leu Ser Pro Gln
                85                  90                  95

Val Phe Gly Gln Gly Thr Arg Leu Glu Ile Lys
            100                 105

<210> SEQ ID NO 16
```

-continued

<211> LENGTH: 108
<212> TYPE: PRT
<213> ORGANISM: Homo sapiens

<400> SEQUENCE: 16

Glu Ile Val Leu Thr Gln Ser Pro Gly Thr Leu Leu Ser Pro Gly Glu
1               5                   10                  15

Arg Ala Thr Leu Ser Cys Arg Ala Ser Gln Ser Leu Ser Ser Lys Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Ser Cys Gln Gln Tyr Asp Gly Leu Val Pro
                85                  90                  95

Arg Thr Phe Gly Gln Gly Thr Val Glu Ile Lys
            100                 105

<210> SEQ ID NO 17
<211> LENGTH: 110
<212> TYPE: PRT
<213> ORGANISM: Homo sapiens

<400> SEQUENCE: 17

Leu Pro Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ile Gly Leu Arg
65                  70                  75                  80

Pro Glu Asp Glu Ala Asp Tyr Tyr Cys Gln Ser Tyr Asp Ser Arg Leu
                85                  90                  95

Ser Ala Ser Leu Phe Gly Thr Gly Thr Thr Val Thr Val Leu
            100                 105                 110

<210> SEQ ID NO 18
<211> LENGTH: 107
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Val Thr Ile Ser Thr Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Arg Gln Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

```
Asp Phe Ala Val Tyr Tyr Cys Gln Gln Tyr Asp Ser Leu Ser Pro Tyr
                85                  90                  95

Thr Phe Gly Gln Gly Thr Lys Val Glu Ile Lys
            100                 105
```

<210> SEQ ID NO 19
<211> LENGTH: 110
<212> TYPE: PRT
<213> ORGANISM: Homo sapiens

<400> SEQUENCE: 19

```
Ser Tyr Glu Leu Thr Gln Pro Pro Ser Ala Ser Gly Lys His Gly Gln
1               5                   10                  15

Arg Val Thr Ile Ser Cys Ser Gly Gly Thr Ser Asn Ile Gly Arg Asn
            20                  25                  30

His Val Asn Trp Tyr Gln Gln Leu Pro Gly Thr Ala Pro Lys Leu Leu
        35                  40                  45

Ile Tyr Ser Asn Glu Gln Arg Pro Ser Gly Val Pro Asp Arg Phe Ser
    50                  55                  60

Gly Ser Lys Ser Gly Thr Ser Ala Ser Leu Ala Val Ser Gly Leu Gln
65                  70                  75                  80

Ser Glu Asp Glu Ala Asp Tyr Tyr Cys Ala Ser Trp Asp Asp Asn Leu
                85                  90                  95

Ser Gly Trp Val Phe Gly Gly Gly Thr Lys Leu Thr Val Leu
            100                 105                 110
```

<210> SEQ ID NO 20
<211> LENGTH: 4
<212> TYPE: PRT
<213> ORGANISM: Homo sapiens

<400> SEQUENCE: 20

Val Asp Gly Trp
1

<210> SEQ ID NO 21
<211> LENGTH: 4
<212> TYPE: PRT
<213> ORGANISM: Homo sapiens

<400> SEQUENCE: 21

Ile Asp Gly Trp
1

<210> SEQ ID NO 22
<211> LENGTH: 4
<212> TYPE: PRT
<213> ORGANISM: Homo sapiens

<400> SEQUENCE: 22

Ile Asn Gly Trp
1

<210> SEQ ID NO 23
<211> LENGTH: 4
<212> TYPE: PRT
<213> ORGANISM: Homo sapiens

<400> SEQUENCE: 23

Val Ala Gly Trp
1

<210> SEQ ID NO 24
<211> LENGTH: 122
<212> TYPE: PRT
<213> ORGANISM: Homo sapiens

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Thr Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Gly Val Phe Gly Val Pro Lys Tyr Ala Gln Asn Phe
    50                  55                  60

Gln Gly Arg Val Thr Ile Thr Ala Asp Lys Pro Thr Ser Thr Val Tyr
65                  70                  75                  80

Met Glu Leu Asn Ser Leu Arg Ala Glu Asp Thr Ala Val Tyr Tyr Cys
                85                  90                  95

Ala Arg Glu Pro Gly Tyr Tyr Val Gly Lys Asn Gly Phe Asp Val Trp
            100                 105                 110

Gly Gln Gly Thr Met Val Thr Val Ser Ser
        115                 120

<210> SEQ ID NO 25
<211> LENGTH: 330
<212> TYPE: DNA
<213> ORGANISM: Homo sapiens

<400> SEQUENCE: 25
cagcctgggc tgactcagcc accctcggtg tccaagggct tgagacagac cgccacactc      60
acctgcactg ggaacagcaa caatgttggc aaccaaggag cagcttggct gcagcagcac     120
cagggccacc ctcccaaact cctatcctac aggaataatg accggccctc agggatctca     180
gagagattct ctgcatccag gtcaggaaac acagcctccc tgaccattac tggactccag     240
cctgaggacg aggctgacta ttactgctca acatgggaca gcagcctcag tgctgtggta     300
ttcggcggag ggaccaagct gaccgtccta                                       330

<210> SEQ ID NO 26
<211> LENGTH: 110
<212> TYPE: PRT
<213> ORGANISM: Homo sapiens

<400> SEQUENCE: 26

Ser Tyr Glu Leu Thr Gln Pro Pro Ser Val Ser Lys Gly Leu Arg Gln
1               5                   10                  15

Thr Ala Ile Leu Thr Cys Thr Gly Asp Ser Asn Asn Val Gly His Gln
            20                  25                  30

Gly Thr Ala Trp Leu Gln Gln His Gln Gly His Pro Pro Lys Leu Leu
        35                  40                  45

Ser Tyr Arg Asn Gly Asn Arg Pro Ser Gly Ile Ser Glu Arg Phe Ser
    50                  55                  60

Ala Ser Arg Ser Gly Asn Thr Ala Ser Leu Thr Ile Ile Gly Leu Gln
65                  70                  75                  80

Pro Glu Asp Glu Ala Asp Tyr Tyr Cys Ser Val Trp Asp Ser Ser Leu
                85                  90                  95

Ser Ala Trp Val Phe Gly Gly Gly Thr Lys Leu Thr Val Leu

<210> SEQ ID NO 27
<211> LENGTH: 321
<212> TYPE: DNA
<213> ORGANISM: Homo sapiens

<400> SEQUENCE: 27
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagagg gtcccatca     180 aggttcagtg gcagtggatc tgggacagac ttcactctca ccattagcag cctgcagcct     240
gaagattttg cagtgtatta ctgtcagcag tatgatagtt caccgtacac ttttggccag     300
gggaccaagg tagagatcaa a                                                321

<210> SEQ ID NO 28
<211> LENGTH: 126
<212> TYPE: PRT
<213> ORGANISM: Homo sapiens

<400> SEQUENCE: 28

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Met Thr Gly Gly Thr Asn Tyr Ala Gln Lys Phe
        50                  55                  60

Gln Val Trp Val Thr Met Thr Arg Asp Thr Ser Ile Asn Thr Ala Tyr
65                  70                  75                  80

Met Glu Val Ser Arg Leu Thr Ser Asp Asp Thr Ala Val Tyr Tyr Cys
                85                  90                  95

Ala Arg Gly Ala Ser Val Leu Arg Tyr Phe Asp Trp Gln Pro Glu Ala
            100                 105                 110

Leu Asp Ile Trp Gly Leu Gly Thr Thr Val Thr Val Ser Ser
        115                 120                 125

<210> SEQ ID NO 29
<211> LENGTH: 366
<212> TYPE: DNA
<213> ORGANISM: Homo sapiens

<400> SEQUENCE: 29
caggtgcagc tggtgcaatc tggggctgaa gtgaagaagc ctggggcctc agtgaaggtc      60
tcctgcaaga cttctggagt caccttcagc agctatgcta tcagttgggt gcgacaggcc     120
cctggacaag gcttgagtg gatgggaggg atcatcggtg tctttggtgt accaaagtac     180
gcgcagaact tccagggcag agtcacaatt accgcggaca aaccgacgag tacagtctac     240
atggagctga acagcctgag agctgaggac acggccgtgt attactgtgc gagagagccc     300
gggtactacg taggaaagaa tggttttgat gtctggggcc aagggacaat ggtcaccgtc     360
tcttca                                                                  366

<210> SEQ ID NO 30
<211> LENGTH: 108

```
<212> TYPE: PRT
<213> ORGANISM: Homo sapiens

<400> SEQUENCE: 30

Gln Pro Val Leu Thr Gln Pro Ser Val Ser Val Ala Pro Gly Gln
1               5                   10                  15

Thr Ala Ser Ile Pro Cys Gly Gly Asn Asn Ile Gly Tyr Ser Val
                20                  25                  30

His Trp Tyr Gln Gln Lys Pro Gly Gln Ala Pro Leu Leu Val Ile Tyr
                35                  40                  45

Asp Asp Lys Asp Arg Pro Ser Gly Ile Pro Glu Arg Phe Ser Gly Ala
                50                  55                  60

Asn Ser Gly Ser Thr Ala Thr Leu Thr Ile Ser Arg Val Glu Ala Gly
65              70                  75                  80

Asp Glu Gly Asp Tyr Tyr Cys Gln Val Trp Asp Ser Gly Asn Asp Arg
                85                  90                  95

Pro Leu Phe Gly Gly Gly Thr Lys Leu Thr Val Leu
            100                 105

<210> SEQ ID NO 31
<211> LENGTH: 330
<212> TYPE: DNA
<213> ORGANISM: Homo sapiens

<400> SEQUENCE: 31
tcctatgagc tgactcagcc accctcggtg tccaagggct tgagacagac cgccatactc      60
acctgcactg gagacagcaa caatgttggc caccaaggta cagcttggct gcaacaacac     120
cagggccacc ctcccaaact cctatcctac aggaatggca accggccctc agggatctca     180
gagagattct ctgcatccag gtcaggaaat acagcctccc tgaccattat ggactccag      240 cctgaggacg aggctgacta ctactgctca gtatgggaca gcagcctcag tgcctgggtg     300
ttcggcggag ggaccaagct gaccgtccta                                      330

<210> SEQ ID NO 32
<211> LENGTH: 123
<212> TYPE: PRT
<213> ORGANISM: Homo sapiens

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Met Thr
                20                  25                  30

Ala Phe Thr Trp Leu Arg Gln Ala Pro Gly Gln Gly Leu Glu Trp Met
                35                  40                  45

Gly Gly Ile Ser Pro Ile Phe Arg Thr Pro Lys Tyr Ala Gln Lys Phe
                50                  55                  60

Gln Gly Arg Val Thr Ile Thr Ala Asp Glu Ser Thr Asn Thr Ala Asn
65              70                  75                  80

Met Glu Leu Thr Ser Leu Lys Ser Glu Asp Thr Ala Val Tyr Tyr Cys
                85                  90                  95

Ala Arg Thr Leu Ser Ser Tyr Gln Pro Asn Asn Asp Ala Phe Ala Ile
                100                 105                 110

Trp Gly Gln Gly Thr Met Val Thr Val Ser Ser
            115                 120
```

<210> SEQ ID NO 33
<211> LENGTH: 378
<212> TYPE: DNA
<213> ORGANISM: Homo sapiens

<400> SEQUENCE: 33

```
caggtgcagc tggtgcagtc tggggctgag gtgaggaagc ctggggcctc agtgaaggtc      60
tcatgtaagg cttctggata caccttcacc ggttattata ttcactgggt gcgacaggcc     120
cctggacaag gacttgagtg gatgggttgg atcaaccctg tgactggtgg cacaaactat     180
gcacagaagt tcaggtctg gtcaccatg acccgggaca cgtccatcaa cacagcctac      240
atggaggtga gcaggctgac atctgacgac acggccgtgt attactgtgc gagggggggct    300
tccgtattac gatattttga ctggcagccc gaggctcttg atatctgggg cctcgggacc    360
acggtcaccg tctcctca                                                  378
```

<210> SEQ ID NO 34
<211> LENGTH: 106
<212> TYPE: PRT
<213> ORGANISM: Homo sapiens

<400> SEQUENCE: 34

```
Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Phe Cys Gln Gln Tyr Gly Ser Ser Pro Gln
                85                  90                  95

Phe Gly Gln Gly Thr Arg Leu Glu Ile Lys
            100                 105
```

<210> SEQ ID NO 35
<211> LENGTH: 324
<212> TYPE: DNA
<213> ORGANISM: Homo sapiens

<400> SEQUENCE: 35

```
cagcctgtgc tgactcagcc accctcggtg tcagtggccc caggacagac ggccagcatt      60
ccctgtgggg gaaacaacat tggaggctac agtgtacact ggtaccaaca aaagccgggc    120
caggccccc tcttggtcat ttatgacgat aaagaccggc cctcagggat ccctgagcga    180
ttctctggcg ccaactctgg gagcacggcc accctgacaa tcagcagggt cgaagccggg    240
gatgagggcg actactactg tcaggtgtgg gatagtggta tgatcgtcc gctgttcggc    300
ggagggacca agctgaccgt ccta                                           324
```

<210> SEQ ID NO 36
<211> LENGTH: 123
<212> TYPE: PRT
<213> ORGANISM: Homo sapiens

<400> SEQUENCE: 36

```
Gln Val Gln Leu Val Gln Ser Gly Ala Glu Val Lys Lys Pro Gly Ser
```

```
 1               5                  10                 15
Ser Val Lys Val Ser Cys Lys Ala Ser Gly Gly Pro Phe Ser Met Thr
               20                  25                 30

Ala Phe Thr Trp Leu Arg Gln Ala Pro Gly Gln Gly Leu Glu Trp Met
               35                  40                 45

Gly Gly Ile Ser Pro Ile Phe Arg Thr Pro Lys Tyr Ala Gln Lys Phe
       50                  55                 60

Gln Gly Arg Val Thr Ile Thr Ala Asp Glu Ser Thr Asn Thr Ala Asn
65                  70                  75                 80

Met Glu Leu Thr Ser Leu Lys Ser Glu Asp Thr Ala Val Tyr Tyr Cys
                   85                  90                 95

Ala Arg Thr Leu Ser Ser Tyr Gln Pro Asn Asn Asp Ala Phe Ala Ile
               100                 105                110

Trp Gly Gln Gly Thr Met Val Thr Val Ser Ser
               115                 120
```

<210> SEQ ID NO 37
<211> LENGTH: 369
<212> TYPE: DNA
<213> ORGANISM: Homo sapiens

<400> SEQUENCE: 37

```
caggtgcagc tggtgcagtc tggggctgaa gtgaagaagc ctggctcctc ggtgaaggtt      60
tcctgcaagg cttctggagg ccccttcagc atgactgctt tcacctggct gcgacaggcc     120
cctggacaag gcttgagtg gatgggtggg atcagcccta tctttcgtac accgaagtac     180
gcacagaagt tccagggcag agtcacgatt accgcggacg aatccacgaa cacagccaac     240
atggagctga ccagcctgaa atctgaggac acggccgtgt attactgtgc gagaacccct     300
tcctcctacc aaccgaataa tgatgctttt gctatctggg gccaagggac aatggtcacc     360
gtctcttca                                                             369
```

<210> SEQ ID NO 38
<211> LENGTH: 110
<212> TYPE: PRT
<213> ORGANISM: Homo sapiens

<400> SEQUENCE: 38

```
Leu Pro Val Leu Thr Gln Pro Pro Ser Ala Ser Gly Thr Pro Gly Gln
1               5                  10                 15

Arg Val Thr Ile Ser Cys Ser Gly Ser Ser Asn Ile Gly Ser Asn
               20                  25                 30

Thr Val Asn Trp Tyr Gln Gln Leu Pro Gly Thr Ala Pro Lys Leu Leu
               35                  40                 45

Ile Tyr Ser Asn Asn Gln Arg Pro Ser Gly Val Pro Asp Arg Phe Ser
       50                  55                 60

Gly Ser Arg Ser Gly Thr Ser Ala Ser Leu Ala Ile Ile Gly Leu Arg
65                  70                  75                 80

Pro Glu Asp Glu Ala Asp Tyr Tyr Cys Gln Ser Tyr Asp Ser Arg Leu
                   85                  90                 95

Ser Ala Ser Leu Phe Gly Thr Gly Thr Thr Val Thr Val Leu
               100                 105                110
```

<210> SEQ ID NO 39
<211> LENGTH: 318
<212> TYPE: DNA
<213> ORGANISM: Homo sapiens

<400> SEQUENCE: 39

```
gaaattgtgt tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag actggagcct   240
gaagattttg cagtctattt ctgtcagcag tatggtagct cacctcaatt cggccaaggg   300
acacgactgg agattaaa                                                 318
```

<210> SEQ ID NO 40
<211> LENGTH: 369
<212> TYPE: DNA
<213> ORGANISM: Homo sapiens

<400> SEQUENCE: 40

```
caggtgcagc tggtgcagtc tggggctgaa gtgaagaagc ctggctcctc ggtgaaggtt    60
tcctgcaagg cttctggagg ccccttcagc atgactgctt tcacctggct gcgacaggcc   120
cctggacaag gcttgagtg gatggtggg atcagcccta tctttcgtac accgaagtac   180
gcacagaagt tccagggcag agtcacgatt accgcggacg aatccacgaa cacagccaac   240
atggagctga ccagcctgaa atctgaggac acggccgtgt attactgtgc gagaacccctt   300
tcctcctacc aaccgaataa tgatgctttt gctatctggg gccaagggac aatggtcacc   360
gtctcttca                                                           369
```

<210> SEQ ID NO 41
<211> LENGTH: 369
<212> TYPE: DNA
<213> ORGANISM: Homo sapiens

<400> SEQUENCE: 41

```
caggtgcagc tggtgcagtc tggggctgag gtgaagaagc ctgggtcctc ggtgaaggtc    60
tcctgcaagg cttctggagg caccttcagt gacaatgcta tcagctgggt gcgacaggcc   120
ccaggacaag gcttgagtg gatgggggc atcattccta tctttggaaa accaaactac   180
gcacagaagt tccagggcag agtcacgatt actgcggacg aatccacgag cacagcctac   240
atggacctga gagcctgag atctgaggac acggccgttt attactgtgc gagagattca   300
gacgcgtatt actatggttc gggggtatg gacgtctggg gccaaggcac cctggtcacc   360
gtctcctca                                                           369
```

<210> SEQ ID NO 42
<211> LENGTH: 330
<212> TYPE: DNA
<213> ORGANISM: Homo sapiens

<400> SEQUENCE: 42

```
ctgcctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg ccccccaaact cctcatctat agtaataatc agcggccctc agggtccct   180
gaccgattct ctggctccag gtcaggcacc tcagcctccc tggccatcat ggactccgg   240
cctgaggatg aagctgatta ttactgtcag tcgtatgaca gcaggctcag tgcttctctc   300
ttcggaactg ggaccacggt caccgtcctc                                    330
```

<210> SEQ ID NO 43
<211> LENGTH: 123
<212> TYPE: PRT
<213> ORGANISM: Homo sapiens

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Asn
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Asp Leu Arg Ser Leu Arg Ser Glu Asp Thr Ala Val Tyr Tyr Cys
                85                  90                  95

Ala Arg Asp Ser Asp Ala Tyr Tyr Gly Ser Gly Gly Met Asp Val
                100                 105                 110

Trp Gly Gln Gly Thr Leu Val Thr Val Ser Ser
            115                 120

<210> SEQ ID NO 44
<211> LENGTH: 335
<212> TYPE: DNA
<213> ORGANISM: Homo sapiens

<400> SEQUENCE: 44
ctgcctgtgc tgactcaatc atcctctgcc tctgcttccc tgggatcctc ggtcaagctc     60
acctgcactc tgagcagtgg catagtaac tacatcatcg catggcatca acagcagcca    120
gggaaggccc ctcggtactt gatgaaggtt aatagtgatg cagccacac caaggggggac    180 gggatccctg atcgcttctc aggctccagc tctggggctg accgctacct caccatctcc    240
aacctccagt ctgaggatga ggctagttat ttctgtgaga cctgggacac taagattcat    300
gtcttcggaa ctgggaccaa ggtctccgtc ctcag                               335

<210> SEQ ID NO 45
<211> LENGTH: 111
<212> TYPE: PRT
<213> ORGANISM: Homo sapiens

<400> SEQUENCE: 45

Leu Pro Val Leu Thr Gln Ser Ser Ser Ala Ser Ala Ser Leu Gly Ser
1               5                   10                  15

Ser Val Lys Leu Thr Cys Thr Leu Ser Ser Gly His Ser Asn Tyr Ile
            20                  25                  30

Ile Ala Trp His Gln Gln Pro Gly Lys Ala Pro Arg Tyr Leu Met
        35                  40                  45

Lys Val Asn Ser Asp Gly Ser His Thr Lys Gly Asp Gly Ile Pro Asp
    50                  55                  60

Arg Phe Ser Gly Ser Ser Ser Gly Ala Asp Arg Tyr Leu Thr Ile Ser
65                  70                  75                  80

Asn Leu Gln Ser Glu Asp Glu Ala Ser Tyr Phe Cys Glu Thr Trp Asp
                85                  90                  95

Thr Lys Ile His Val Phe Gly Thr Gly Thr Lys Val Ser Val Leu

<210> SEQ ID NO 46
<211> LENGTH: 363
<212> TYPE: DNA
<213> ORGANISM: Homo sapiens

<400> SEQUENCE: 46

```
caggtgcagc tggtgcagtc tggggctgag gtgaagaagc ctgggtcctc ggtgaaggtc    60
tcctgcaagg ctcctggagg tatcttcaac accaatgctt tcagctgggt ccgacaggcc   120
cctggacaag gtcttgagtg ggtgggaggg gtcatccctt tgtttcgaac agcaagctac   180
gcacagaacg tccagggcag agtcaccatt accgcggacg aatccacgaa cacagcctac   240
atggagctta ccagcctgag atctgcggac acggccgtgt attactgtgc gagaagtagt   300
ggttaccatt ttaggagtca ctttgactcc tggggcctgg aaccctggt  caccgtctcc   360
tca                                                                363
```

<210> SEQ ID NO 47
<211> LENGTH: 121
<212> TYPE: PRT
<213> ORGANISM: Homo sapiens

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Pro Gly Gly Ile Phe Asn Thr Asn
            20                  25                  30

Ala Phe Ser Trp Val Arg Gln Ala Pro Gly Gln Gly Leu Glu Trp Val
        35                  40                  45

Gly Gly Val Ile Pro Leu Phe Arg Thr Ala Ser Tyr Ala Gln Asn Val
    50                  55                  60

Gln Gly Arg Val Thr Ile Thr Ala Asp Glu Ser Thr Asn Thr Ala Tyr
65                  70                  75                  80

Met Glu Leu Thr Ser Leu Arg Ser Ala Asp Thr Ala Val Tyr Tyr Cys
                85                  90                  95

Ala Arg Ser Ser Gly Tyr His Phe Arg Ser His Phe Asp Ser Trp Gly
            100                 105                 110

Leu Gly Thr Leu Val Thr Val Ser Ser
        115                 120

<210> SEQ ID NO 48
<211> LENGTH: 363
<212> TYPE: DNA
<213> ORGANISM: Homo sapiens

<400> SEQUENCE: 48

```
caggtgcagc tggtgcaatc tggggctgag gtgaagaagc ctgggtcctc ggtgaaggtc    60
tcctgcaagg ctcctggagg tatcttcaac accaatgctt tcagctgggt ccgacaggcc   120
cctggacaag gtcttgagtg ggtgggaggg gtcatccctt tgtttcgaac agcaagctac   180
gcacagaacg tccagggcag agtcaccatt accgcggacg aatccacgaa cacagcctac   240
atggagctta ccagcctgag atctgcggac acggccgtgt attactgtgc gagaagtagt   300
ggttaccatt ttaggagtca ctttgactcc tggggcctgg aaccctggt  caccgtctcc   360
tca                                                                363
```

<210> SEQ ID NO 49
<211> LENGTH: 111
<212> TYPE: PRT
<213> ORGANISM: Homo sapiens

<400> SEQUENCE: 49

Asn Phe Met Leu Thr Gln Pro His Ser Val Ser Ala Ser Pro Gly Lys
1               5                   10                  15

Thr Val Thr Ile Ser Cys Thr Gly Ser Ser Gly Asn Ile Ala Ala Asn
            20                  25                  30

Tyr Val Gln Trp Tyr Gln Gln Arg Pro Gly Ser Ala Pro Thr Thr Val
        35                  40                  45

Ile Tyr Glu Asp Asp Arg Arg Pro Ser Gly Val Pro Asp Arg Phe Ser
50                  55                  60

Gly Ser Ile Asp Arg Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Thr
                85                  90                  95

Asn Asn His Ala Val Phe Gly Gly Gly Thr His Leu Thr Val Leu
            100                 105                 110

<210> SEQ ID NO 50
<211> LENGTH: 333
<212> TYPE: DNA
<213> ORGANISM: Homo sapiens

<400> SEQUENCE: 50
aattttatgc tgactcagcc ccactctgtg tcggcgtctc cggggaagac ggtgaccatc      60
tcctgcaccg gcagcagtgg caacattgcc gccaactatg tgcagtggta ccaacaacgt     120
ccgggcagtg cccccactac tgtgatctat gaggatgacc gaagaccctc tggggtccct     180
gatcggttct ctggctccat cgacaggtcc tccaactctg cctccctcac catctcagga    240
ctgaagactg aggacgaggc tgactactac tgtcagactt atgataccaa caatcatgct    300
gtgttcggag gaggcaccca cctgaccgtc ctc                                  333

<210> SEQ ID NO 51
<211> LENGTH: 110
<212> TYPE: PRT
<213> ORGANISM: Homo sapiens

<400> SEQUENCE: 51

Ser Tyr Glu Leu Thr Gln Pro Pro Ser Ala Ser Gly Lys His Gly Gln
1               5                   10                  15

Arg Val Thr Ile Ser Cys Ser Gly Gly Thr Ser Asn Ile Gly Arg Asn
            20                  25                  30

His Val Asn Trp Tyr Gln Gln Leu Pro Gly Thr Ala Pro Lys Leu Leu
        35                  40                  45

Ile Tyr Ser Asn Glu Gln Arg Pro Ser Gly Val Pro Asp Arg Phe Ser
50                  55                  60

Gly Ser Lys Ser Gly Thr Ser Ala Ser Leu Ala Val Ser Gly Leu Gln
65                  70                  75                  80

Ser Glu Asp Glu Ala Asp Tyr Tyr Cys Ala Ser Trp Asp Asp Asn Leu
                85                  90                  95

Ser Gly Trp Val Phe Gly Gly Gly Thr Lys Leu Thr Val Leu
            100                 105                 110

<210> SEQ ID NO 52

<210> SEQ ID NO 52
<211> LENGTH: 330
<212> TYPE: DNA
<213> ORGANISM: Homo sapiens

<400> SEQUENCE: 52

```
tcctatgagc tgactcagcc accctcagcg tctgggaaac acgggcagag ggtcaccatc    60
tcttgttctg gaggcacctc caacatcgga cgtaatcatg ttaactggta ccagcaactc   120
ccaggaacgg cccccaaact cctcatctat agtaatgaac agcggccctc aggggtccct   180
gaccgattct ctggctccaa atctggcacc tccgcctccc tggccgtgag tgggctccag   240
tctgaggatg aggctgatta ttactgtgca tcatgggatg acaacttgag tggttgggtg   300
ttcggcggag ggaccaagct gaccgtccta                                    330
```

<210> SEQ ID NO 53
<211> LENGTH: 120
<212> TYPE: PRT
<213> ORGANISM: Homo sapiens

<400> SEQUENCE: 53

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ala Tyr
                20                  25                  30
Ala Phe Thr Trp Val Arg Gln Ala Pro Gly Gln Gly Leu Glu Trp Met
            35                  40                  45
Gly Gly Ile Thr Gly Met Phe Gly Thr Ala Asn Tyr Ala Gln Lys Phe
        50                  55                  60
Gln Gly Arg Val Thr Ile Thr Ala Asp Glu Leu Thr Ser Thr Ala Tyr
65                  70                  75                  80
Met Glu Leu Ser Ser Leu Thr Ser Glu Asp Thr Ala Leu Tyr Tyr Cys
                85                  90                  95
Ala Arg Gly Leu Tyr Tyr Tyr Glu Ser Ser Leu Asp Tyr Trp Gly Gln
                100                 105                 110
Gly Thr Leu Val Thr Val Ser Ser
            115                 120
```

<210> SEQ ID NO 54
<211> LENGTH: 361
<212> TYPE: DNA
<213> ORGANISM: Homo sapiens

<400> SEQUENCE: 54

```
caggtgcagc tggtgcagtc tggggctgag gtgaagaagc ctgggtcctc ggtgaaggtc    60
tcctgcaagg cttctggagg caccttcagc gcttatgctt tcacctgggt gcggcaggcc   120
cctggacaag ggcttgagtg gatgggaggc atcaccggaa tgtttggcac agcaaactac   180
gcacagaagt tccagggcag agtcacgatt accgcggacg aactcacgag cacagcctac   240
atggagttga gctccctgac atctgaagac acggcccttt attattgtgc gagaggattg   300
tattactatg agagtagtct tgactattgg ggccagggaa ccctggtcac cgtctcctca   360
g                                                                  361
```

<210> SEQ ID NO 55
<211> LENGTH: 110
<212> TYPE: PRT
<213> ORGANISM: Homo sapiens

<400> SEQUENCE: 55

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Glu Val Thr Lys Arg Pro Ser Gly Val Pro Asp Arg Phe
    50                  55                  60

Ser Ala Ser Lys Ser Gly Asn Thr Ala Ser Leu Thr Val Ser Gly Leu
65              70                  75                  80

Gln Ala Glu Asp Glu Ala Asp Tyr Phe Cys Cys Ser Tyr Ala Gly His
                85                  90                  95

Ser Ala Tyr Val Phe Gly Thr Gly Thr Lys Val Thr Val Leu
            100                 105                 110

<210> SEQ ID NO 56
<211> LENGTH: 361
<212> TYPE: DNA
<213> ORGANISM: Homo sapiens

<400> SEQUENCE: 56
caggtgcagc tggtgcagtc tggggctgag gtgaagaagc ctgggtcctc ggtgaaggtc      60
tcctgcaggg cttctggagg caccttcagc gcttatgctt tcacctgggt gcggcaggcc    120
cctggacaag ggcttgagtg gatgggaggc atcaccggaa tgtttggcac agcaaactac    180
gcacagaagt tccagggcag agtcacgatt accgcggacg aactcacgag cacagcctac    240
atggagttga gctccctgac atctgaagac acggcccttt attattgtgc gagaggattg    300
tattactatg agagtagtct tgactattgg ggccagggaa ccctggtcac cgtctcctca    360
g                                                                    361

<210> SEQ ID NO 57
<211> LENGTH: 108
<212> TYPE: PRT
<213> ORGANISM: Homo sapiens

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Ser Lys
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Ser Cys Gln Gln Tyr Asp Gly Val Pro
                85                  90                  95

Arg Thr Phe Gly Gln Gly Thr Lys Val Glu Ile Lys
            100                 105

<210> SEQ ID NO 58
<211> LENGTH: 330
<212> TYPE: DNA
<213> ORGANISM: Homo sapiens

<400> SEQUENCE: 58

```
cagtctgtgc tgactcagcc accctccgcg tccgggtctc ctggacagtc agtcaccatc    60
tcctgcactg gaaccagcag tgacgttggt ggttataact ctgtctcctg gtaccaacag   120
cacccaggca aagcccccaa actcatgatt tatgaggtca ctaagcggcc ctcaggggtc   180
cctgatcgct tctctgcctc caagtctggc aacacggcct ccctgaccgt ctctgggctc   240
caggctgagg atgaggctga ttatttctgc tgctcatatg caggccacag tgcttatgtc   300
ttcggaactg ggaccaaggt caccgtcctg                                    330
```

<210> SEQ ID NO 59
<211> LENGTH: 124
<212> TYPE: PRT
<213> ORGANISM: Homo sapiens

<400> SEQUENCE: 59

```
Gln Val Gln Leu Val Gln Ser Gly Ala Glu Val Lys Lys Pro Gly Ser
 1               5                  10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120
```

<210> SEQ ID NO 60
<211> LENGTH: 324
<212> TYPE: DNA
<213> ORGANISM: Homo sapiens

<400> SEQUENCE: 60

```
gaaattgtgc tgactcagtc tccaggcacc ctgtctttgt ctccagggga agagccacc    60
ctctcctgca gggccagtca gagtcttagc agcaagtact tagcctggta tcagcagaaa   120
cctggccagg ctcccaggct cctcatctat ggtgcatcca gcagggccac tggcatccca   180
gacaggttca gtggcagtgg gtctgggaca gacttcaccc tcaccatcag tagactggag   240
cctgaagatt ttgcagtgta ttcctgtcag cagtatgatg gcgtacctcg gacgttcggc   300
caagggacca cggtggaaat caaa                                          324
```

<210> SEQ ID NO 61
<211> LENGTH: 110
<212> TYPE: PRT
<213> ORGANISM: Homo sapiens

<400> SEQUENCE: 61

```
Gln Pro Gly Leu Thr Gln Pro Pro Ser Val Ser Lys Gly Leu Arg Gln
 1               5                  10                  15

Thr Ala Thr Leu Thr Cys Thr Gly Asn Ser Asn Asn Val Gly Asn Gln
            20                  25                  30
```

Gly Ala Ala Trp Leu Gln Gln His Gln Gly His Pro Pro Lys Leu Leu
            35                  40                  45

Ser Tyr Arg Asn Asn Asp Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Thr Trp Asp Ser Ser Leu
                85                  90                  95

Ser Ala Val Val Phe Gly Gly Gly Thr Lys Leu Thr Val Leu
            100                 105                 110

<210> SEQ ID NO 62
<211> LENGTH: 372
<212> TYPE: DNA
<213> ORGANISM: Homo sapiens

<400> SEQUENCE: 62
caggtgcagc tggtgcagtc aggggctgag gtgaagaagc ctgggtcctc ggtgaaggtc      60
tcctgcacgt cctctgaagt caccttcagt agttttgcta tcagctgggt gcgacaggcc    120
cctggacaag gcttgagtg gctgggaggg atcagcccta tgtttggaac acctaattac    180
gcgcagaagt tccaaggcag agtcaccatt accgcggacc agtccacgag acagcctac    240 atggacctga ggagcctgag atctgaggac acggccgtgt attattgtgc gagatctcct    300
tcttacattt gttctggtgg aacctgcgtc tttgaccatt ggggccaggg aaccctggtc    360
accgtctcct ca                                                        372

<210> SEQ ID NO 63
<211> LENGTH: 107
<212> TYPE: PRT
<213> ORGANISM: Homo sapiens

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asp Ser Ser Pro Tyr
                85                  90                  95

Thr Phe Gly Gln Gly Thr Lys Val Glu Ile Lys
            100                 105

<210> SEQ ID NO 64
<211> LENGTH: 372
<212> TYPE: DNA
<213> ORGANISM: Homo sapiens

<400> SEQUENCE: 64
caggtacagc tgcagcagtc aggggctgag gtgaagaagc ctgggtcctc ggtgaaggtc      60
tcctgcacgt cctctgaagt caccttcagt agttttgcta tcagctgggt gcgacaggcc    120

```
cctggacaag ggcttgagtg gctgggaggg atcagccta tgtttggaac acctaattac    180
gcgcagaagt tccaaggcag agtcaccatt accgcggacc agtccacgag dacagcctac    240
atggacctga ggagcctgag atctgaggac acggccgtgt attattgtgc gagatctcct    300
tcttacattt gttctggtgg aacctgcgtc tttgaccatt ggggccaggg aaccctggtc    360
accgtctcct ca                                                        372
```

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 65

Ser Tyr Ala Phe Ser
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 66

Gly Ile Ile Pro Met Phe Gly Thr Pro Asn Tyr Ala Gln Lys Phe Gln
1               5                   10                  15

Gly

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 67

Ser Ser Gly Tyr Tyr Tyr Gly Gly Gly Phe Asp Val
1               5                   10

<210> SEQ ID NO 68
<211> LENGTH: 5
<212> TYPE: PRT
<213> ORGANISM: Homo sapiens

<400> SEQUENCE: 68

Thr Asn Ala Phe Ser
1               5

<210> SEQ ID NO 69
<211> LENGTH: 17
<212> TYPE: PRT
<213> ORGANISM: Homo sapiens

<400> SEQUENCE: 69

Gly Val Ile Pro Leu Phe Arg Thr Ala Ser Tyr Ala Gln Asn Val Gln
1               5                   10                  15

Gly

```
<210> SEQ ID NO 70
<211> LENGTH: 13
<212> TYPE: PRT
<213> ORGANISM: Homo sapiens

<400> SEQUENCE: 70

Ser Ser Gly Tyr His Phe Gly Arg Ser His Phe Asp Ser
1               5                   10

<210> SEQ ID NO 71
<211> LENGTH: 5
<212> TYPE: PRT
<213> ORGANISM: Homo sapiens

<400> SEQUENCE: 71

Ala Tyr Ala Phe Thr
1               5

<210> SEQ ID NO 72
<211> LENGTH: 17
<212> TYPE: PRT
<213> ORGANISM: Homo sapiens

<400> SEQUENCE: 72

Gly Ile Ile Gly Met Phe Gly Thr Ala Asn Tyr Ala Gln Lys Phe Gln
1               5                   10                  15

Gly

<210> SEQ ID NO 73
<211> LENGTH: 11
<212> TYPE: PRT
<213> ORGANISM: Homo sapiens

<400> SEQUENCE: 73

Gly Leu Tyr Tyr Tyr Glu Ser Ser Leu Asp Tyr
1               5                   10

<210> SEQ ID NO 74
<211> LENGTH: 5
<212> TYPE: PRT
<213> ORGANISM: Homo sapiens

<400> SEQUENCE: 74

Ser Phe Ala Ile Ser
1               5

<210> SEQ ID NO 75
<211> LENGTH: 17
<212> TYPE: PRT
<213> ORGANISM: Homo sapiens

<400> SEQUENCE: 75

Gly Ile Ser Pro Met Phe Gly Thr Pro Asn Tyr Ala Gln Lys Phe Gln
1               5                   10                  15

Gly

<210> SEQ ID NO 76
<211> LENGTH: 15
<212> TYPE: PRT
<213> ORGANISM: Homo sapiens

<400> SEQUENCE: 76

Ser Pro Ser Tyr Ile Cys Ser Gly Gly Thr Cys Val Phe Asp His
1               5                   10                  15
```

```
<210> SEQ ID NO 77
<211> LENGTH: 5
<212> TYPE: PRT
<213> ORGANISM: Homo sapiens

<400> SEQUENCE: 77

Ser Tyr Ala Ile Ser
1               5

<210> SEQ ID NO 78
<211> LENGTH: 17
<212> TYPE: PRT
<213> ORGANISM: Homo sapiens

<400> SEQUENCE: 78

Gly Ile Ile Gly Val Phe Gly Val Pro Lys Tyr Ala Gln Lys Phe Gln
1               5                   10                  15

Gly

<210> SEQ ID NO 79
<211> LENGTH: 13
<212> TYPE: PRT
<213> ORGANISM: Homo sapiens

<400> SEQUENCE: 79

Glu Pro Gly Tyr Tyr Val Gly Lys Asn Gly Phe Asp Val
1               5                   10

<210> SEQ ID NO 80
<211> LENGTH: 5
<212> TYPE: PRT
<213> ORGANISM: Homo sapiens

<400> SEQUENCE: 80

Gly Tyr Tyr Ile His
1               5

<210> SEQ ID NO 81
<211> LENGTH: 17
<212> TYPE: PRT
<213> ORGANISM: Homo sapiens

<400> SEQUENCE: 81

Trp Ile Asn Pro Met Thr Gly Gly Thr Asn Tyr Ala Gln Lys Phe Gln
1               5                   10                  15

Val

<210> SEQ ID NO 82
<211> LENGTH: 17
<212> TYPE: PRT
<213> ORGANISM: Homo sapiens

<400> SEQUENCE: 82

Gly Ala Ser Val Leu Arg Tyr Phe Asp Trp Gln Pro Glu Ala Leu Asp
1               5                   10                  15

Ile

<210> SEQ ID NO 83
<211> LENGTH: 5
<212> TYPE: PRT
<213> ORGANISM: Homo sapiens
```

```
<400> SEQUENCE: 83

Met Thr Ala Phe Thr
1               5

<210> SEQ ID NO 84
<211> LENGTH: 17
<212> TYPE: PRT
<213> ORGANISM: Homo sapiens

<400> SEQUENCE: 84

Gly Ile Ser Pro Ile Phe Arg Thr Pro Lys Tyr Ala Gln Lys Phe Gln
1               5                   10                  15

Gly

<210> SEQ ID NO 85
<211> LENGTH: 14
<212> TYPE: PRT
<213> ORGANISM: Homo sapiens

<400> SEQUENCE: 85

Thr Leu Ser Ser Tyr Gln Pro Asn Asn Asp Ala Phe Ala Ile
1               5                   10

<210> SEQ ID NO 86
<211> LENGTH: 5
<212> TYPE: PRT
<213> ORGANISM: Homo sapiens

<400> SEQUENCE: 86

Asp Asn Ala Ile Ser
1               5

<210> SEQ ID NO 87
<211> LENGTH: 17
<212> TYPE: PRT
<213> ORGANISM: Homo sapiens

<400> SEQUENCE: 87

Gly Ile Ile Pro Ile Phe Gly Lys Pro Asn Tyr Ala Gln Lys Phe Gln
1               5                   10                  15

Gly

<210> SEQ ID NO 88
<211> LENGTH: 14
<212> TYPE: PRT
<213> ORGANISM: Homo sapiens

<400> SEQUENCE: 88

Asp Ser Asp Ala Tyr Tyr Tyr Gly Ser Gly Gly Met Asp Val
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 89

Thr Gly Ser Ser Ser Asn Ile Gly Asn Tyr Val Ala
1               5                   10
```

```
<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 90

Ser Asn Ser Asp Arg Pro Ser
1               5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 91

Gln Ser Tyr Asp Ser Leu Ser Ala Tyr Val
1               5                   10

<210> SEQ ID NO 92
<211> LENGTH: 13
<212> TYPE: PRT
<213> ORGANISM: Homo sapiens

<400> SEQUENCE: 92

Thr Gly Ser Ser Ser Asn Ile Ala Ala Asn Tyr Val Gln
1               5                   10

<210> SEQ ID NO 93
<211> LENGTH: 7
<212> TYPE: PRT
<213> ORGANISM: Homo sapiens

<400> SEQUENCE: 93

Glu Asp Asp Arg Arg Pro Ser
1               5

<210> SEQ ID NO 94
<211> LENGTH: 10
<212> TYPE: PRT
<213> ORGANISM: Homo sapiens

<400> SEQUENCE: 94

Gln Ser Tyr Asp Thr Asn Asn His Ala Val
1               5                   10

<210> SEQ ID NO 95
<211> LENGTH: 14
<212> TYPE: PRT
<213> ORGANISM: Homo sapiens

<400> SEQUENCE: 95

Thr Gly Thr Ser Ser Asp Val Gly Gly Tyr Asn Ser Val Ser
1               5                   10

<210> SEQ ID NO 96
<211> LENGTH: 7
<212> TYPE: PRT
<213> ORGANISM: Homo sapiens

<400> SEQUENCE: 96
```

```
Glu Val Thr Lys Arg Pro Ser
1               5
```

<210> SEQ ID NO 97
<211> LENGTH: 10
<212> TYPE: PRT
<213> ORGANISM: Homo sapiens

<400> SEQUENCE: 97

```
Cys Ser Tyr Ala Gly His Ser Ala Tyr Val
1               5                   10
```

<210> SEQ ID NO 98
<211> LENGTH: 13
<212> TYPE: PRT
<213> ORGANISM: Homo sapiens

<400> SEQUENCE: 98

```
Thr Gly Asn Ser Asn Asn Val Gly Asn Gln Gly Ala Ala
1               5                   10
```

<210> SEQ ID NO 99
<211> LENGTH: 7
<212> TYPE: PRT
<213> ORGANISM: Homo sapiens

<400> SEQUENCE: 99

```
Arg Asn Asn Asp Arg Pro Ser
1               5
```

<210> SEQ ID NO 100
<211> LENGTH: 11
<212> TYPE: PRT
<213> ORGANISM: Homo sapiens

<400> SEQUENCE: 100

```
Ser Thr Trp Asp Ser Ser Leu Ser Ala Val Val
1               5                   10
```

<210> SEQ ID NO 101
<211> LENGTH: 13
<212> TYPE: PRT
<213> ORGANISM: Homo sapiens

<400> SEQUENCE: 101

```
Thr Gly Asp Ser Asn Asn Val Gly His Gln Gly Thr Ala
1               5                   10
```

<210> SEQ ID NO 102
<211> LENGTH: 7
<212> TYPE: PRT
<213> ORGANISM: Homo sapiens

<400> SEQUENCE: 102

```
Arg Asn Gly Asn Arg Pro Ser
1               5
```

<210> SEQ ID NO 103
<211> LENGTH: 11
<212> TYPE: PRT
<213> ORGANISM: Homo sapiens

<400> SEQUENCE: 103

```
Ser Val Trp Asp Ser Ser Leu Ser Ala Trp Val
1               5                   10
```

<210> SEQ ID NO 104
<211> LENGTH: 11
<212> TYPE: PRT
<213> ORGANISM: Homo sapiens

<400> SEQUENCE: 104

Gly Gly Asn Asn Ile Gly Gly Tyr Ser Val His
1               5                   10

<210> SEQ ID NO 105
<211> LENGTH: 7
<212> TYPE: PRT
<213> ORGANISM: Homo sapiens

<400> SEQUENCE: 105

Asp Asp Lys Asp Arg Pro Ser
1               5

<210> SEQ ID NO 106
<211> LENGTH: 11
<212> TYPE: PRT
<213> ORGANISM: Homo sapiens

<400> SEQUENCE: 106

Gln Val Trp Asp Ser Gly Asn Asp Arg Pro Leu
1               5                   10

<210> SEQ ID NO 107
<211> LENGTH: 11
<212> TYPE: PRT
<213> ORGANISM: Homo sapiens

<400> SEQUENCE: 107

Arg Ala Ser Gln Ser Val Ser Ser Tyr Leu Ala
1               5                   10

<210> SEQ ID NO 108
<211> LENGTH: 7
<212> TYPE: PRT
<213> ORGANISM: Homo sapiens

<400> SEQUENCE: 108

Asp Ala Ser Asn Arg Ala Thr
1               5

<210> SEQ ID NO 109
<211> LENGTH: 9
<212> TYPE: PRT
<213> ORGANISM: Homo sapiens

<400> SEQUENCE: 109

Gln Gln Tyr Gly Ser Ser Pro Gln Val
1               5

<210> SEQ ID NO 110
<211> LENGTH: 12
<212> TYPE: PRT
<213> ORGANISM: Homo sapiens

<400> SEQUENCE: 110

Arg Ala Ser Gln Ser Leu Ser Ser Lys Tyr Leu Ala
1               5                   10

```
<210> SEQ ID NO 111
<211> LENGTH: 7
<212> TYPE: PRT
<213> ORGANISM: Homo sapiens

<400> SEQUENCE: 111

Gly Ala Ser Ser Arg Ala Thr
1               5

<210> SEQ ID NO 112
<211> LENGTH: 9
<212> TYPE: PRT
<213> ORGANISM: Homo sapiens

<400> SEQUENCE: 112

Gln Gln Tyr Asp Gly Val Pro Arg Thr
1               5

<210> SEQ ID NO 113
<211> LENGTH: 12
<212> TYPE: PRT
<213> ORGANISM: Homo sapiens

<400> SEQUENCE: 113

Thr Gly Ser Ser Ser Asn Ile Gly Asn Tyr Val Ala
1               5                   10

<210> SEQ ID NO 114
<211> LENGTH: 7
<212> TYPE: PRT
<213> ORGANISM: Homo sapiens

<400> SEQUENCE: 114

Ser Asn Asn Gln Arg Pro Ser
1               5

<210> SEQ ID NO 115
<211> LENGTH: 11
<212> TYPE: PRT
<213> ORGANISM: Homo sapiens

<400> SEQUENCE: 115

Gln Ser Tyr Asp Ser Arg Leu Ser Ala Ser Leu
1               5                   10

<210> SEQ ID NO 116
<211> LENGTH: 13
<212> TYPE: PRT
<213> ORGANISM: Homo sapiens

<400> SEQUENCE: 116

Ser Gly Ser Ser Ser Asn Ile Gly Ser Asn Thr Val Asn
1               5                   10

<210> SEQ ID NO 117
<211> LENGTH: 7
<212> TYPE: PRT
<213> ORGANISM: Homo sapiens

<400> SEQUENCE: 117

Ala Ala Ser Ser Leu Gln Arg
1               5

<210> SEQ ID NO 118
<211> LENGTH: 9
```

```
<212> TYPE: PRT
<213> ORGANISM: Homo sapiens

<400> SEQUENCE: 118

Gln Gln Tyr Asp Ser Ser Pro Tyr Thr
1               5

<210> SEQ ID NO 119
<211> LENGTH: 11
<212> TYPE: PRT
<213> ORGANISM: Homo sapiens

<400> SEQUENCE: 119

Arg Ala Ser Gln Ser Ile Ser Ser Tyr Leu Asn
1               5                   10

<210> SEQ ID NO 120
<211> LENGTH: 7
<212> TYPE: PRT
<213> ORGANISM: Homo sapiens

<400> SEQUENCE: 120

Ser Asn Glu Gln Arg Pro Ser
1               5

<210> SEQ ID NO 121
<211> LENGTH: 11
<212> TYPE: PRT
<213> ORGANISM: Homo sapiens

<400> SEQUENCE: 121

Ala Ser Trp Asp Asp Asn Leu Ser Gly Trp Val
1               5                   10

<210> SEQ ID NO 122
<211> LENGTH: 12
<212> TYPE: PRT
<213> ORGANISM: Homo sapiens

<400> SEQUENCE: 122

Thr Leu Ser Ser Gly His Ser Asn Tyr Ile Ile Ala
1               5                   10

<210> SEQ ID NO 123
<211> LENGTH: 11
<212> TYPE: PRT
<213> ORGANISM: Homo sapiens

<400> SEQUENCE: 123

Val Asn Ser Asp Gly Ser His Thr Lys Gly Asp
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      chemically synthesized sequence

<400> SEQUENCE: 124

Glu Thr Trp Asp Thr Lys Ile His Val
1               5

<210> SEQ ID NO 125
```

```
<211> LENGTH: 202
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(100)
<223> OTHER INFORMATION: Any amino acid or absent
<220> FEATURE:
<221> NAME/KEY: MOD_RES
<222> LOCATION: (101)..(101)
<223> OTHER INFORMATION: Ser, Thr, Phe, His or Tyr
<220> FEATURE:
<221> NAME/KEY: MOD_RES
<222> LOCATION: (102)..(102)
<223> OTHER INFORMATION: His, Tyr, Met, Leu or Gln
<220> FEATURE:
<221> NAME/KEY: MOD_RES
<222> LOCATION: (103)..(202)
<223> OTHER INFORMATION: Any amino acid or absent
<220> FEAT

```
<220> FEATURE:
<221> NAME/KEY: MOD_RES
<222> LOCATION: (101)..(101)
<223> OTHER INFORMATION: His, Gln, Tyr, Ser, Asp, Asn or Thr
<220> FEATURE:
<221> NAME/KEY: MOD_RES
<222> LOCATION: (102)..(102)
<223> OTHER INFORMATION: Gln, Glu, Lys, Ile, Val, Met, Arg or Thr
<220> FEATURE:
<221> NAME/KEY: MOD_RES
<222> LOCATION: (103)..(202)
<223> OTHER INFORMATION: Any amino acid or absent
<220> FEATURE:
<223> OTHER INFORMATION: See specification as filed for detailed
      description of substitutions and preferred embodiments

<400> SEQUENCE: 126

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa
    195                 200

<210> SEQ ID NO 127
<211> LENGTH: 204
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(100)
<223> OTHER INFORMATION: Any amino acid or absent
<220> FEATURE:
<221> NAME/KEY: MOD_RES
<222> LOCATION: (101)..(101)
<223> OTHER INFORMATION: Ile, Val, Met or Leu
<220> FEATURE:
<221> NAME/KEY: MOD_RES
<222> LOCATION: (102)..(102)
<223> OTHER INFORMATION: Asp, Asn, His, Tyr, Asp, Ala, Ser or Glu
<220> FEATURE:
<221> NAME/KEY: MOD_RES
```

<222> LOCATION: (103)..(103)
<223> OTHER INFORMATION: Gly or Ala
<220> FEATURE:
<221> NAME/KEY: MOD_RES
<222> LOCATION: (104)..(104)
<223> OTHER INFORMATION: Trp, Arg or Gly
<220> FEATURE:
<221> NAME/KEY: MOD_RES
<222> LOCATION: (105)..(204)
<223> OTHER INFORMATION: Any amino acid or absent
<220> FEATURE:
<223> OTHER INFORMATION: See specification as filed for detailed
      description of substitutions and preferred embodiments

<400> SEQUENCE: 127

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa
        195                 200

<210> SEQ ID NO 128
<211> LENGTH: 219
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(100)
<223> OTHER INFORMATION: Any amino acid or absent
<220> FEATURE:
<221> NAME/KEY: MOD_RES
<222> LOCATION: (101)..(101)
<223> OTHER INFORMATION: Lys, Gln, Arg, Asn, Leu, Gly, Phe, His or Tyr
<220> FEATURE:
<221> NAME/KEY: MOD_RES
<222> LOCATION: (102)..(103)
<223> OTHER INFORMATION: Any amino acid
<220> FEATURE:
<221> NAME/KEY: MOD_RES
<222> LOCATION: (104)..(104)
<223> OTHER INFORMATION: Ser or Thr

```
<220> FEATURE:
<221> NAME/KEY: MOD_RES
<222> LOCATION: (105)..(105)
<223> OTHER INFORMATION: Gln or Pro
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (108)..(108)
<223> OTHER INFORMATION: Phe, Val, Ile, Met, Leu or Thr
<220> FEATURE:
<221> NAME/KEY: MOD_RES
<222> LOCATION: (109)..(111)
<223> OTHER INFORMATION: Any amino acid
<220> FEATURE:
<221> NAME/KEY: MOD_RES
<222> LOCATION: (112)..(112)
<223> OTHER INFORMATION: Ile, Thr, Ser, Asn, Gln, Asp or Ala
<220> FEATURE:
<221> NAME/KEY: MOD_RES
<222> LOCATION: (113)..(114)
<223> OTHER INFORMATION: Any amino acid
<220> FEATURE:
<221> NAME/KEY: MOD_RES
<222> LOCATION: (115)..(115)
<223> OTHER INFORMATION: Ile, Val, Met or Leu
<220> FEATURE:
<221> NAME/KEY: MOD_RES
<222> LOCATION: (116)..(116)
<223> OTHER INFORMATION: Asn, Ser, Thr or Asp
<220> FEATURE:
<221> NAME/KEY: MOD_RES
<222> LOCATION: (117)..(118)
<223> OTHER INFORMATION: Any amino acid
<220> FEATURE:
<221> NAME/KEY: MOD_RES
<222> LOCATION: (119)..(119)
<223> OTHER INFORMATION: Ile, Phe, Val, Ala or Thr
<220> FEATURE:
<221> NAME/KEY: MOD_RES
<222> LOCATION: (120)..(219)
<223> OTHER INFORMATION: Any amino acid or absent
<220> FEATURE:
<223> OTHER INFORMATION: See specification as filed for detailed
     description of substitutions and preferred embodiments

<400> SEQUENCE: 128

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160
```

```
Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa
    210                 215

<210> SEQ ID NO 129
<211> LENGTH: 219
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(100)
<223> OTHER INFORMATION: Any amino acid or absent
<220> FEATURE:
<221> NAME/KEY: MOD_RES
<222> LOCATION: (101)..(101)
<223> OTHER INFORMATION: Lys, Gln, Arg, Asn, Leu, Gly, Phe, His or Tyr
<220> FEATURE:
<221> NAME/KEY: MOD_RES
<222> LOCATION: (102)..(103)
<223> OTHER INFORMATION: Any amino acid
<220> FEATURE:
<221> NAME/KEY: MOD_RES
<222> LOCATION: (104)..(104)
<223> OTHER INFORMATION: Ser or Thr
<220> FEATURE:
<221> NAME/KEY: MOD_RES
<222> LOCATION: (105)..(105)
<223> OTHER INFORMATION: Gln or Pro
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (108)..(108)
<223> OTHER INFORMATION: Phe, Val, Ile, Met, Leu or Thr
<220> FEATURE:
<221> NAME/KEY: MOD_RES
<222> LOCATION: (109)..(111)
<223> OTHER INFORMATION: Any amino acid
<220> FEATURE:
<221> NAME/KEY: MOD_RES
<222> LOCATION: (112)..(112)
<223> OTHER INFORMATION: Ile, Thr, Ser, Asn, Gln, Asp or Ala
<220> FEATURE:
<221> NAME/KEY: MOD_RES
<222> LOCATION: (113)..(114)
<223> OTHER INFORMATION: Any amino acid
<220> FEATURE:
<221> NAME/KEY: MOD_RES
<222> LOCATION: (115)..(115)
<223> OTHER INFORMATION: Ile, Val, Met or Leu
<220> FEATURE:
<221> NAME/KEY: MOD_RES
<222> LOCATION: (116)..(116)
<223> OTHER INFORMATION: Asn, Ser, Thr or Asp
<220> FEATURE:
<221> NAME/KEY: MOD_RES
<222> LOCATION: (117)..(118)
<223> OTHER INFORMATION: Any amino acid or absent
<220> FEATURE:
<221> NAME/KEY: MISC_FEATURE
<222> LOCATION: (117)..(118)
<223> OTHER INFORMATION: This region may be absent in its entirety
<220> FEATURE:
<221> NAME/KEY: MOD_RES
```

<222> LOCATION: (119)..(119)
<223> OTHER INFORMATION: Ile, Phe, Val, Ala, Thr or absent
<220> FEATURE:
<221> NAME/KEY: MISC_FEATURE
<222> LOCATION: (119)..(119)
<223> OTHER INFORMATION: This region may be absent in its entirety
<220> FEATURE:
<221> NAME/KEY: MOD_RES
<222> LOCATION: (120)..(219)
<223> OTHER INFORMATION: Any amino acid or absent
<220> FEATURE:
<223> OTHER INFORMATION: See specification as filed for detailed
      description of substitutions and preferred embodiments

<400> SEQUENCE: 129

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa
210                 215

<210> SEQ ID NO 130
<211> LENGTH: 22
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(10)
<223> OTHER INFORMATION: Any amino acid
<220> FEATURE:
<221> NAME/KEY: MISC_FEATURE
<222> LOCATION: (1)..(10)
<223> OTHER INFORMATION: In some embodiments, this region may be
      absent in its entirety
<220> FEATURE:
<221> NAME/KEY: MOD_RES
<222> LOCATION: (11)..(11)
<223> OTHER INFORMATION: Ser, Thr, Phe, His or Tyr

```
<220> FEATURE:
<221> NAME/KEY: MOD_RES
<222> LOCATION: (12)..(12)
<223> OTHER INFORMATION: His, Tyr, Met, Leu or Gln
<220> FEATURE:
<221> NAME/KEY: MOD_RES
<222> LOCATION: (13)..(22)
<223> OTHER INFORMATION: Any amino acid
<220> FEATURE:
<221> NAME/KEY: MISC_FEATURE
<222> LOCATION: (13)..(22)
<223> OTHER INFORMATION: In some embodiments, this region may be
      absent in its entirety
<220> FEATURE:
<223> OTHER INFORMATION: See specification as filed for detailed
      description of substitutions and preferred embodiments

<400> SEQUENCE: 130

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 131
<211> LENGTH: 22
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(10)
<223> OTHER INFORMATION: Any amino acid
<220> FEATURE:
<221> NAME/KEY: MISC_FEATURE
<222> LOCATION: (1)..(10)
<223> OTHER INFORMATION: In some embodiments, this region may be
      absent in its entirety
<220> FEATURE:
<221> NAME/KEY: MOD_RES
<222> LOCATION: (11)..(11)
<223> OTHER INFORMATION: His, Gln, Tyr, Ser, Asp, Asn or Thr
<220> FEATURE:
<221> NAME/KEY: MOD_RES
<222> LOCATION: (12)..(12)
<223> OTHER INFORMATION: Gln, Glu, Lys, Ile, Val, Met, Arg or Thr
<220> FEATURE:
<221> NAME/KEY: MOD_RES
<222> LOCATION: (13)..(22)
<223> OTHER INFORMATION: Any amino acid
<220> FEATURE:
<221> NAME/KEY: MISC_FEATURE
<222> LOCATION: (13)..(22)
<223> OTHER INFORMATION: In some embodiments, this region may be
      absent in its entirety
<220> FEATURE:
<223> OTHER INFORMATION: See specification as filed for detailed
      description of substitutions and preferred embodiments

<400> SEQUENCE: 131

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 132
<211> LENGTH: 24
<212> TYPE: PRT
<213> ORGANISM: Artificial Sequence
<220> FEATURE:
<223> OTHER INFORMATION: Description of Artificial Sequence: Synthetic
      chemically synthesized sequence
```

```
<220> FEATURE:
<221> NAME/KEY: MOD_RES
<222> LOCATION: (1)..(10)
<223> OTHER INFORMATION: Any amino acid or absent
<220> FEATURE:
<221> NAME/KEY: MOD_RES
<222> LOCATION: (11)..(11)
<223> OTHER INFORMATION: Ile, Val, Met or Leu
<220> FEATURE:
<221> NAME/KEY: MOD_RES
<222> LOCATION: (12)..(12)
<223> OTHER INFORMATION: Asp, Asn, His, Tyr, Asp, Ala, Ser or Glu
<220> FEATURE:
<221> NAME/KEY: MOD_RES
<222> LOCATION: (13)..(13)
<223> OTHER INFORMATION: Gly or Ala
<220> FEATURE:
<221> NAME/KEY: MOD_RES
<222> LOCATION: (14)..(14)
<223> OTHER INFORMATION: Trp, Arg or Gly
<220> FEATURE:
<221> NAME/KEY: MOD_RES
<222> LOCATION: (15)..(24)
<223> OTHER INFORMATION: Any amino acid or absent
<220> FEATURE:
<223> OTHER INFORMATION: See specification as filed for detailed
      description of substitutions and preferred embodiments

<400> SEQUENCE: 132

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 133
<211> LENGTH: 39
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(10)
<223> OTHER INFORMATION: Any amino acid or absent
<220> FEATURE:
<221> NAME/KEY: MOD_RES
<222> LOCATION: (11)..(11)
<223> OTHER INFORMATION: Lys, Gln, Arg, Asn, Leu, Gly, Phe, His or Tyr
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Gln or Pro
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (18)..(18)
<223> OTHER INFORMATION: Phe, Val, Ile, Met, Leu or Thr
<220> FEATURE:
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (22)..(22)
```

```
<223> OTHER INFORMATION: Ile, Thr, Ser, Asn, Gln, Asp or Ala
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (25)..(25)
<223> OTHER INFORMATION: Ile, Val, Met or Leu
<220> FEATURE:
<221> NAME/KEY: MOD_RES
<222> LOCATION: (26)..(26)
<223> OTHER INFORMATION: Asn, Ser, Thr or Asp
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (29)..(29)
<223> OTHER INFORMATION: Ile, Phe, Val, Ala or Thr
<220> FEATURE:
<221> NAME/KEY: MOD_RES
<222> LOCATION: (30)..(39)
<223> OTHER INFORMATION: Any amino acid or absent
<220> FEATURE:
<223> OTHER INFORMATION: See specification as filed for detailed
      description of substitutions and preferred embodiments

<400> SEQUENCE: 133

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 134
<211> LENGTH: 39
<212> TYPE: PRT
<213> ORGANISM: Artificial Sequence
<220> FEATURE:
<223> OTHER INFORMATION: Description of Artificial Sequence: Synthetic
      chemically synthesized sequence
<220> FEATURE:
<221> NAME/KEY: MOD_RES
<222> LOCATION: (1)..(10)
<223> OTHER INFORMATION: Any amino acid or absent
<220> FEATURE:
<221> NAME/KEY: MOD_RES
<222> LOCATION: (11)..(11)
<223> OTHER INFORMATION: Lys, Gln, Arg, Asn, Leu, Gly, Phe, His or Tyr
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Gln or Pro
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (18)..(18)
<223> OTHER INFORMATION: Phe, Val, Ile, Met, Leu or Thr
<220> FEATURE:
<221> NAME/KEY: MOD_RES
<222> LOCATION: (19)..(21)
```

```
<223> OTHER INFORMATION: Any amino acid
<220> FEATURE:
<221> NAME/KEY: MOD_RES
<222> LOCATION: (22)..(22)
<223> OTHER INFORMATION: Ile, Thr, Ser, Asn, Gln, Asp or Ala
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (25)..(25)
<223> OTHER INFORMATION: Ile, Val, Met or Leu
<220> FEATURE:
<221> NAME/KEY: MOD_RES
<222> LOCATION: (26)..(26)
<223> OTHER INFORMATION: Asn, Ser, Thr or Asp
<220> FEATURE:
<221> NAME/KEY: MOD_RES
<222> LOCATION: (27)..(28)
<223> OTHER INFORMATION: Any amino acid or absent
<220> FEATURE:
<221> NAME/KEY: MISC_FEATURE
<222> LOCATION: (27)..(28)
<223> OTHER INFORMATION: This region may be absent in its entirety
<220> FEATURE:
<221> NAME/KEY: MOD_RES
<222> LOCATION: (29)..(29)
<223> OTHER INFORMATION: Ile, Phe, Val, Ala, Thr or absent
<220> FEATURE:
<221> NAME/KEY: MISC_FEATURE
<222> LOCATION: (27)..(28)
<223> OTHER INFORMATION: This region may be absent in its entirety
<220> FEATURE:
<221> NAME/KEY: MOD_RES
<222> LOCATION: (30)..(39)
<223> OTHER INFORMATION: Any amino acid or absent
<220> FEATURE:
<223> OTHER INFORMATION: See specification as filed for detailed
      description of substitutions and preferred embodiments

<400> SEQUENCE: 134

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Thr Glu Thr Ser Gln Val Ala Pro Ala
1               5                   10

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 136

His His His His His His
1               5
```

```
<210> SEQ ID NO 137
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Any amino acid
<220> FEATURE:
<221> NAME/KEY: MISC_FEATURE
<222> LOCATION: (1)..(10)
<223> OTHER INFORMATION: This region may encompass 1-10 residues
<220> FEATURE:
<221> NAME/KEY: MOD_RES
<222> LOCATION: (13)..(22)
<223> OTHER INFORMATION: Any amino acid
<220> FEATURE:
<221> NAME/KEY: MISC_FEATURE
<222> LOCATION: (13)..(22)
<223> OTHER INFORMATION: This region may encompass 1-10 residues
<220> FEATURE:
<223> OTHER INFORMATION: See specification as filed for detailed
      description of substitutions and preferred embodiments

<400> SEQUENCE: 137

Xaa Xaa Xaa Xaa Xaa Xaa Xaa Xaa Xaa Xaa Tyr His Xaa Xaa Xaa Xaa
1               5                   10                  15

Xaa Xaa Xaa Xaa Xaa Xaa
            20

<210> SEQ ID NO 138
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Any amino acid
<220> FEATURE:
<221> NAME/KEY: MISC_FEATURE
<222> LOCATION: (1)..(10)
<223> OTHER INFORMATION: This region may encompass 1-10 residues
<220> FEATURE:
<221> NAME/KEY: MOD_RES
<222> LOCATION: (13)..(22)
<223> OTHER INFORMATION: Any amino acid
<220> FEATURE:
<221> NAME/KEY: MISC_FEATURE
<222> LOCATION: (13)..(22)
<223> OTHER INFORMATION: This region may encompass 1-10 residues
<220> FEATURE:
<223> OTHER INFORMATION: See specification as filed for detailed
      description of substitutions and preferred embodiments

<400> SEQUENCE: 138

Xaa Xaa Xaa Xaa Xaa Xaa Xaa Xaa Xaa Xaa His Gln Xaa Xaa Xaa Xaa
1               5                   10                  15

Xaa Xaa Xaa Xaa Xaa Xaa
            20

<210> SEQ ID NO 139
<211> LENGTH: 24
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Any amino acid or absent
<220> FEATURE:
<221> NAME/KEY: MOD_RES
<222> LOCATION: (15)..(24)
<223> OTHER INFORMATION: Any amino acid or absent
<220> FEATURE:
<223> OTHER INFORMATION: See specification as filed for detailed
      description of substitutions and preferred embodiments

<400> SEQUENCE: 139

Xaa Xaa Xaa Xaa Xaa Xaa Xaa Xaa Xaa Xaa Val Asp Gly Trp Xaa Xaa
1               5                   10                  15

Xaa Xaa Xaa Xaa Xaa Xaa Xaa Xaa
            20

<210> SEQ ID NO 140
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Any amino acid or absent
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (30)..(39)
<223> OTHER INFORMATION: Any amino acid or absent
<220> FEATURE:
<223> OTHER INFORMATION: See specification as filed for detailed
      description of substitutions and preferred embodiments

<400> SEQUENCE: 140

Xaa Xaa Xaa Xaa Xaa Xaa Xaa Xaa Xaa Xaa Lys Xaa Xaa Thr Gln Xaa
1               5                   10                  15

Xaa Ile Xaa Xaa Xaa Thr Xaa Xaa Val Asn Xaa Xaa Ile Xaa Xaa Xaa
            20                  25                  30

Xaa Xaa Xaa Xaa Xaa Xaa Xaa
        35

<210> SEQ ID NO 141
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Any amino acid or absent
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (27)..(28)
<223> OTHER INFORMATION: Any amino acid or absent
<220> FEATURE:
<221> NAME/KEY: MISC_FEATURE
<222> LOCATION: (27)..(28)
<223> OTHER INFORMATION: This region may be absent in its entirety
<220> FEATURE:
<221> NAME/KEY: MOD_RES
<222> LOCATION: (30)..(39)
<223> OTHER INFORMATION: Any amino acid or absent
<220> FEATURE:
<223> OTHER INFORMATION: See specification as filed for detailed
      description of substitutions and preferred embodiments

<400> SEQUENCE: 141

Xaa Xaa Xaa Xaa Xaa Xaa Xaa Xaa Xaa Xaa Lys Xaa Xaa Thr Gln Xaa
1               5                   10                  15

Xaa Ile Xaa Xaa Xaa Thr Xaa Xaa Val Asn Xaa Xaa Ile Xaa Xaa Xaa
            20                  25                  30

Xaa Xaa Xaa Xaa Xaa Xaa Xaa
            35
```